US008575200B2

(12) United States Patent
Bolli et al.

(10) Patent No.: US 8,575,200 B2
(45) Date of Patent: *Nov. 5, 2013

(54) PYRIDIN-2-YL DERIVATIVES AS IMMUNOMODULATING AGENTS

(75) Inventors: Martin Bolli, Alischwil (CH); Cyrille Lescop, Kembs (FR); Boris Mathys, Prattein (CH); Claus Mueller, Weil am Rhein (DE); Oliver Nayler, Arlesheim (CH); Beat Steiner, Dornach (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 215 days.

This patent is subject to a terminal disclaimer.

(21) Appl. No.: 12/920,656

(22) PCT Filed: Feb. 25, 2009

(86) PCT No.: PCT/IB2009/050749
§ 371 (c)(1),
(2), (4) Date: Sep. 2, 2010

(87) PCT Pub. No.: WO2009/109872
PCT Pub. Date: Sep. 11, 2009

(65) Prior Publication Data
US 2010/0331372 A1     Dec. 30, 2010

(30) Foreign Application Priority Data
Mar. 7, 2008  (WO) .................. PCT/IB2008/050848

(51) Int. Cl.
A61K 31/4439 (2006.01)
C07D 413/04 (2006.01)

(52) U.S. Cl.
USPC ....................... 514/340; 546/269.4

(58) Field of Classification Search
USPC ....................... 546/269.4; 514/340
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 7,834,039 B2 | 11/2010 | Hobson et al. | |
| 8,003,800 B2 | 8/2011 | Bolli et al. | |
| 8,044,076 B2 | 10/2011 | Bolli et al. | |
| 8,133,910 B2 | 3/2012 | Bolli et al. | |
| 8,288,554 B2 * | 10/2012 | Bolli et al. | 546/268.7 |
| 8,299,086 B2 | 10/2012 | Bolli et al. | |
| 2007/0021443 A1 | 1/2007 | Ohlmeyer | |
| 2007/0043014 A1 | 2/2007 | Doherty et al. | |
| 2007/0043104 A1 | 2/2007 | Luthman et al. | |
| 2007/0270438 A1 | 11/2007 | Bhattacharya et al. | |
| 2008/0064740 A1 | 3/2008 | Bolli et al. | |
| 2008/0113961 A1 | 5/2008 | Nishi et al. | |
| 2008/0176926 A1 | 7/2008 | Bolli et al. | |
| 2008/0194670 A1 | 8/2008 | Bolli et al. | |
| 2008/0249093 A1 | 10/2008 | Colandrea et al. | |
| 2008/0300294 A1 | 12/2008 | Bolli et al. | |
| 2008/0306124 A1 | 12/2008 | Albert et al. | |
| 2008/0318955 A1 | 12/2008 | Bolli et al. | |
| 2009/0005421 A1 | 1/2009 | Bolli et al. | |
| 2009/0275554 A1 | 11/2009 | Habashita et al. | |
| 2010/0048648 A1 | 2/2010 | Bolli et al. | |
| 2010/0063108 A1 | 3/2010 | Bolli et al. | |
| 2010/0075946 A1 | 3/2010 | Bolli et al. | |
| 2010/0087417 A1 | 4/2010 | Bolli et al. | |
| 2010/0087495 A1 | 4/2010 | Bolli et al. | |
| 2010/0168005 A1 | 7/2010 | Bolli et al. | |
| 2010/0234346 A1 | 9/2010 | Bolli et al. | |
| 2010/0240717 A1 | 9/2010 | Bolli et al. | |
| 2010/0261702 A1 | 10/2010 | Bolli et al. | |
| 2011/0028448 A1 | 2/2011 | Bolli et al. | |
| 2011/0028449 A1 | 2/2011 | Bolli et al. | |
| 2011/0046170 A1 | 2/2011 | Bolli et al. | |
| 2011/0212998 A1 | 9/2011 | Bolli et al. | |
| 2012/0108638 A1 | 5/2012 | Bolli et al. | |

FOREIGN PATENT DOCUMENTS

| | | |
|---|---|---|
| DE | 10237883 | 3/2004 |
| EP | 0476646 | 3/1992 |
| EP | 0702003 | 6/1998 |
| EP | 1873153 | 1/2008 |
| JP | 2008120794 | 5/2008 |
| WO | WO 91/15583 | 10/1991 |
| WO | WO 99/46277 | 9/1999 |
| WO | WO 00/45799 | 8/2000 |

(Continued)

OTHER PUBLICATIONS

Hu et al., "Sphingosine-1-phosphate, etc.," Mol. Biol. Rep. (2011) 38:4225-4230.*
Van der Giet et al., "Relevance and potential, etc.," Biol. Chem., 389, pp. 1381-1390 (2008).*
Jo et al., "Spingosine-1-phosphate, etc.," Kidney International (2008) 73, 1220-1230.*
Bode et al., "Immune Regulation, etc.," Arch. Immunol. Ther. Exp. (2012) 60: 3-12.*

(Continued)

Primary Examiner — Patricia L Morris
(74) Attorney, Agent, or Firm — Hoxie & Associates L.L.C.

(57) ABSTRACT

The invention relates to pyridine derivatives of Formula (I)

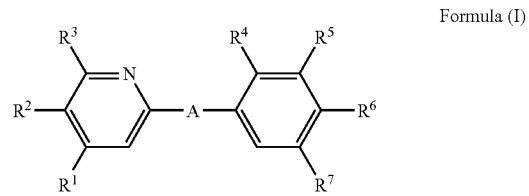

Formula (I)

wherein A, $R^1$, $R^2$, $R^3$, $R^4$, $R^5$, $R^6$ and $R^7$ are as described in the description, their preparation and their use as pharmaceutically active compounds. Said compounds particularly act as immunomodulating agents.

14 Claims, No Drawings

(56) References Cited

FOREIGN PATENT DOCUMENTS

| WO | WO 01/12627 | 2/2001 |
|---|---|---|
| WO | WO 02/068417 | 9/2002 |
| WO | WO 03/062248 | 7/2003 |
| WO | WO 03/062252 | 7/2003 |
| WO | WO 03/105771 | 12/2003 |
| WO | WO 2004/035538 | 4/2004 |
| WO | WO 2004/056789 | 7/2004 |
| WO | WO 2004/103279 | 12/2004 |
| WO | WO 2005/014525 | 2/2005 |
| WO | WO 2005/032465 | 4/2005 |
| WO | WO 2005/058848 | 6/2005 |
| WO | WO 2005/115382 | 12/2005 |
| WO | WO 2006/047195 | 5/2006 |
| WO | WO 2006/100631 | 9/2006 |
| WO | WO 2006/114400 | 11/2006 |
| WO | WO 2006/115188 | 11/2006 |
| WO | WO 2006/131336 | 12/2006 |
| WO | WO 2007/001973 | 1/2007 |
| WO | WO 2007/085451 | 8/2007 |
| WO | WO 2007/098474 | 8/2007 |
| WO | WO 2007/132307 | 11/2007 |
| WO | WO 2008/029370 | 3/2008 |
| WO | WO 2008029370 | 3/2008 |
| WO | WO 2008/037476 | 4/2008 |
| WO | WO 2008/076356 | 6/2008 |
| WO | WO 2008/091967 | 7/2008 |
| WO | WO 2009/043889 | 4/2009 |
| WO | WO 2009/043890 | 4/2009 |
| WO | WO 2009/060278 | 5/2009 |
| WO | WO 2009/151529 | 12/2009 |
| WO | WO 2011/007324 | 1/2011 |

OTHER PUBLICATIONS

Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Robinson, Medical Therapy of Inflammatory Bowel Disease for the 21st century, Eur. J. Surg. 164, Suppl. 582, pp. 90-98, (1998).*
Spiegel et al., Nature Reviews Immunology, vol. 11, No. 6, pp. 403-415, Jun. 2011.*
U.S. Appl. No. 12/920,569, filed Sep. 1, 2010, Bolli, et al.
U.S. Appl. No. 12/920,572, filed Sep. 1, 2010, Bolli, et al.
U.S. Appl. No. 12/920,574, filed Sep. 1, 2010, Bolli, et al.
U.S. Appl. No. 12/673,918, filed Feb. 17, 2010, Bolli, et al.
Abhandlung, Z., "Stickstoffhaltige Derivate der Mekonsäure und ihre Umwandlung in Pyridin", Journal für Prkitsche Chemie, vol. 27, pp. 257-294, (1883).
Biyouki, M. A. A., et al., "Hydroxymethylation and Carbamoylation of Di- and Tetramethylpyridines Using Radical Substitution (Minisci) Reactions", Synthetic Communications, vol. 28, pp. 3817-3825, (1989).
Brain, C.T., et al., "Novel procedure for the synthesis of 1,3,4-oxadiazoles from 1,2-diacylhydrazines using polymer-supported Burgess reagent under microwave conditions", Tetrahedron Lett., vol. 40, pp. 3275-3278, (1999).
Burstein, C., et al., "Imidazo[1,5-a]pyridine-3-ylidenes—pyridine derived N-heterocyclic carbine ligands", Tetrahedron, vol. 61. pp. 6207-6217, (2004).
Chakraborti, A.K., et al., "One-Pot Synthesis of Nitriles from Aldehydes Under Microwave Irradiation: Influence of the Medium and Mode of Microwave Irradiation on Product Formation", Tetrahedron, vol. 55, pp. 13265-13268, (1999).
Comins, D.L., et al., "Regiospecific α—Alkylation of 4-Chloro(bromo) pyridine", J. Org. Chem., vol. 50, pp. 4410-4411, (1985).

Fallahpour, R.-A., "An Efficient and Easy Route to Trimethyl Derivatives of 2,2':6',2"-Terpyridine", Synthesis, No. 12, pp. 1665-1667, (2000).
Gangloff, A.R., et al., "Synthesis of 3,5-disubstituted-1,2,4-oxadiazoles using tetrabutylammonium fluoride as a mild and efficient catalyst", Tetrahedron Lett., vol. 42, pp. 1441-1443, (2001).
Garcia, M.A., et al., "Synthesis, Biological Evaluation, and Three-Dimensional Quantitative Structure-Activity Relationship Study of Small-Molecule Positive Modulators of Adrenomedullin", J. Med. Chem., vol. 48, pp. 4068-4075, (2005).
Gould, P.L., "Salt Selection for Basic Drugs", International Journal of Pharmaceutics, vol. 33, pp. 201-217, (1986).
Hamze, A., et al., "Synthesis of Various 3-Substituted 1,2,4-Oxadiazole-Containing Chiral α- and r-Amino Acids from Fmoc-Protected Aspartic Acid", J. Org. Chem., vol. 68, pp. 7316-7321, (2003).
Hla, T., et al., "An Abundant Transcript Induced in Differentiating Human Endothelial Cells Encodes a Polypeptide with Structural Similarities to G-protein-coupled Receptors", Biol. Chem., vol. 265, pp. 9308-9313, (1990).
Inouye, M., et al., "Saccharide-Dependent Induction of Chiral Helicity in Achiral Synthetic Hydrogen-Bonding Oligomers", J. Am. Chem. Soc., vol. 126, pp. 2022-2027, (2004).
John, E.O., et al., "Reactions of (Difluoroamino)difluoroacetonitrile and (Difluoroamino) difluoroacetamidoxime", Inorganic Chemistry, vol. 27, pp. 3100-3104, (1988).
Kaboudin, B., et al., "One-Pot Synthesis of 1,2,4-Oxadiazoles Mediated by Microwave Irradiation Under Solvent-Free Condition", Heterocycles, vol. 60, No. 10, pp. 2287-2292, (2003).
Katz, R. B., et al., "An Improved Method for the Mono-Hydroxymethylation of Pyridines. A Modification of the Minisci Procedure", Synthetic Communications, vol. 19, pp. 317-325, (1989).
Kaminski, T., et al., "Side-Chain Retention During Lithiation of 4-Picoline and 3,4-Lutidine: Easy Access to Molecular Diversity in Pyridine Series", J. Org. Chem., vol. 19, pp. 3855-3860, (2003).
Kerins, F., et al., "Generation of Substituted Styrenes via Suzuki Cross-Coupling of Aryl Halides with 2,4,6-Trivinylcyclotriboroxane", J. Org. Chem., vol. 67 pp. 4968-4971, (2002).
Matsushita, H., et al., "Palladium-Catalyzed Reactions of Allylic Electrophiles with Organometallic Reagents. A Regioselective 1,4-Elimination and a Regio- and Stereoselective Reduction of Allylic Derivatives", J. Org. Chem., vol. 47, pp. 4161-4165, (1982).
Meyer, E., et al, "Synthesis of New 1,2,4- and 1,3,4-Oxadiazole Derivatives", Synthesis, No. 6, pp. 899-905, (2003).
Nguyen, T., et al., "Combined Directed Ortho Metalation/Cross-Coupling Strategies: Synthesis of the Tetracyclic A/B/C/D Ring Core of the Antitumor Agent Camptothecin", J. Org. Chem., vol. 69, pp. 7816-7821, (2004).
Pierrat, P., et al., "Unusual t-BuLi Induced Ortholithiation versus Halogen-Lithium Exchange in Bromopyridines: Two Alternative Strategies for Functionalization", Synlett, No. 13, pp. 2319-2322, (2004).
Poulain, R.F., et al. "Parallel synthesis of 1,2,4-oxadiazoles from carboxylic acids using an improved, uronium-based, activation", Tetrahedron Lett., vol. 42, pp. 1495-1498, (2001).
Roth, B., et al., "2,4-Diamino-5-benzylpyrimidines and Analogues as Antibacterial Agents. 9. Lipophilic Trimethoprim Analogues as Antigonococcal Agents", J. Med. Chem., vol. 31, pp. 122-129, (1988).
Simeone, J.P., et al., "Modification of the Pyridine Moiety of Nonpeptidyl Indole GnRH Receptor Antagonists", Bioorganic & Medicinal Chemistry Letters, vol. 12, pp. 3329-3332, (2002).
Srivastava, R.M., et al., Synthesis of 3-Aryl-5-[Thien-3-Yl Methyl]-1,2,4-Oxadiazoles, Synthetic Commun., vol. 29, pp. 1437-1450, (1999).
Suzuki, T., et al., "Synthesis of the Selective 5-Hydroxytryptamine4 (5-$HT_4$) Receptor Agonist (+)-(S)-2-Chloro-5-methoxy-4-[5-(2-piperidylmethyl)-1,2,4-oxadiazol-3-yl]aniline", Chem. Pharm. Bull., vol. 47, No. 1, pp. 120-122, (1999).

(56) References Cited

OTHER PUBLICATIONS

Szczepankiewicz, B.G., et al., "Aminopyridine-Based c-Jun N-Terminal Kinase Inhibitors with Cellular Activity and Minimal Cross-Kinase Activity", J. Med. Chem., vol. 49, pp. 3563-3580, (2006).
Trapani, G., et al., "Propofol Analogues. Synthesis, Relationships between Structure and Affinity at $GABA_A$ Receptor in Rat Brain, and Differential Electrophysiological Profile at Recombinant Human $GABA_A$ Receptors". J. Med. Chem., vol. 41, pp. 1846-1854, (1998).
Vermonden, T., et al., "Synthesis of 4-functionalized terdendate pyridine-based ligands", Tetrahedron, vol. 59, pp. 5039-5045, (2003).
Yan, L., et al., "Discovery of 3-arylpropionic acids as potent agonists of sphingosine-1-phosphate receptor-1 (S1P1) with high selectivity against all other known S1P receptor subtypes", Bioorganic & Med. Chem. Lett., vol. 16, pp. 3679-3683, (2006).
Ziener, U., et al., "Recognition-Directed Supramolecular Assemblies of Metal Complexes of Terpyridine Derived Ligands with Self-Complementary Hydrogen Bonding Sites", Chemistry-A European Journal, vol. 6, pp. 4132-4139, (2000).
Alvernhe et al; "Synthesis and Reactivity of 3-chloro-3-trifluoromethylacroleins: Stabilization of the Tetrahedral Intermediate in a Nucleophilic Vinylic "Substitution""; Bull. Soc. Chim. Fr.; 131, 1994, 167-172.
Cui et al; Design and Synthesis of Highly Constrained Factor Xa Inhibitors: Amidine-Substituted Bis(benzoyl)-[1,3]-diazepan-2-ones and Bis(benzylidene)-bis(gem-dimethyl)Cycloketones, Bioorganic Medicinal Chemistry, 2003, pp. 3379-3392, vol. 11.
Ecke et al; "Ortho-Alkylation of Aromatic Amines"; Journal of Organic Chemistry, 1957, pp. 639-642, vol. 22.
Furnster et al; "Iron Catalyzed Cross-Coupling Reactions"; J. Am. Chem. Soc., 124, 2002, 13856-13863.
Furnster et al; "Iron-Catalyzed Cross-coupling Reactions of Alkyl-grignard Reagents with Aryl Chlorides, Tosylates, and Triflates"; Angew. Chem.; 2002; vol. 41, No. 4, pp. 609-612.
Glennon et al; "B-Oxygenated Analogues of the 5-HT2A Serotonin Receptor Agonist 1-(4Bromo-2,5-dimethoxyphenyl)-2-aminopropane", Journal of Medicinal Chemistry, 2004, pp. 6034-6041, vol. 47.
Golub et al, "Molecular Classification of Cancer: Class Discovery and Class Prediction by Gene Expression Monitoring"; Science, 1999, vol. 286, 531-537.
Gronowitz et al; "On the Synthesis of Branched Saturated Fatty Acids"; Lipids, vol. 28, 1993, 889-897.
Khlestkin et al; "Recent Advances in the Application of A,O-dialkylhydroxylamines in Organic Chemistry"; Current Organic Chemistry, 7; 2003; 967-993.
Kiryanov et al; "Synthesis of 2-Alkoxy-Substituted Thlophenes, 1,3-Thiazoles, and Related S-Heterocycles via Lawesson's Reagent-Mediated Cyclization under Microwave Irradiation: Applications for Liquid Crystal Synthesis"; Journal of Organic Chemistry, 2001, pp. 7925-7929, vol. 66.
Knight et al; "Generation and Synthetic Utility of Dianions Derived from Thiophencarboxylic Acids"; J. Chem. Soc., Perkin Trans. 1; 1983; 791-794.
Lala et al; "Role of Nitric Oxide in Tumor Progression: Lessons From Experimental Tumors"; Cancer and Metastasis Reviews (1998), 17, 91-106.
Lamattina; "The Synthesis of 2-Amino-4-(4-imidazolyl)pyridines"; J. Heterocyclic Chem.; 20; 1983; 533-538.
Mentzel et al; "N-Methoxy N-methyl amides (Weinred amides) in Modern Organic Synthesis"; Journal fur Praktische Chemie Chiker-Zeitung; 339; 1997; 517-524.
Notice of Allowance dated Jun. 13, 2012 for U.S. Appl. No. 12/310,763.
Notice of Allowance dated Nov. 28, 2012 for U.S. Appl. No. 12/920,574.
Office Action dated Apr. 26, 2012 for U.S. Appl. No. 12/531,374.
Office Action dated Dec. 2, 2011 for U.S. Appl. No. 12/310,763.
Office Action dated Dec. 2, 2011 for U.S. Appl. No. 12/531,374.
Office Action dated Dec. 6, 2011 for U.S. Appl. No. 12/310,801.
Office Action dated Jun. 27, 2012 for U.S. Appl. No. 12/310,801.
Office Action dated Jun. 7, 2011 for U.S. Appl. No. 12/310,763.
Office Action dated Mar. 1, 2012 for U.S. Appl. No. 12/310,763.
Office Action dated Oct. 8, 2010 for U.S. Appl. No. 12/310,763.
Paine, "A Convenient Synthesis of Nicotinate Esters from 3-cyanopyridones"; J. Heterocyclic; 1987; vol. 24, pp. 351-355.
Patani et al; "Bioisosterism: A Rational Approach in Drug Design"; Chem. Rev. 1996, vol. 96, No. 8, pp. 3147-3176.
Pesson et al; "Antibacteriens de Syntheses—Derives de L'acide Pipemidique"; Eur. J. Med. Chem.; 15; 1980; 263-268.
Sato et al; "Synthesis and Evaluation of Substituted 4-alkoxy-2-aminopyridines as Novel Neuropeptide Y1 Receptor Antagonists", Bioorganic and Medicinal Chemistry Letters, 2004, pp. 1761-1764, vol. 14.
Silverman; "The Organic Chemistry of Drug Design and Drug Action"; 2004; Elsevier, pp. 29-32.
Silverman; "The Organic Chemistry of Drug Design and Drug Action"; 2004; Elsevier, pp. 9.
Singh et al; "The Growing Synthetic Utility of Weinreb's Amide"; Journal fur Praktische Chemie; 342; 2000; 340-347.
Tsukerman et al; "Basicity and Structure of .alpha., .beta.-unsaturated Ketones of a Heterocyclic Series. VII. Methyl-substituted Analogs of Chalcones"; Chemical Abstracts Service; XP002467039; STN Databse Accession No.; 1971: 87024.
Wild et al; "Asymmetric Synthesis of (S)-(—)-acromelobic Acid"; Eur. J. Org. Chem.; 2003; pp. 4445-4440.
Xu et al; "Acyclic Analogues of Adenosine Biphosphates as P2Y Receptor Antagonists: Phosphate Substitution Leads to Multiple Pathways of Inhibition of Platelet Aggregation"; Journal of Medicinal Chemistry, 2002, pp. 5694-5709, vol. 45.
Zhen et al, "Discovery of Potent 3,5-Diphenyl-1,2,4-oxadiazole Sphingosine-l-phosphate-1 (S1P1) Receptor Agonists with Exceptional Selectivity Against S1P2 and S1P", Journal of Medicinal Chemistry, 2005, pp. 6169-6173, vol. 48, No. 20.
Buzard et al; "Expert Opinion on Therapuetic Patents"; vol. 18, No. 10; pp. 1141-1159 (2008).
Doucet; Eur. J. Org. Chem.; pp. 2013-2030; 2008.
Gennaro, "Remington: The Science and Practice of Pharmacy", Table of Contents; 20th Edition, Philadelphia College of Pharmacy and Science 2003.
Gibson (Editor); Pharmaceutical Preformulation and Formulation; HIS Health Group, 2001.
Greene et al, "Protective Groups in Organic Synthesis", Table of Contents; 3rd Edition, Wiley New York, 1991.
Kocienski, "Protecting Groups", Thieme Stuggart, 1994; Introduction.
Meyer Zu Heringdorf et al; "Pharmacology of the Sphingosine-1-Phosphate Signalling System"; Sphingolipids: Basic Science and Drug Development; Handbook of Experimental Pharmacology 215, pp. 239-253; 2013.
Nguyen et al; "Combined Directed Ortho Metalation/Cross-Coupling Strategies: Synthesis of the Tetracyclic A/B/C/D Ring Core of the Antitumor Agent Camptothecin"; J. Org. Chem., vol. 69, pp. 7816-7821; (2004).
Notice of Allowance dated Nov. 18, 2011 for U.S. Appl. No. 12/747,280.
Office Action—Final dated Feb. 7, 2013 for U.S. Appl. No. 12/637,918.
Office Action—Final dated Nov. 8, 2012 for U.S. Appl. No. 12/310,801.
Office Action—Restriction dated Apr. 26, 2013 for U.S. Appl. No. 13/383,619.
Office Action—Restriction dated Jul. 24, 2012 for U.S. Appl. No. 12/920,569.
Office Action dated Feb. 17, 2012 for U.S. Appl. No. 12/673,918.
Office Action dated Jan. 3, 2013 for U.S. Appl. No. 12/531,374.
Office Action dated Jan. 4, 2013 for U.S. Appl. No. 12/920,569.
Office Action dated Jun. 11, 2012 for U.S. Appl. No. 12/673,918.
Remington, "The Science and Practice of Pharmacy", 21st Edition (2005), Part 5—Table of Contents, "Pharmaceutical Manufacturing", Published by Lippincott Williams & Wilkins.

(56) References Cited

OTHER PUBLICATIONS

Schurer et al; ACS Chemical Biolog, vol. 3; No. 8; pp. 486-498; 2008.
Notice of Allowance of U.S. Appl. No. 12/531,374 dated Jul. 17, 2013.
Notice of Allowance of U.S. Appl. No. 12/673,918 dated Jul. 23, 2013.
Notice of Allowance of U.S. Appl. No. 12/310,801 dated Jun. 19, 2013.
U.S. Appl. No. 13/980,764, filed Jul. 19, 2013, Bolli et al.

* cited by examiner

PYRIDIN-2-YL DERIVATIVES AS IMMUNOMODULATING AGENTS

CROSS REFERENCE TO RELATED APPLICATIONS

This application is a United States Application under 35 U.S.C. 371 claiming benefit of PCT Application No. PCT/IB2009/050749, filed on Feb. 25, 2009, which claims the benefit of PCT Application No. PCT/IB2008/050848, filed on Mar. 7, 2008.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

i) The invention relates to pyridine compounds of the Formula (I),

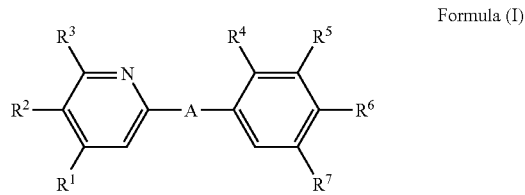

Formula (I)

wherein
A represents

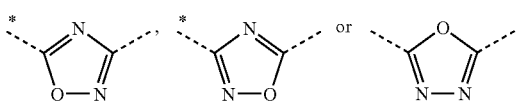

wherein the asterisks indicate the bond that is linked to the pyridine group of Formula (I);

$R^1$ represents methyl, ethyl or methoxy; $R^2$ represents hydrogen; and $R^3$ represents $C_{2-5}$-alkyl or $C_{1-4}$-alkoxy; or $R^1$ represents $C_{2-5}$-alkyl or $C_{1-4}$-alkoxy; $R^2$ represents hydrogen; and $R^3$ represents methyl or ethyl; or $R^1$ represents methyl, ethyl, or methoxy; $R^2$ represents $C_{3-5}$-alkyl; and $R^3$ represents hydrogen;

$R^4$ represents hydrogen or methoxy;

$R^5$ represents hydrogen, $C_{1-3}$-alkyl, or methoxy;

$R^6$ represents —$CH_2$—$(CH_2)_n$—$CONR^{61}R^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, hydroxy, hydroxy-$C_{2-4}$-alkoxy, di-(hydroxy-$C_{1-2}$-alkyl)-$C_{1-2}$-alkoxy, 2,3-dihydroxy-propoxy, —$OCH_2$—$(CH_2)_n$—$NR^{61}R^{62}$, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, —$OCH_2$—CH(OH)—$CH_2$—$NR^{61}R^{62}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, —$OCH_2$—$(CH_2)_n$—$NHSO_2R^{63}$, —$OCH_2$—CH(OH)—$CH_2$—$NHSO_2R^{63}$, —$OCH_2$—$(CH_2)_n$—$NHCOR^{64}$, or —$OCH_2$—CH(OH)—$CH_2$—$NHCOR^{64}$;

$R^{61}$ represents hydrogen, methyl, ethyl, 2-hydroxyethyl, carboxymethyl, 1-($C_{1-5}$-alkylcarboxy)methyl, 2-carboxyethyl, 2-($C_{1-5}$-alkylcarboxy)ethyl, 2-aminoethyl, or 2-methylamino-ethyl;

$R^{62}$ represents hydrogen, or methyl;

$R^{63}$ represents $C_{1-3}$-alkyl, methylamino, ethylamino, or dimethylamino;

$R^{64}$ represents hydroxymethyl, 2-hydroxyethyl, aminomethyl, methylaminomethyl, 2-aminoethyl, or 2-methylaminoethyl;

n represents the integer 1, or 2; and $R^7$ represents hydrogen, methyl or chloro.

The general terms used hereinbefore and hereinafter preferably have, within this disclosure, the following meanings, unless otherwise indicated:

The term "$C_{x-y}$-alkyl" (x and y each being an integer) refers to a saturated straight or branched hydrocarbon chain with x to y carbon atoms. Thus, the term $C_{1-5}$-alkyl, alone or in combination with other groups, means saturated, branched or straight chain groups with one to five carbon atoms. Examples of $C_{1-5}$-alkyl groups are methyl, ethyl, n-propyl, n-butyl, iso-butyl, n-pentyl, 3-pentyl, and iso-pentyl. Preferred examples of $C_{1-3}$-alkyl groups are methyl and ethyl. Preferred examples of $C_{2-5}$-alkyl groups are ethyl, n-propyl, iso-propyl, n-butyl, iso-butyl, n-pentyl, 3-pentyl and iso-pentyl. Preferred examples of $C_{2-4}$-alkyl groups are ethyl, n-propyl, iso-propyl, n-butyl, and iso-butyl.

The term "$C_{x-y}$-alkoxy" (x and y each being an integer) refers to an alkyl-O— group wherein the alkyl group refers to a straight or branched hydrocarbon chain with x to y carbon atoms. For example, a $C_{1-4}$-alkoxy group contains from one to four carbon atoms and includes methoxy, ethoxy, n-propoxy, iso-propoxy, n-butoxy, iso-butoxy, sec-butoxy, and tert-butoxy. Preferred examples of $C_{1-4}$-alkoxy groups are ethoxy, propoxy, iso-propoxy, and iso-butoxy. Preferred examples of $C_{2-4}$-alkoxy groups are ethoxy, n-propoxy, and iso-propoxy. Examples of $C_{1-3}$-alkoxy groups are methoxy, ethoxy, n-propoxy, and iso-propoxy.

ii) Another embodiment of the invention relates to pyridine derivatives according to embodiment i), wherein A represents

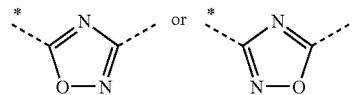

wherein the asterisks indicate the bond that is linked to the pyridine group of Formula (I).

iii) Another embodiment of the invention relates to pyridine derivatives according to embodiment i), wherein A represents

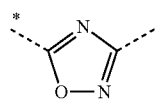

wherein the asterisk indicates the bond that is linked to the pyridine group of Formula (I).

iv) Another embodiment of the invention relates to pyridine derivatives according to any one of the embodiments i) to iii), wherein $R^1$ represents methyl or methoxy, $R^2$ represents hydrogen, and $R^3$ represents $C_{2-4}$-alkyl or $C_{1-3}$-alkoxy.

v) Another embodiment of the invention relates to pyridine derivatives according to any one of the embodiments i) to iii), wherein $R^1$ represents methyl, $R^2$ represents hydrogen, and $R^3$ represents $C_{2-4}$-alkyl or $C_{1-3}$-alkoxy.

vi) Another embodiment of the invention relates to pyridine derivatives according to any one of the embodiments i) to iii), wherein $R^1$ represents $C_{2-4}$-alkyl or $C_{1-3}$-alkoxy, $R^2$ represents hydrogen, and $R^3$ represents methyl.

vii) Another embodiment of the invention relates to pyridine derivatives according to any one of the embodiments i) to iii), wherein $R^1$ represents $C_{2-4}$-alkyl, $R^2$ represents hydrogen, and $R^3$ represents methyl.

viii) Another embodiment of the invention relates to pyridine derivatives according to any one of the embodiments i) to iii), wherein $R^1$ represents methyl, $R^2$ represents $C_4$-alkyl, and $R^3$ represents hydrogen.

ix) Another embodiment of the invention relates to pyridine derivatives according to any one of the embodiments i) to viii), wherein at least one of $R^4$, $R^5$ and $R^7$ represents a group other than hydrogen.

x) Another particular embodiment of the invention relates to pyridine derivatives according to any one of the embodiments i) to viii), wherein $R^4$ represents methoxy, and $R^5$ and $R^7$ represent hydrogen.

xi) Another particular embodiment of the invention relates to pyridine derivatives according to any one of the embodiments i) to viii), wherein $R^4$ represents hydrogen, $R^5$ represents $C_{1-3}$-alkyl or methoxy, and $R^7$ represents methyl or chloro.

xii) Another particular embodiment of the invention relates to pyridine derivatives according to any one of the embodiments i) to viii), wherein $R^4$ represents hydrogen, $R^5$ represents $C_{1-2}$-alkyl or methoxy, and $R^7$ represents methyl or chloro.

xiii) Another particular embodiment of the invention relates to pyridine derivatives according to any one of the embodiments i) to viii), wherein $R^4$ represents hydrogen, $R^5$ represents ethyl or methoxy, and $R^7$ represents methyl or chloro.

xiv) Another particular embodiment of the invention relates to pyridine derivatives according to any one of the embodiments i) to viii), wherein $R^4$ represents hydrogen, $R^5$ represents ethyl, and $R^7$ represents methyl.

xv) Another embodiment of the invention relates to pyridine derivatives according to any one of the embodiments i) to xiv), wherein $R^6$ represents —CH$_2$—(CH$_2$)$_n$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, di-(hydroxy-C$_{1-2}$-alkyl)-C$_{1-2}$-alkoxy, 2,3-dihydroxy-propoxy, —OCH$_2$—(CH$_2$)$_n$—NR$^{61}$R$^{62}$, 2-[(azetidine-3-carboxylic acid)-1-yl]-ethoxy, 2-[(azetidine-3-carboxylic acid C$_{1-5}$-alkylester)-1-yl]ethoxy, 2-[(pyrrolidine-3-carboxylic acid)-1-yl]-ethoxy, 2-[(pyrrolidine-3-carboxylic acid C$_{1-5}$-alkylester)-1-yl]ethoxy, —OCH$_2$—CH(OH)—CH$_2$—NR$^{61}$R$^{62}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, or —OCH$_2$—CH(OH)—CH$_2$—NHCOR$^{64}$.

xvi) Another embodiment of the invention relates to pyridine derivatives according to any one of the embodiments i) to xiv), wherein $R^6$ represents —CH$_2$—(CH$_2$)$_n$—CONR$^{61}$R$^{62}$, 1-(3-carboxy-azetidinyl)-3-propionyl, 1-(2-carboxy-pyrrolidinyl)-3-propionyl, 1-(3-carboxy-pyrrolidinyl)-3-propionyl, 2,3-dihydroxy-propoxy, —OCH$_2$—CH(OH)—CH$_2$—NR$^{61}$R$^{62}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, or —OCH$_2$—CH(OH)—CH$_2$—NHCOR$^{64}$.

xvii) Another embodiment of the invention relates to pyridine derivatives according to any one of the embodiments i) to xiv), wherein $R^6$ represents 2,3-dihydroxy-propoxy, 3-[(azetidine-3-carboxylic acid)-1-yl]-2-hydroxypropoxy, 2-hydroxy-3-[(pyrrolidine-3-carboxylic acid)-1-yl]-propoxy, 2-hydroxy-3-[(pyrrolidine-2-carboxylic acid)-1-yl]-propoxy, or —OCH$_2$—CH(OH)—CH$_2$—NHCOR$^{64}$.

xviii) Another embodiment of the invention relates to pyridine derivatives according to any one of the embodiments i) to xiv), wherein $R^6$ represents 2,3-dihydroxy-propoxy, or —OCH$_2$—CH(OH)—CH$_2$—NHCOR$^{64}$.

xix) Another embodiment of the invention relates to pyridine derivatives according to any one of the embodiments i) to xiv), wherein $R^6$ represents —OCH$_2$—CH(OH)—CH$_2$—NHCOR$^{64}$.

xx) Another embodiment of the invention relates to pyridine derivatives according to any one of the embodiments i) to xvi), wherein $R^{61}$ represents methyl, 2-hydroxyethyl, carboxymethyl, 2-aminoethyl, or 2-methylamino-ethyl.

xxi) Another embodiment of the invention relates to pyridine derivatives according to any one of the embodiments i) to xvi) and xx), wherein $R^{62}$ represents hydrogen.

xxii) Another embodiment of the invention relates to pyridine derivatives according to any one of the embodiments i) to xiv) and xx) to xxi), wherein $R^{63}$ represents methyl.

xxiii) Another embodiment of the invention relates to pyridine derivatives according to any one of the embodiments i) to xxii), wherein $R^{64}$ represents hydroxymethyl.

xxiv) Another embodiment of the invention relates to pyridine derivatives according to any one of the embodiments i) to xvi) and xx) to xxiii), wherein n represents the integer 1.

xxv) Another embodiment of the invention relates to pyridine derivatives according to embodiment i), wherein A represents wherein the asterisk indicates the bond that is linked to the pyridine group of Formula (I);

$R^1$ represents methyl, or methoxy; $R^2$ represents hydrogen; and $R^3$ represents C$_4$-alkyl; or $R^1$ represents C$_4$-alkyl; $R^2$ represents hydrogen; and $R^3$ represents methyl; or $R^1$ represents methyl; $R^2$ represents C$_4$-alkyl; and $R^3$ represents hydrogen;

$R^4$ represents hydrogen;

$R^5$ represents methyl or ethyl;

$R^6$ represents —CH$_2$—(CH$_2$)$_n$—CONR$^{61}$R$^{62}$, hydroxy, 2,3-dihydroxy-propoxy, —OCH$_2$—CH(OH)—CH$_2$—NR$^{61}$R$^{62}$, or —OCH$_2$—CH(OH)—CH$_2$—NHCOR$^{64}$;

$R^{61}$ represents hydrogen, methyl, 2-hydroxyethyl, carboxymethyl, 2-carboxyethyl, or 2-aminoethyl;

$R^{62}$ represents hydrogen;

$R^{64}$ represents hydroxymethyl;

n represents the integer 1; and $R^7$ represents methyl.

xxvi) Another embodiment of the invention relates to pyridine derivatives according to embodiment i), wherein A represents wherein the asterisks indicate the bond that is linked to the pyridine group of Formula (I);

$R^1$ represents methyl or methoxy; $R^2$ represents hydrogen; and $R^3$ represents C$_{2-5}$-alkyl such as isobutyl or 1-ethyl-propyl; or $R^1$ represents C$_{2-5}$-alkyl such as isobutyl; $R^2$ represents hydrogen; and $R^3$ represents methyl; or $R^1$ represents methyl; $R^2$ represents C$_{3-5}$-alkyl such as isobutyl; and $R^3$ represents hydrogen;

$R^4$ represents hydrogen or methoxy;

$R^5$ represents hydrogen, C$_{1-3}$-alkyl (such as methyl, ethyl, or n-propyl), or methoxy;

$R^6$ represents —CH$_2$—(CH$_2$)$_n$—CONR$^{61}$R$^{62}$, hydroxy, hydroxy-C$_{2-4}$-alkoxy (such as 2-hydroxy-ethoxy), di-(hydroxy-C$_{1-2}$-alkyl)-C$_{1-2}$-alkoxy (such as di-(hydroxymethyl)-methoxy or 3-hydroxy-2-hydroxymethyl-propoxy), 2,3-dihydroxy-propoxy, —OCH$_2$—(CH$_2$)$_n$—NR$^{61}$R$^{62}$, 2-[(azetidine-3-carboxylic acid)-1-yl]-ethoxy, —OCH$_2$—CH(OH)—CH$_2$—NR$^{61}$R$^{62}$, —OCH$_2$—(CH$_2$)$_n$—NHSO$_2$R$^{63}$, —OCH$_2$—CH(OH)—CH$_2$—NHSO$_2$R$^{63}$, —OCH$_2$—(CH$_2$)$_n$—NHCOR$^{64}$, or —OCH$_2$—CH(OH)—CH$_2$—NHCOR$^{64}$;

$R^{61}$ represents hydrogen, methyl, 2-hydroxyethyl, 2-carboxyethyl, 2-($C_{1-5}$-alkylcarboxy)ethyl (such as 2-(methylcarboxy)ethyl), or 2-aminoethyl;

$R^{62}$ represents hydrogen or methyl;

$R^{63}$ represents $C_{1-3}$-alkyl (such as ethyl), or dimethylamino;

$R^{64}$ represents hydroxymethyl or methylaminomethyl;

n represents the integer 1; and $R^7$ represents hydrogen, methyl or chloro.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Examples of pyridine compounds according to Formula (I) are selected from:

N—((S)-3-{2-ethyl-4-[5-(6-isobutyl-4-methyl-pyridin-2-yl)-[1,2,4]oxadiazol-3-yl]-6-methyl-phenoxy}-2-hydroxy-propyl)-2-hydroxy-acetamide;

N—((S)-3-{2-ethyl-4-[5-(4-isobutyl-6-methyl-pyridin-2-yl)-[1,2,4]oxadiazol-3-yl]-6-methyl-phenoxy}-2-hydroxy-propyl)-2-hydroxy-acetamide;

2-hydroxy-N—((R)-2-hydroxy-3-{4-[5-(6-isobutyl-4-methoxy-pyridin-2-yl)-[1,2,4]oxadiazol-3-yl]-2,6-dimethyl-phenoxy}-propyl)acetamide;

2-hydroxy-N—((S)-2-hydroxy-3-{4-[5-(6-isobutyl-4-methoxy-pyridin-2-yl)-[1,2,4]oxadiazol-3-yl]-2,6-dimethyl-phenoxy}-propyl)acetamide;

N—((S)-3-{2-ethyl-4-[5-(6-isobutyl-4-methoxy-pyridin-2-yl)-[1,2,4]oxadiazol-3-yl]-6-methyl-phenoxy}-2-hydroxy-propyl)-2-hydroxy-acetamide;

(S)-3-{4-[5-(6-isobutyl-4-methoxy-pyridin-2-yl)-[1,3,4]oxadiazol-2-yl]-2,6-dimethyl-phenoxy}-propane-1,2-diol;

(R)-3-{2-ethyl-4-[5-(5-isobutyl-4-methyl-pyridin-2-yl)-[1,2,4]oxadiazol-3-yl]-6-methyl-phenoxy}-propane-1,2-diol;

(S)-3-{2-ethyl-4-[5-(5-isobutyl-4-methyl-pyridin-2-yl)-[1,2,4]oxadiazol-3-yl]-6-methyl-phenoxy}-propane-1,2-diol;

N—((S)-3-{2-ethyl-4-[5-(5-isobutyl-4-methyl-pyridin-2-yl)-[1,2,4]oxadiazol-3-yl]-6-methyl-phenoxy}-2-hydroxy-propyl)-2-hydroxy-acetamide;

3-{2-ethyl-4-[5-(5-isobutyl-4-methyl-pyridin-2-yl)-[1,2,4]oxadiazol-3-yl]-6-methyl-phenyl}-N-(2-hydroxy-ethyl)-propionamide; and 3-(3-{2-ethyl-4-[5-(5-isobutyl-4-methyl-pyridin-2-yl)-[1,2,4]oxadiazol-3-yl]-6-methyl-phenyl}-propionylamino)-propionic acid.

Further Examples of pyridine compounds according to Formula (I) are selected from:

2-{2-ethyl-4-[5-(5-isobutyl-4-methyl-pyridin-2-yl)-[1,2,4]oxadiazol-3-yl]-6-methyl-phenoxy}-ethylamine;

3-(2-{2-ethyl-4-[5-(5-isobutyl-4-methyl-pyridin-2-yl)-[1,2,4]oxadiazol-3-yl]-6-methyl-phenoxy}-ethylamino)-propionic acid;

N-(2-{2-ethyl-4-[5-(5-isobutyl-4-methyl-pyridin-2-yl)-[1,2,4]oxadiazol-3-yl]-6-methyl-phenoxy}-ethyl)-2-hydroxy-acetamide;

2-{2-ethyl-4-[5-(5-isobutyl-4-methyl-pyridin-2-yl)-[1,2,4]oxadiazol-3-yl]-6-methyl-phenoxy}-propane-1,3-diol;

(S)-1-{2-ethyl-4-[5-(5-isobutyl-4-methyl-pyridin-2-yl)-[1,2,4]oxadiazol-3-yl]-6-methyl-phenoxy}-3-(2-hydroxy-ethylamino)-propan-2-ol;

ethanesulfonic acid ((S)-3-{2-ethyl-4-[5-(5-isobutyl-4-methyl-pyridin-2-yl)-[1,2,4]oxadiazol-3-yl]-6-methyl-phenoxy}-2-hydroxy-propylyamide;

3-((S)-3-{2-ethyl-4-[5-(5-isobutyl-4-methyl-pyridin-2-yl)-[1,2,4]oxadiazol-3-yl]-6-methyl-phenoxy}-2-hydroxy-propylamino)-propionic acid;

(S)-3-(2-ethyl-4-{5-[6-(1-ethyl-propyl)-4-methyl-pyridin-2-yl]-[1,2,4]oxadiazol-3-yl}-6-methyl-phenoxy)-propane-1,2-diol;

N—[(S)-3-(2-ethyl-4-{5-[6-(1-ethyl-propyl)-4-methyl-pyridin-2-yl]-[1,2,4]oxadiazol-3-yl}-6-methyl-phenoxy)-2-hydroxy-propyl]-2-hydroxy-acetamide. (S)-3-(2-Ethyl-4-{5-[6-(1-ethyl-propyl)-4-methoxy-pyridin-2-yl]-[1,2,4]oxadiazol-3-yl}-6-methyl-phenoxy)-propane-1,2-diol;

(S)-3-(2-chloro-4-{5-[6-(1-ethyl-propyl)-4-methoxy-pyridin-2-yl]-[1,2,4]oxadiazol-3-yl}-6-methyl-phenoxy)-propane-1,2-diol;

N—[(S)-3-(2-ethyl-4-{5-[6-(1-ethyl-propyl)-4-methoxy-pyridin-2-yl]-[1,2,4]oxadiazol-3-yl}-6-methyl-phenoxy)-2-hydroxy-propyl]-2-hydroxy-acetamide;

N—[(S)-3-(4-{5-[6-(1-ethyl-propyl)-4-methoxy-pyridin-2-yl]-[1,2,4]oxadiazol-3-yl}-2,6-dimethyl-phenoxy)-2-hydroxy-propyl]-2-hydroxy-acetamide;

N—[(S)-3-(2-chloro-4-{5-[6-(1-ethyl-propyl)-4-methoxy-pyridin-2-yl]-[1,2,4]oxadiazol-3-yl}-6-methyl-phenoxy)-2-hydroxy-propyl]-2-hydroxy-acetamide;

N—[(S)-3-(4-{5-[6-(1-ethyl-propyl)-4-methoxy-pyridin-2-yl]-[1,2,4]oxadiazol-3-yl}-2-methoxy-6-methyl-phenoxy)-2-hydroxy-propyl]-2-hydroxy-acetamide; and N-((2S)-3-{2-ethyl-4-[3-(5-isobutyl-4-methyl-pyridin-2-yl)-[1,2,4]oxadiazol-5-yl]-6-methyl-phenoxy}-2-hydroxy-propyl)-2-hydroxy-acetamide.

The compounds of Formula (I) and their pharmaceutically acceptable salts can be used as medicaments, e.g. in the form of pharmaceutical compositions for enteral or parenteral administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example *Remington, The Science and Practice of Pharmacy,* 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders associated with an activated immune system and to be prevented/treated with the compounds of Formula (I) are for example selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

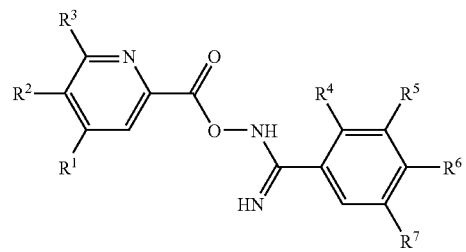

Structure 1

Compounds of Formula (I) which represent a 5-pyridin-2-yl-[1,2,4]oxadiazole derivative, are prepared by reacting a compound of Structure 1 in a solvent such as xylene, toluene, benzene, pyridine, DMF, THF, dioxane, DME, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, $NEt_3$, etc.), tetraalkylammonium salts, or water removing agents (e.g. oxalyl chloride, a carboxylic acid anhydride, $POCl_3$, $PCl_5$, $P_4O_{10}$, molecular sieves, Burgess reagent, etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

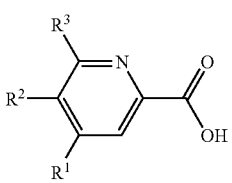

Structure 2

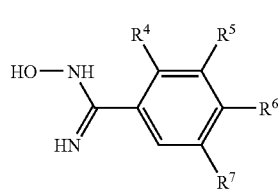

Structure 3

Compounds of Structure 1 may be prepared by reacting a compound of Structure 2 with a compound of Structure 3 in a solvent such as DMF, THF, DCM, etc. in the presence or absence of one or more coupling agents such as TBTU, DCC, EDC, HBTU, CDI, etc. and in the presence or absence of a base such as $NEt_3$, DIPEA, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

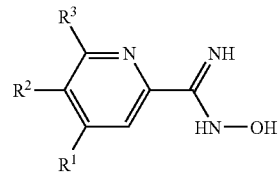

Structure 4

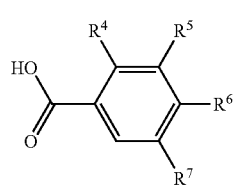

Structure 5

Compounds of Formula (I) which represent a 3-pyridin-2-yl-[1,2,4]oxadiazole derivative, are prepared in an analogous fashion (Lit.: e.g. C. T. Brain, J. M. Paul, Y. Loong, P. J. Oakley, *Tetrahedron Lett.* 40 (1999) 3275-3278) by reacting a compound of Structure 4 with a compound of Structure 5 and subsequent cyclisation of the corresponding hydroxyamidine ester intermediate.

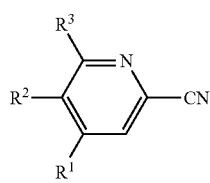

Structure 6

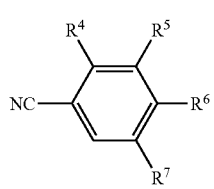

Structure 7

Compounds of Structure 3 and 4 may be prepared by reacting a compound of Structure 6 and 7, respectively, with hydroxylamine or one of its salts in a solvent such as MeOH, EtOH, pyridine, etc. in the presence or absence of a base such as $Na_2CO_3$, $K_2CO_3$, potassium tert.butylate, $NEt_3$, etc. (Lit.: e.g. E. Meyer, A. C. Joussef, H. Gallardo, *Synthesis* 2003, 899-905; WO 2004/035538 (Merck & Co., Inc., USA)).

Depending on the nature of the functionalities present in the residues $R^4$ to $R^7$ in Structures 3, 5 and 7, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^4$ to $R^7$, in particular $R^6$, may also be introduced in later steps that follow the coupling of the pyridine compounds of Structure 2 or 4 with the phenyl derivatives of Structure 3 or 5, respectively, by using a suitable precursor of a compound of Structure 3 or 5. The phenyl compounds of Structure 3 and 5 or their precursors are either commercially available or are prepared according to procedures known to a person skilled in the art.

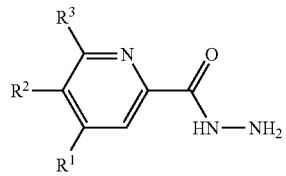

Structure 8

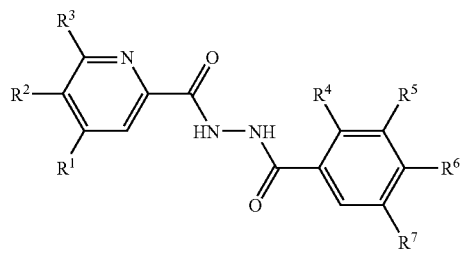

Structure 9

Compounds of Formula (I) which represent a 2-pyridin-2-yl-[1,3,4]oxadiazole derivative, are prepared similarly by reacting a compound of Structure 2 with hydrazine (by using a coupling reagent such as TBTU, DCC, EDC, HBTU, PyBOP, CDI, etc.) to form a compound of Structure 8 which is then coupled with a compound of Structure 5 to give a compound of Structure 9. A compound of Structure 9 can also be prepared by following the reverse reaction order i.e. by first coupling a compound of Structure 5 with hydrazine followed by reacting the corresponding hydrazide intermediate with a compound of Structure 2. Dehydration of a compound of Structure 9 to form the desired 2-pyridin-2-yl-[1,3,4]oxadiazole derivative is affected by treating a compound of Structure 9 with a reagent such as $POCl_3$; $CCl_4$ and $CBr_4$ in combination with $PPh_3$; $P_2O_5$; Burgess reagent; etc. in a solvent such as toluene, MeCN, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278).

Alternatively, the bonds between the pyridine or the phenyl ring and the central oxadiazole ring can also be formed by applying palladium catalysed cross coupling reactions.

Methods that effect the transformation of a compound of Structure 2 or 5 into a compound of Structure 6 or 7, respectively, or the opposite, are known to a person skilled in the art.

Compounds of Structure 2, wherein $R^1$ represents methyl, ethyl or methoxy, $R^2$ represents hydrogen and $R^3$ represents $C_{2-5}$-alkyl (Structure 13), may be prepared following the reaction sequence outlined below:

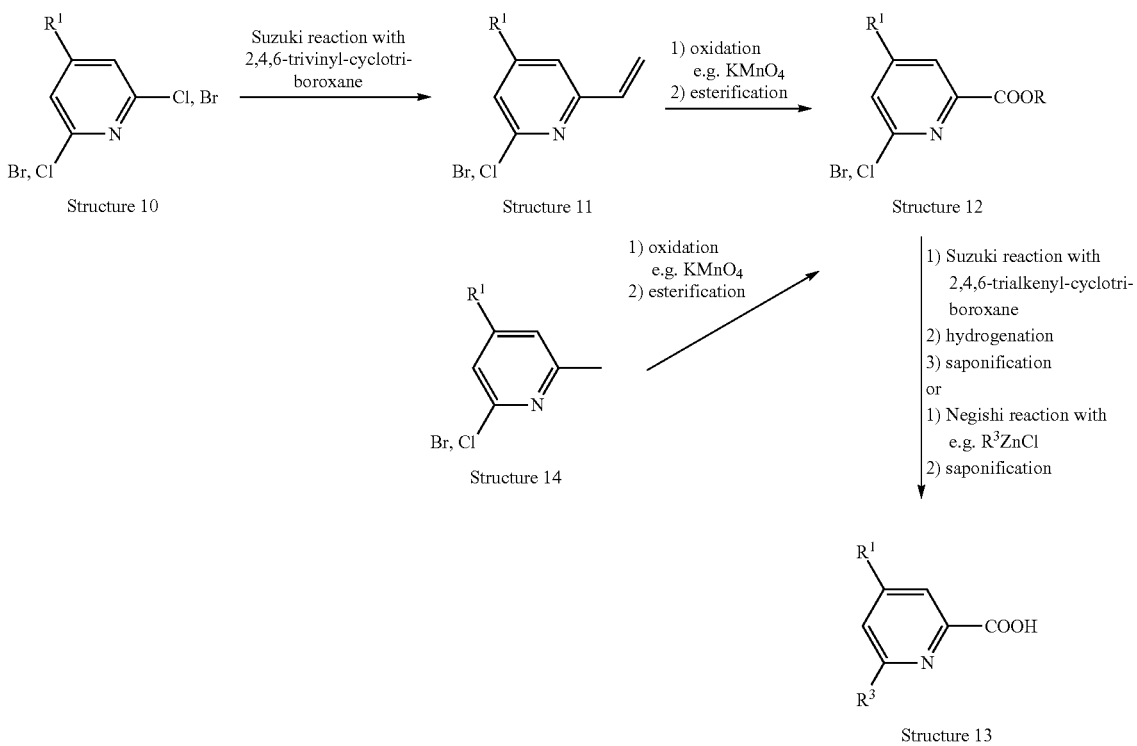

The picolinic acid of Structure 13 may be prepared by treating a compound of Structure 10 (either commercially available or prepared in analogy to literature procedures e.g. T. Kaminski, P. Gros, Y. Fort, *Eur. J. Org. Chem.* 19 (2003) 3855-3860; U. Ziener, E. Breuning, J.-M. Lehn, E. Wegelius, K. Rissanen, G. Baum, D. Fenske, G. Vaughan, *Chemistry—A European Journal* 6 (2000) 4132-4139; R.-A. Fallahpour, *Synthesis* 2000 1665-1667; B. G. Szczepankiewicz, et al. *J. Med. Chem.* 49 (2006) 3563-3580) with 2,4,6-trivinyl-cyclotriboroxane under Suzuki conditions to form a compound of Structure 11 which is oxidised and esterified to the picolinic acid of Structure 12 (R represents e.g. methyl, ethyl, isopropyl, tert.-butyl, etc). Oxidation followed by esterification of a commercially available compound of Structure 14 may also give access to a compound of Structure 12. The compound of Structure 12 is then either subjected to Suzuki cross coupling conditions using the appropriate 2,4,6-trialkenyl-cyclotriboroxane (prepared according to F. Kerins, D. F. O'Shea, *J. Org. Chem.* 67 (2002) 4968-4971), hydrogenated and saponified, or treated with the appropriate alkyl-Zn-reagent under Negishi conditions (Lit.: e.g. H. Matsushita, E. Negishi, *J. Org. Chem.* 47 (1982) 4161-4165) prior to saponification to furnish the desired compound of Structure 13.

Compounds of Structure 2, wherein $R^1$ represents methyl, ethyl or methoxy, $R^2$ represents hydrogen and $R^3$ represents $C_{1-4}$-alkoxy (Structure 17), may be prepared following the reaction sequence outlined below:

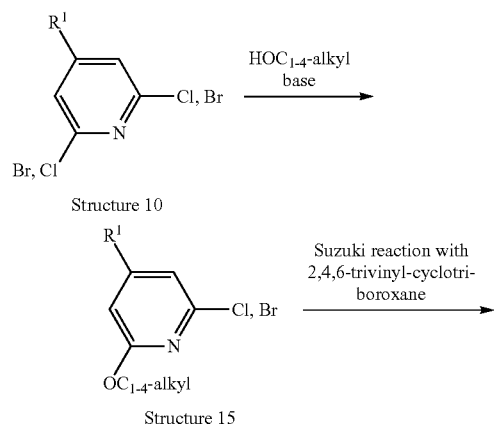

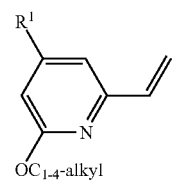

Structure 16 oxidation
e.g. KMnO$_4$

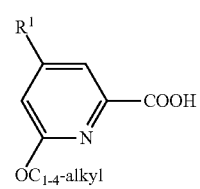

Structure 17

A compound of Structure 10 is treated with the appropriate alcohol in the presence of a base, preferably the sodium or potassium salt of the alcohol, at temperatures between 0 and 80° C. (Lit.: e.g. C. Burstein, C. W. Lehmann, F. Glorius, *Tetrahedron* 61 (2005), 6207-6217; T. Nguyen, M. A. Wicki, V. Snieckus, *J. Org. Chem.* 69 (2004), 7816-7821) to give a compound of Structure 15. Suzuki reaction of a compound of Structure 15 with 2,4,6-trivinyl-cyclotriboroxane gives access to a compound of Structure 16 which then can be oxidised e.g. with KMnO$_4$ in acetone to give the desired compound of Structure 17.

Compounds of Structure 2, wherein $R^1$ represents $C_{2-5}$-alkyl, $R^2$ represents hydrogen and $R^3$ represents methyl or ethyl (Structure 22), may be prepared following the reaction sequence outlined below:

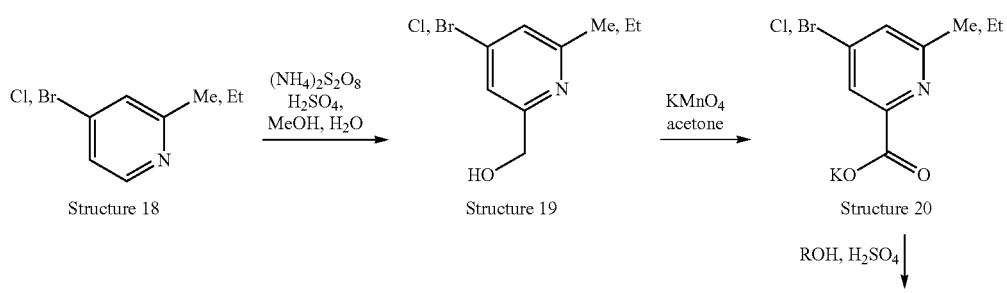

-continued

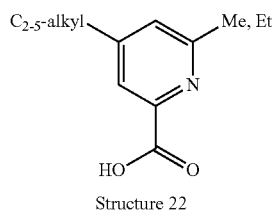

Structure 22

1) Suzuki reaction with
   2,4,6-trialkenyl-cyclotri-
   boroxane
2) hydrogenation
3) saponification
or
1) Negishi reaction with
   e.g. $C_{2-5}$-alkylZnCl
2) saponification

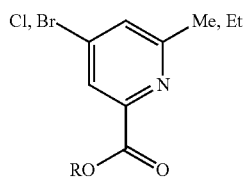

Structure 21

Thus, a compound of Structure 18 (either commercially available or prepared according to literature procedures e.g. J. P. Simeone et al., *Bioorg. Med. Chem. Letters* 12 (2002), 3329-3332; D. L. Comins, N. B. Mantlo, *J. Org. Chem.* 50 (1985), 4410-4411) is treated with $(NH_4)_2S_2O_8$ in a mixture of methnol, water and $H_2SO_4$ at elevated temperatures (Minisci reaction Lit.: e.g. R. B. Katz, J. Mistry, M. B. Mitchell, *Synth. Commun.* 19 (1989) 317-325; M. A. A. Biyouki, R. A. J. Smith, J. J. Bedford, J. P. Leader, *Synth. Commun.* 28 (1998) 3817-3825), to form a compound of Structure 19. This compound can be oxidised to a compound of Structure 20 using e.g. $KMnO_4$ in acetone. By treating a compound of Structure 20 with an alcohol such as methanol, ethanol, isopropanol in the presence of an acid such as $H_2SO_4$ or HCl, the corresponding compound of Structure 21 (R represents e.g. methyl, ethyl, or isopropyl) can be produced. The compound of Structure 21 is then either subjected to Suzuki cross coupling conditions using the appropriate 2,4,6-trialkenyl-cyclotriboroxane, hydrogenated and saponified, or treated with the appropriate alkyl-Zn-reagent under Negishi conditions prior to saponification to furnish the desired compound of Structure 22.

Compounds of Structure 2, wherein $R^1$ represents $C_{1-4}$-alkoxy, $R^2$ represents hydrogen and $R^3$ represents methyl or ethyl (Structure 26), may be prepared following the reaction sequence outlined below:

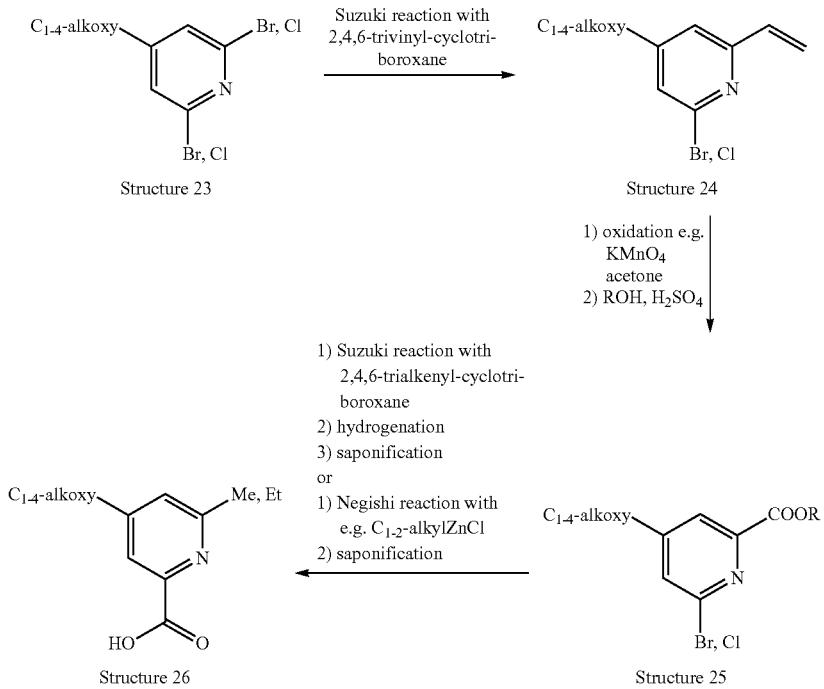

Hence, a compound of Structure 23 (e.g. prepared according to literature procedures given in B. G. Szczepankiewicz et al., *J. Med. Chem.* 49 (2006) 3563-3580; M. Inouye, M. Waki, H. Abe, *J. Am. Chem. Soc.* 126 (2004), 2022-2027) is reacted with 2,4,6-trivinylcyclotriboroxane to give a compound of Structure 24. Oxidation using e.g. $KMnO_4$ in acetone of a compound of Structure 24 followed by esterification furnishes a compound of Structure 25 (R=methyl, ethyl, isopropyl, tert.butyl, etc.). The compounds of Structure 25 is then either subjected to Suzuki cross coupling conditions using again 2,4,6-trivinyl-cyclotriboroxane, hydrogenated and saponified, or treated with a methyl- or ethyl-Zn-reagent under Negishi conditions prior to saponification to furnish the desired compound of Structure 26.

Compounds of Structure 2, wherein R¹ represents methyl or ethyl, R² represents $C_{3-5}$-alkyl, and R³ represents hydrogen (Structure 31), may be prepared following the reaction sequence outlined below:

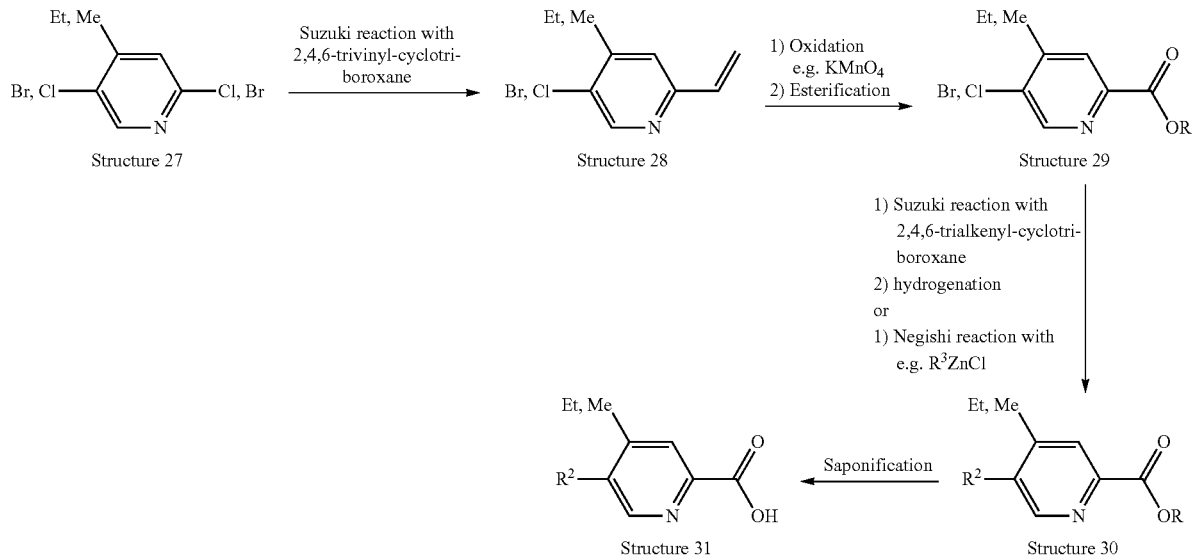

Thus, a compound of Structure 27 (commercially available or may be prepared in analogy to literature procedures, e.g. P. Pierrat, P. Gros, Y. Fort, *Synlett* 2004, 2319-2322) is reacted with 2,4,6-trivinyl-cyclotriboroxane under Suzuki conditions to form a compound of Structure 28, which is oxidised and esterified to a compound of Structure 29 (wherein R is $C_{1-4}$-alkyl). Suzuki reaction with the appropriate 2,4,6-trialkenyl-cyclotriboroxane, hydrogenation and saponification or Negishi reaction with the appropriate alkyl-Zn-reagent followed by saponification of a compound of Structure 30 furnish the compounds of Structure 31.

Compounds of Structure 2, wherein R¹ represents methoxy, R² represents $C_{3-5}$-alkyl, and R³ represents hydrogen (Structure 32), may be prepared following the reaction sequence outlined below:

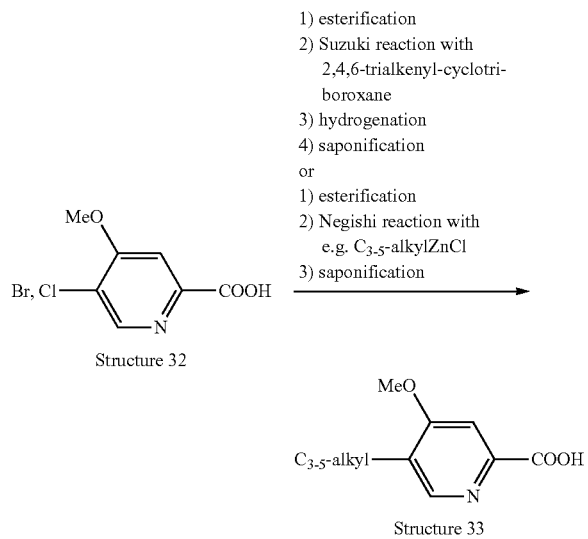

By applying the reaction sequence of either esterification, Suzuki reaction, hydrogenation, saponification or esterification, Negishi reaction and saponification, a commercially available compound of Structure 32 may be transformed into a compound of Structure 33. The compounds of Structure 32 may be prepared, for instance, by reacting 4,5-dichloro-picolinic acid with water in their presence of an acid (Lit.: e.g. *J. Prakt. Chem.;* 27 (1883), 293) to give 4-chloro-5-hydroxy-picolinic acid. This compound may then be alkylated in analogy to literature procedures (T. Vermonden; D. Branowska; A. T. M. Marcelis; E. J. R. Sudholter; *Tetrahedron* 59 (2003), 5039-5045) to give 4-chloro-5-methoxy picolinic acid methyl ester which can be hydrolysed under acidic or basic conditions to the desired compound of Structure 32.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine or diethylamine) and eluent B (hexane), at a flow rate of 0.8 to 150 mL/min.

Experimental Part

The following examples illustrate the invention but do not at all limit the scope thereof.

All temperatures are stated in °C. Compounds are characterized by ¹H-NMR (300 MHz) or ¹³C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% MeCN in water, 1 min, with 0.04% trifluoroacetic acid, flow: 4.5 mL/min), $t_R$ is given in min, (retention times marked with * or as LC-MS* refer to LC run under basic conditions, i.e. eluting with a gradient of MeCN in water containing 13 mM of ammonium hydroxide, otherwise identical conditions; retention times or LC-MS marked with ** refer to a LC run under the following conditions: column: Zorbax Extended C18, 1.8 µM, 4.6×20 mm, gradient: 5-95% MeCN in water, 1 min, with 0.04% TFA, flow: 4.5 mL/min); by TLC (TLC-plates from Merck, Silica gel 60 $F_{254}$); or by melting point. Compounds are purified by preparative HPLC (column: X-terra RP18, 50×19 mm, 5 µm gradient: 10-95% MeCN in water containing 0.5% of formic acid) or by MPLC (Labomatic MD-80-100 pump, Linear UVIS-201 detector, column: 350×18 mm, Labogel-RP-18-5s-100, gradient: 10% MeOH in water to 100% MeOH).

Abbreviations (as Used Hereinbefore and Hereinafter):
aq. aqueous
BOC tert-butoxycarbonyl
BSA bovine serum albumin
Bu butyl
Burgess reagent methoxycarbonylsulfamoyl triethylammonium hydroxide
CC column chromatography
CDI carbonyl diimidazole
DCC dicyclohexyl carbodiimide
DCM dichloromethane
DEAD diethyl-diazodicarboxylate
DIPEA Wining's base, diethylisopropylamine
DME 1,2-dimethoxyethane
DMF dimethylformamide
DMSO dimethylsulfoxide
dppf 1,1'-bis(diphenylphosphino-κP)ferrocene
DPPP 1,3-bis-(diphenylphosphino)-propane
EA ethyl acetate
EDC N-(3-dimethylaminopropyl)-N'-ethyl-carbodiimide
Et ethyl
EtOH ethanol
FC flash chromatography
h hour(s)
HBTU O-(benzotriazol-1-yl)-N,N,N',N'-tetramethyluronium hexafluorophosphate
HOBt 1-hydroxy-benzotriazole
HPLC high performance liquid chromatography
HV high vacuum conditions
LC-MS liquid chromatography-mass spectrometry
Lit. literature
MeCN acetonitrile
Me methyl
MeOH methanol
min minute(s)
MPLC medium pressure liquid chromatography
NaOAc sodium acetate
$NEt_3$ triethylamine
OAc acetate
org. organic
Ph phenyl
PyBOP benzotriazol-1-yl-oxy-tris-pyrrolidino-phosphonium-hexafluoro-phosphate
prep. preparative
rt room temperature
sat. saturated
S1P sphingosine 1-phosphate
TBME tert.-butyl methyl ether
TBTU 2-(1H-benzotriazole-1-yl)-1,2,3,3-tetramethyluronium tetrafluoroborate
TFA trifluoroacetic acid
THF tetrahydrofuran
TLC thin layer chromatography
$t_R$ retention time 5-Isobutyl-4-methyl-pyridine-2-carboxylic acid (hydrochloride)

a) To a solution of 2,5-dibromo-4-picoline (9.00 g, 35.9 mmol) in DME (96 mL), 2,4,6-trivinyl-cyclotriboroxane pyridine complex (8.63 g, 35.9 mmol) and 2 N aq. $K_2CO_3$-solution (36 mL) is added. The mixture is degassed and put under argon before Pd(PPh$_3$)$_4$ (746 mg, 0.646 mmol) is added. The mixture is stirred at 80° C. for 15 h, before it is cooled to rt, diluted with diethyl ether (50 mL), washed with sat. aq. NaHCO$_3$-solution (2×30 mL), dried over MgSO$_4$, filtered and concentrated. The crude product is purified by CC on silica gel eluting with heptane:EA 9:1 to give 5-bromo-4-methyl-2-vinyl-pyridine (7.04 g) as a yellow oil; LC-MS: $t_R$=0.75 min; [M+1]$^+$=198.22; $^1$H NMR (CDCl$_3$): δ 2.41 (s, 3H), 5.50 (d, J=10.8 Hz, 1H), 6.21 (d, J=17.3 Hz, 1H), 6.74 (dd, J=17.3, 10.8 Hz, 1H), 7.22 (s, 1H), 8.59 (s, 1H).

b) To a solution of 5-bromo-4-methyl-2-vinyl-pyridine (7.04 g, 35.5 mmol) in acetone (280 mL) and water (280 mL), KMnO$_4$ (28.81 g, 71.1 mmol) is added. The dark mixture is stirred at rt for 3 days before it is filtered over a glass-filter pad. The colourless filtrate is evaporated to give crude 5-bromo-4-methyl-pyridine-2-carboxylic acid (10.9 g, as potassium salt) as a white solid; LC-MS: $t_R$=0.64 min, [M+1]$^+$=215.90.

c) To a suspension of crude 5-bromo-4-methyl-pyridine-2-carboxylic acid (10.9 g, approximately 35.5 mmol) in ethanol (120 mL), $H_2SO_4$ (0.5 mL) is added. The mixture is stirred at 70° C. for 18 h. The pH of the clear solution is adjusted to pH 9 by adding sat. aq. NaHCO$_3$-solution and the mixture was extracted with diethyl ether (3×300 mL). The combined org. extracts are dried over MgSO$_4$, filtered and concentrated to give 5-bromo-4-methyl-pyridine-2-carboxylic acid ethyl ester (8.20 g) as a green oil; LC-MS: $t_R$=0.87 min, [M+1]$^+$=243.91.

d) To a solution of 5-bromo-4-methyl-pyridine-2-carboxylic acid ethyl ester (4.03 g, 16.5 mmol) in DME (43 mL), 2,4,6-tri-(2-methyl-propenyl)-cycloboroxane pyridine complex (5.36 g, 16.5 mmol) followed by 2 N aq. $K_2CO_3$-solution (16 mL) is added. The mixture is degassed and put under argon before Pd(PPh$_3$)$_4$ (343 mg, 0.297 mmol) is added. The mixture is stirred at 80° C. for 6 h before it is cooled to rt, diluted with diethyl ether (50 mL), washed with sat. aq. NaHCO$_3$-solution (3×30 mL), dried over MgSO$_4$, filtered and concentrated. The crude product is purified by CC on silica gel eluting with heptane:EA 7:3 to give 4-methyl-5-(2-methyl-propenyl)-pyridine-2-carboxylic acid ethyl ester (1.33 g) as a yellow oil; LC-MS: $t_R$=0.87 min, [M+1]$^+$=220.08.

e) To a solution of 4-methyl-5-(2-methyl-propenyl)-pyridine-2-carboxylic acid ethyl ester (1.33 g, 6.06 mmol) in THF (10 mL) and ethanol (10 mL), Pd/C (300 mg, 10% Pd) is carefully added. The slurry is stirred at rt for 15 h under 2 bar of $H_2$. The catalyst is filtered off and the filtrate is concentrated and dried to give 5-isobutyl-4-methyl-pyridine-2-carboxylic acid ethyl ester (1.27 g) as a colourless oil; LC-MS: $t_R$=0.86 min, [M+1]$^+$=222.10.

f) A solution of 5-isobutyl-4-methyl-pyridine-2-carboxylic acid ethyl ester (1.27 g, 5.76 mmol) in 6 N aq. HCl (110 mL) is stirred at 65° C. for 48 h before the solvent is evaporated in vacuo. The remaining residue is suspended in DCM and filtered. The solid material is washed with additional DCM and dried under HV to give 5-isobutyl-4-methyl-pyridine-2-carboxylic acid hydrochloride (1.05 g) as a white solid; LC-MS: $t_R$=0.59 min; [M+1]$^+$=194.28; $^1$H NMR (D$_6$-DMSO): δ 0.90 (d, J=6.3 Hz, 6H), 1.85-1.96 (m, 1H), 2.69 (d, J=7.0 Hz, 2H), 8.18 (s, 1H), 8.58 (s, 1H), 11.80 (s br, 1H).

6-Isobutyl-4-methyl-pyridine-2-carboxylic acid (hydrochloride)

a) A solution of n-BuLi (21.1 mL, 33.8 mmol, 1.6 M) in THF was cooled to −78° C. before a solution of 2,6-dichloropyridine (5.0 g, 33.8 mmol) in THF (36 mL) is added dropwise over a period of 20 min. The reaction mixture is stirred at −78° C. for 30 min, and then iodomethane (4.79 g, 33.8 mmol) is added. The mixture is stirred for 30 min before it is quenched with sat. aq. NH$_4$Cl solution at −78° C. The mixture is extracted with diethyl ether, the org. extract is dried over MgSO$_4$, filtered and concentrated. The crude product is purified by CC on silica gel eluting with heptane:EA 19:1 to give 2,6-dichloro-4-methyl-pyridine (2.34 g) as a colourless oil containing the regio isomer 2,6-dichloro-3-methyl-pyridine; LC-MS: $t_R$=0.89 min, [M+1]$^+$=161.97.

b) To a solution of 2,6-dichloro-4-methyl-pyridine (2.34 g, 14.4 mmol) and 2,4,6-trivinyl-cyclotriboroxane pyridine complex (1.75 g, 7.26 mmol) in DME (27 mL), 2 M aq. K$_2$CO$_3$ solution (10 mL) is added. The mixture is degassed and put under argon before Pd(PPh$_3$)$_4$ (300 mg, 0.26 mmol) is added. The mixture is stirred at 80° C. for 3 h before it is cooled to rt, diluted with diethyl ether and washed with sat. aq. NaHCO$_3$ solution. The org. extract is dried over MgSO$_4$, filtered and concentrated. The crude product is purified by CC on silica gel eluting with heptane:EA 9:1. The thus obtained product is dissolved in EA, repeatedly washed with 5% aq. citric acid solution, dried over MgSO$_4$, filtered and evaporated to give 6-chloro-4-methyl-2-vinyl-pyridine (1.24 g) as a colourless oil; LC-MS: $t_R$=0.90 min, [M+1]$^+$=154.03.

c) To a solution of 6-chloro-4-methyl-2-vinyl-pyridine (1.24 g, 8.06 mmol) in water (50 mL) and acetone (50 mL), KMnO$_4$ (6.53 g, 41.3 mmol) is added. The dark mixture becomes warm (40° C.) and is stirred at rt for 3 h before it is filtered over a sintered glass filter. The solvent of the colourless filtrate is evaporated to give crude 6-chloro-4-methyl-pyridine-2-carboxylic acid potassium salt (3.2 g) as a colourless solid; LC-MS: $t_R$=67 min, [M+1]$^+$=171.99. This material is suspended in ethanol (150 mL) and H$_2$SO$_4$ (2 mL) is added until a clear solution forms. The mixture is heated to 70° C. for 18 h. The mixture is carefully diluted with sat. aq. NaHCO$_3$ solution until a pH of 9 is reached. The mixture is extracted three times with EA. The combined org. extracts are dried over MgSO$_4$, filtered and concentrated. The crude product is purified by CC on silica gel eluting with heptane:EA 3:2 to give ethyl 6-chloro-4-methyl-pyridine-2-carboxylate (500 mg) as a pale yellow oil; LC-MS: $t_R$=0.87 min; [M+1]$^+$=200.04; $^1$H NMR (CDCl$_3$): δ 1.45 (t, J=7.3 Hz, 3H), 2.45 (s, 3H), 4.48 (q, J=6.8 Hz, 2H), 7.35 (s, 1H), 7.89 (s, 1H).

d) To a solution of ethyl 6-chloro-4-methyl-pyridine-2-carboxylate (500 mg, 2.51 mmol) and 2,4,6-tris-(2-methyl-propenyl)-cyclotriboroxane pyridine complex (814 mg, 2.51 mmol) in DME (32 mL), 2 M aq. K$_2$CO$_3$ (12 mL) solution is added. The mixture is degassed and put under argon before Pd(PPh$_3$)$_4$ (52 mg, 0.045 mmol) is added. The mixture is stirred at 80° C. for 6 h before it is cooled to rt, diluted with diethyl ether (50 mL) and washed with sat. aq. NaHCO$_3$ (2×30 mL) solution. The org. extract is dried over MgSO$_4$, filtered and concentrated. The crude product is purified by CC on silica gel eluting with heptane:EA 9:1 to give 4-methyl-6-(2-methyl-propenyl)-pyridine-2-carboxylic acid ethyl ester (176 mg) as a yellow oil; $^1$H NMR (CDCl$_3$): δ 1.45 (t, J=7.0 Hz, 3H), 1.97 (s, 3H), 2.12 (s, 3H), 2.42 (s, 3H), 4.46 (q, J=7.0 Hz, 2H), 6.41 (s, 1H), 7.17 (s, 1H), 7.75 (s, 1H).

e) To a solution of 4-methyl-6-(2-methyl-propenyl)-pyridine-2-carboxylic acid ethyl ester (175 mg, 0.80 mmol) in THF (5 mL) and ethanol (5 mL), Pd/C (50 mg, 10% Pd) is added. The mixture is stirred at 50° C. for 15 h under 1 bar of H$_2$. The catalyst is filtered off over celite and the solvent of the filtrate is evaporated to give 6-isobutyl-4-methyl-pyridine-2-carboxylic acid ethyl ester (174 mg) as a colourless oil; LC-MS: $t_R$=0.84 min, [M+1]$^+$=222.48.

f) A solution of 6-isobutyl-4-methyl-pyridine-2-carboxylic acid ethyl ester (174 mg, 0.78 mmol) in 6 N aq. HCl (20 mL) is stirred at 65° C. for 18 h. The solvent is evaporated and the remaining residue is dried under HV to give 6-isobutyl-4-methyl-pyridine-2-carboxylic acid hydrochloride as green oil; LC-MS: $t_R$=0.58 min, [M+1]$^+$=194.09.

6-(1-Ethyl-propyl)-4-methyl-pyridine-2-carboxylic acid a) Methyl 6-chloro-4-methyl-pyridine-2-carboxylate is prepared in analogy to ethyl 6-chloro-4-methyl-pyridine-2-carboxylate; LC-MS**: $t_R$=0.49 min, [M+1]$^+$=186.25; $^1$H NMR (CDCl$_3$): δ 2.46 (s, 3H), 4.02 (s, 3H), 7.37 (s, 1H), 7.92 (s, 1H).

b) Methyl 6-chloro-4-methyl-pyridine-2-carboxylate (500 mg, 2.69 mmol) is treated with 1-ethyl-propyl zinkbromide and saponified as described for 6-(1-ethyl-propyl)-4-methoxy-pyridine-2-carboxylic acid to give the title compound (220 mg) as a pale yellow oil; LC-MS**: $t_R$=0.37 min, [M+1]$^+$=208.29; $^1$H NMR (CDCl$_3$): δ 0.80 (t, J=7.3 Hz, 6H), 1.69-1.81 (m, 4H), 2.48 (s, 3H), 2.58-2.67 (m, 1H), 7.21 (s, 1H), 7.91 (s, 1H).

4-Isobutyl-6-methyl-pyridine-2-carboxylic acid (hydrochloride)

a) To a solution of 4-bromo-2-methyl-pyridine (5.70 g, 32.14 mmol) in methanol (100 mL), H$_2$SO$_4$ (0.3 mL) is added. The mixture is heated to reflux before a solution of ammonium peroxydisulfate (7.33 g, 32.14 mmol) in water (53 mL) is carefully added. The mixture is stirred at reflux for 2 h before two more portions of ammonium peroxydisulfate (2×7.33 g) are added as a sat. aq. solution. Stirring is continued at reflux for 3 h. Methanol is removed under reduced pressure and the remaining solution is diluted with sat. aq. NaHCO$_3$ solution and extracted with EA. The org. extract is dried over MgSO$_4$, filtered and concentrated. The crude product is purified by CC on silica gel eluting with heptane:EA 3:7 to give (4-bromo-6-methyl-pyridin-2-yl)-methanol (1.31 g) as pale yellow solid; LC-MS: $t_R$=0.31 min; [M+1]$^+$=201.96; $^1$H NMR (CDCl$_3$): δ 2.55 (s, 3H), 3.59 (s br, 1H), 4.72 (s br, 2H), 7.28 (s, 2H).

b) To a solution of (4-bromo-6-methyl-pyridin-2-yl)-methanol (1.31 g, 6.48 mmol) in acetone (150 mL), KMnO$_4$ (2.61 g, 16.5 mmol) is added. The mixture is stirred at 40° C. for 2 h before it is filtered over a sintered glass funnel. The filtrate is evaporated to dryness, and the remaining solid is washed with water and dried under HV to give 4-bromo-6-methyl-pyridine-2-carboxylic acid potassium salt (1.91 g) as a white solid; LC-MS: $t_R$=0.45 min, [M+1]$^+$=217.89.

c) To a suspension of 4-bromo-6-methyl-pyridine-2-carboxylic acid potassium salt (253 mg, 0.996 mmol) in ethanol (100 mL), H$_2$SO$_4$ (2 mL) is added dropwise. The mixture is heated to 70° C. for 16 h before it is carefully diluted with sat. aq. NaHCO$_3$. The mixture is extracted three times with diethyl ether. The combined org. extracts are dried over MgSO$_4$, filtered and concentrated. The crude product is purified on prep. TLC plates with heptane:EA 3:2 to give 4-bromo-6-methyl-pyridine-2-carboxylic acid ethyl ester (105 mg) as a pale yellow oil; LC-MS: $t_R$=0.85 min, [M+1]$^+$=244.22.

d) 4-Isobutyl-6-methyl-pyridine-2-carboxylic acid hydrochloride is prepared starting from 4-bromo-6-methyl-pyridine-2-carboxylic acid ethyl ester following the procedures given in steps d) to f) for the preparation of 6-isobutyl-4-methyl-pyridine-2-carboxylic acid; LC-MS: $t_R$=0.58 min;

[M+1]⁺=194.08; ¹H NMR (CDCl₃): δ 1.01 (d, J=6.3 Hz, 6H), 2.04-2.16 (m, 1H), 2.80 (d, J=7.0 Hz, 2H), 3.09 (s, 3H), 7.56 (s, 1H), 8.04 (s, 1H), 9.74 (s br, ~1H).

6-Isobutyl-4-methoxy-pyridine-2-carboxylic acid (hydrochloride)

a) To a stirred solution of 6-chloro-4-methoxypyridine-2-carboxylic acid (5.00 g, 26.7 mmol) in ethanol (75 mL), chlorotrimethylsilane (15 mL) is added. The reaction mixture is stirred at rt for 16 h before the solvent is evaporated. The remaining residue is dried under vacuum to give 6-chloro-4-methoxy-2-carboxylic acid ethyl ester (5.95 g) as a pale yellow oil; LC-MS: $t_R$=0.85 min; [M+1]⁺=215.97; ¹H NMR (CDCl₃): δ 1.44 (t, J=7.0 Hz, 3H), 3.94 (s, 3H), 4.48 (q, J=7.0 Hz, 2H), 7.01 (d, J=2.0 Hz, 1H), 7.61 (d, J=2.0 Hz, 1H).

b) The title compound is prepared from 6-chloro-4-methoxy-2-carboxylic acid ethyl ester following the procedures in steps d) to f) of the preparation of 6-isobutyl-4-methyl-pyridine-2-carboxylic acid; LC-MS: $t_R$=0.51 min; [M+1]⁺=210.31; ¹H NMR (CDCl₃): δ 1.04 (d, J=6.5 Hz, 6H), 2.21-2.32 (m, 1H), 3.27 (d, J=7.0 Hz, 2H), 4.20 (s, 3H), 7.12 (s, 1H), 7.83 (s, 1H).

6-(1-Ethyl-propyl)-4-methoxy-pyridine-2-carboxylic acid a) 6-Chloro-4-methoxy-2-carboxylic acid methyl ester (1.89 g) is prepared in analogy to 6-chloro-4-methoxy-2-carboxylic acid ethyl ester starting from 6-chloro-4-methoxy-pyridine-2-carboxylic acid (2.00 g; 10.7 mmol); LC-MS**: $t_R$=0.48 min; [M+1]⁺=202.23; ¹H NMR (CDCl₃): δ3.95 (s, 3H), 4.01 (s, 3H), 7.03 (d, J=2.3 Hz, 1H), 7.63 (d, J=2.3 Hz, 1H).

b) A solution of 6-chloro-4-methoxy-2-carboxylic acid methyl ester (2.63 g, 13.0 mmol) in dioxane (150 mL) is degassed and put under argon before Pd(dppf) (109 mg, 133 μmol) is added. To this mixture, 1-ethyl-propyl zink bromide (50 mL of a 0.5 M solution in THF, 25.0 mmol) is added dropwise. The mixture is stirred at 76° C. for 15 h. The mixture is cooled to rt, diluted with water and extracted twice with EA. The combined org. extracts are dried over MgSO₄, filtered and concentrated. The crude product is purified by MPLC on silica gel eluting with a gradient of EA in heptane to give 6-(1-ethyl-propyl)-4-methoxy-pyridine-2-carboxylic acid methyl ester (450 mg) as a pale yellow oil; LC-MS**: $t_R$=0.46 min; [M+1]⁺=238.34.

c) A solution of 6-(1-ethyl-propyl)-4-methoxy-pyridine-2-carboxylic acid methyl ester (450 mg, 1.90 mmol) in 25% aq. HCl is stirred at 65° C. for 18 h. The mixture is concentrated and dried to give the title compound (592 mg) as hydrochloride salt; LC-MS**: $t_R$=0.38 min; [M+1]⁺=224.32.

N-Hydroxy-5-isobutyl-4-methyl-pyridine-2-carboxamidine a) A solution of 5-isobutyl-4-methyl-pyridine-2-carboxylic acid isopropyl ester (655 mg, 2.78 mmol, prepared in analogy to the corresponding ethyl ester) in 7 N NH₃ in methanol (40 mL) is stirred in a sealed vial at 75° C. for 72 h. The solvent is removed in vacuo and the residue is dissolved again in 7 N NH₃ in methanol. The resulting solution is again stirred at 75° C. for 24 h. The solvent is evaporated to give crude 5-isobutyl-4-methyl-pyridine-2-carboxylic amide (535 mg); LC-MS: $t_R$=0.80 min; [M+1]⁺=193.01. This material is dissolved in DCM (20 mL) and pyridine (1.08 g, 11.13 mmol) is added. The mixture is stirred at rt for 5 min before trifluoroacetic acid anhydride (1.75 g, 1.18 mmol) is added dropwise. The mixture is stirred at rt for 16 h. The mixture is diluted with DCM (100 mL), washed with sat. aq. NaHCO₃ solution (3×50 mL) and brine (50 mL). The org. extract is dried over Na₂SO₄, filtered and concentrated. The crude product is purified by MPLC on silica gel eluting with a gradient of EA in heptane to give 5-isobutyl-4-methyl-pyridine-2-carbonitrile (106 mg) as a pale yellow oil; LC-MS: $t_R$=0.96 min; [M+1]⁺=175.03.

b) To a solution of 5-isobutyl-4-methyl-pyridine-2-carbonitrile (106 mg, 608 μmol) in methanol (3 mL), triethylamine (123 mg, 1.22 mmol) and hydroxylamine hydrochloride (63 mg, 913 μmol) is added. The mixture is stirred at 75° C. for 18 h before it is concentrated. The residue is dissolved in aq. NaHCO₃ (pH 7-8) and extracted with DCM (6×50 mL). The org. extracts are combined, dried over MgSO₄, filtered, concentrated and dried to give the title compound (155 mg) as a white solid; LC-MS: $t_R$=0.67 min, [M+1]⁺=208.01; ¹H NMR (CD₃OD): δ0.97 (d, J=6.8 Hz, 6H), 1.84-1.96 (m, 1H), 2.37 (s, 3H), 2.58 (d, J=7.3 Hz, 2H), 7.67 (s, 1H), 8.26 (s, 1H).

3-Ethyl-4-hydroxy-5-methyl-benzonitrile

The title compound is prepared from 3-ethyl-4-hydroxy-5-methyl-benzaldehyde following literature procedures (A. K. Chakraborti, G. Kaur, Tetrahedron 55 (1999) 13265-13268); LC-MS: $t_R$=0.90 min; ¹H NMR (CDCl₃): δ1.24 (t, J=7.6 Hz, 3H), 2.26 (s, 3H), 2.63 (q, J=7.6 Hz, 2H), 5.19 (s, 1H), 7.30 (s, 2H).

3-Chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile); LC-MS: $t_R$=0.85 min. ¹H NMR (CDCl₃): δ2.33 (s, 3H), 6.10 (s, 1H), 7.38 (s, 1H), 7.53 (d, J=1.8 Hz, 1H).

4-Hydroxy-3-methoxy-5-methyl-benzonitrile

The title compound is prepared from commercially available 2-hydroxy-3-methoxy-toluene in analogy to literature procedures (see 3-ethyl-4-hydroxy-5-methyl-benzonitrile); LC-MS: $t_R$=0.84 min. ¹H NMR (CDCl₃): δ2.27 (s, 3H), 3.93 (s, 3H), 6.24 (s, 1H), 6.97 (d, J=1.3 Hz, 1H), 7.12 (s, 1H).

3-Chloro-4-hydroxy-5-methoxy-benzonitrile

The title compound is prepared from commercially available 3-chloro-4-hydroxy-5-methoxy-benzaldehyde in analogy to literature procedures (see 3-ethyl-4-hydroxy-5-methyl-benzonitrile); LC-MS: $t_R$=0.82 min; ¹H NMR (CDCl₃): δ3.98 (s, 3H), 6.36 (s, 1H), 7.04 (s, 1H), 7.34 (s, 1H).

4-Hydroxy-2-methoxy-benzonitrile

The title compound is prepared from commercially available 4-hydroxy-2-methoxy-benzaldehyde in analogy to literature procedures (see 3-ethyl-4-hydroxy-5-methyl-benzonitrile); LC-MS: $t_R$=0.74 min. ¹H NMR (D₆-DMSO): δ3.84 (s, 3H), 6.47 (d, J=8.5 Hz, 1H), 6.54 (s, 1H), 7.49 (d, J=8.5 Hz, 1H), 10.6 (s, 1H).

4,N-Dihydroxy-3,5-dimethyl-benzamidine

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR (CD$_3$OD): δ 7.20 (s, 2H), 2.20 (s, 6H).

3-Ethyl-4,N-dihydroxy-5-methyl-benzamidine

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4,N-Dihydroxy-3-methyl-5-propyl-benzamidine

The title compound is prepared from commercially available 2-methyl-6-propyl-phenol in analogy to literature procedures (e.g. B. Roth et al. *J. Med. Chem.* 31 (1988) 122-129; and literature cited for 3-ethyl-4,N-dihydroxy-5-methyl-benzamidine); LC-MS: $t_R$=0.54 min; [M+1]$^+$=209.43; $^1$H NMR (D$_6$-DMSO): δ0.90 (t, J=7.3 Hz, 3H), 1.48-1.59 (m, 3H), 2.19 (s, 3H), 2.56 (t, J=7.3 Hz, 2H), 7.37 (s, 1H), 7.40 (s, 1H), 9.34 (s, 1H).

3-Chloro-4,N-dihydroxy-5-methyl-benzamidine

The title compound is prepared from commercially available 2-chloro-6-methyl-phenol in analogy to literature procedures (e.g. B. Roth et al. *J. Med. Chem.* 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min; [M+1]$^+$=201.00; $^1$H NMR 82.24 (s, 2H), 2.35 (s, 4H), 5.98 (s br, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: $^1$H NMR (D$_6$-DMSO): δ2.21 (s, 3H), 5.72 (s br, 2H), 7.40 (s, 1H), 7.48 (s, 1H), 9.29 (s br, 1H), 9.48 (s br, 1H).

rac-4-(2,2-Dimethyl-[1,3]dioxolan-4-ylmethoxy)-N-hydroxy-3,5-dimethyl-benzamidine a) To a solution of 3,5-dimethyl-4-hydroxy-benzonitrile (5.0 g, 34.0 mmol) in THF (40 mL), rac-(2,2-dimethyl-[1,3] dioxolan-4-yl)-methanol (4.49 g, 34.0 mmol) followed by triphenylphosphine (13.4 g, 50.9 mmol) is added. The mixture is cooled with an ice-bath before DEAD (8.87 g, 50.9 mmol, 23.4 mL of a 40% solution in toluene) is added dropwise. The mixture is stirred at rt for 1 h, the solvent is removed in vacuo and the residue is purified by CC on silica gel eluting with heptane:EA 99:1 to 92:8 to give rac-4-(2,2-dimethyl-[1, 3]dioxolan-4-ylmethoxy)-3,5-dimethyl-benzonitrile (7.20 g) as a pale yellow oil; LC-MS: $t_R$=0.99 min, [M+1]$^+$=not detected.

b) To a solution of potassium tert.-butylate (6.18 g, 55.1 mmol) in methanol (125 mL), hydroxylamine hydrochloride (5.74 g, 82.7 mmol) is added. To this solution, a solution of rac-4-(2,2-dimethyl-[1,3]dioxolan-4-ylmethoxy)-3,5-dimethyl-benzonitrile (7.20 g, 27.6 mmol) in methanol (40 mL) is added. The mixture is refluxed for 72 h before the solvent is removed in vacuo. The residue is purified by prep. HPLC (XBridge Prep C18, 30×75 mm, 5 μm, 2-95% acetonitrile in water containing 0.5% sat. aq. NH$_3$) to give the title compound (4.85 g) as a pale yellow solid; LC-MS: $t_R$=0.67 min, [M+1]$^+$=295.06; $^1$H NMR (CDCl$_3$): δ 1.43 (s, 3H), 1.48 (s, 3H), 2.29 (s, 6H), 3.76-3.81 (m, 1H), 3.83-3.88 (m, 1H), 3.93-3.99 (m, 1H), 4.17-4.23 (m, 1H), 4.47-4.54 (m, 1H), 5.02 (s br, 1H), 7.28 (s, 2H).

(S)-4-(2,2-Dimethyl-[1,3]dioxolan-4-ylmethoxy)-N-hydroxy-3,5-dimethyl-benzamidine The title compound is prepared in analogy to rac-4-(2,2-dimethyl-[1,3]dioxolan-4-ylmethoxy)-N-hydroxy-3,5-dimethyl-benzamidine using (S)-(2,2-dimethyl-[1,3]dioxolan-4-yl)-methanol; LC-MS: $t_R$=0.67 min, [M+1]$^+$=295.01.

(R)-4-(2,2-Dimethyl-[1,3]dioxolan-4-ylmethoxy)-3-ethyl-N-hydroxy-5-methyl-benzamidine The title compound is prepared in analogy to rac-4-(2,2-dimethyl-[1,3]dioxolan-4-ylmethoxy)-N-hydroxy-3,5-dimethyl-benzamidine from 3-ethyl-4-hydroxy-5-methyl-benzonitrile and (R)-(2,2-dimethyl-[1,3]dioxolan-4-yl)-methanol; LC-MS**: $t_R$=0.46 min, [M+H]$^+$=309.23; $^1$H NMR (D$_6$-DMSO): δ1.17 (t, J=7.5 Hz, 3H), 1.33 (s, 3H), 1.38 (s, 3H), 2.25 (s, 3H), 2.57-2.69 (m, 2H), 3.73-3.84 (m, 3H), 4.12 (t, J=7.0 Hz, 1H), 4.39-4.45 (m, 1H), 5.76 (s br, 2H), 7.34 (s, 1H), 7.36 (s, 1H), 9.47 (s, 1H).

(R)-3-Chloro-4-(2,2-dimethyl-[1,3]dioxolan-4-ylmethoxy)-N-hydroxy-5-methyl-benzamidine The title compound is obtained as a colorless oil (1.39 g) in analogy to rac-4-(2,2-dimethyl-[1,3]dioxolan-4-ylmethoxy)-N-hydroxy-3,5-dimethyl-benzamidine starting from 3-chloro-4-hydroxy-5-methyl-benzonitrile and L-α,β-isopropyliden glycerol; LC-MS: $t_R$=0.66 min, [M+H]$^+$=314.96.

(R)-4-(2,2-Dimethyl-[1,3]dioxolan-4-ylmethoxy)-N-hydroxy-3-methoxy-5-methyl-benzamidine The title compound is obtained as a beige oil (1.16 g) in analogy to rac-4-(2,2-dimethyl-[1,3]dioxolan-4-ylmethoxy)-N-hydroxy-3,5-dimethyl-benzamidine starting from 4-hydroxy-3-methoxy-5-methyl-benzonitrile and L-α,β-isopropyliden glycerol; LC-MS: $t_R$=0.65 min, [M+H]$^+$=311.0.

(R)-3-Chloro-4-(2,2-dimethyl-[1,3]dioxolan-4-ylmethoxy)-N-hydroxy-5-methoxy-benzamidine The title compound is prepared in analogy to rac-4-(2,2-dimethyl-[1,3]dioxolan-4-ylmethoxy)-N-hydroxy-3,5-dimethyl-benzamidine starting from 3-chloro-4-hydroxy-5-methoxy-benzonitrile and L-α,β-isopropyliden glycerol; LC-MS: $t_R$=0.42 min, [M+H]$^+$=331.17; $^1$H NMR (D$_6$-DMSO): δ1.30 (s, 3H), 1.34 (s, 3H), 3.86 (s, 3H), 3.87-3.93 (m, 2H), 4.00-4.12 (m, 2H), 4.36 (quint, J=5.8 Hz, 1H), 5.90 (s, 2H), 7.32 (d, J=2.0 Hz, 1H), 7.34 (d, J=2.0 Hz, 1H), 9.71 (s, 1H).

(R)-4-(2,2-Dimethyl-[1,3]dioxolan-4-ylmethoxy)-N-hydroxy-2-methoxy-benzamidine The title compound is obtained as a beige oil (2.46 g) in analogy to rac-4-(2,2-dimethyl-[1,3]dioxolan-4-ylmethoxy)-N-hydroxy-3,5-dimethyl-benzamidine starting from 4-hydroxy-2-methoxy-benzonitrile and L-α,β-isopropyliden glycerol; LC-MS: $t_R$=0.62 min, [M+H]$^+$=296.97.

(S)-4-(3-Amino-2-hydroxypropoxy)-3-ethyl-5-methylbenzonitrile a) To a solution of 3-ethyl-4-hydroxy-5-methyl-benzonitrile (5.06 g, 31.4 mmol) in THF (80 mL), PPh$_3$ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane:EA 7:3 to give 3-ethyl-5-methyl-4-oxiranylmethoxy-benzonitrile (5.85 g) as a yellow oil; LC-MS: $t_R$=0.96 min; $[M+42]^+$=259.08.

b) The above epoxide is dissolved in 7 N $NH_3$ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g) as a yellow oil; LC-MS: $t_R$=0.66 min; $[M+1]^+$=235.11.

N—((S)-3-[2-Ethyl-4-(N-hydroxycarbamimidoyl)-6-methyl-phenoxy]-2-hydroxy-propyl)-2-hydroxy-acetamide a) To a solution of (S)-4-(3-amino-2-hydroxypropoxy)-3-ethyl-5-methylbenzonitrile (6.23 g, 26.59 mmol) in THF (150 mL), glycolic acid (2.43 g, 31.9 mmol), HOBt (4.31 g, 31.9 mmol), and EDC hydrochloride (6.12 g, 31.9 mmol) are added. The mixture is stirred at rt for 18 h before it is diluted with sat. aq. $NaHCO_3$ and extracted twice with EA. The combined org. extracts are dried over $MgSO_4$, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g) as a yellow oil; LC-MS: $t_R$=0.74 min; $[M+1]^+$=293.10; $^1$H NMR ($CDCl_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (s, br, 3H), 7.06 (m, 1H), 7.36 (s, 1H), 7.38 (s, 1H).

b) The above nitrile is converted to the N-hydroxy-benzamidine according to literature procedures (e.g. E. Meyer, A. C. Joussef, H. Gallardo, *Synthesis* 2003, 899-905); LC-MS: $t_R$=0.51 min; $[M+1]^+$=326.13; $^1$H NMR ($D_6$-DMSO): δ 1.17 (t, J 7.4 Hz, 3H), 2.24 (s, 3H), 2.62 (q, J 7.4 Hz, 2H), 3.23 (m, 1H), 3.43 (m, 1H), 3.67 (m, 2H), 3.83 (s, 2H), 3.93 (m, 1H), 5.27 (s br, 1H), 5.58 (s br, 1H), 5.70 (s, 2H), 7.34 (s, 1H), 7.36 (s, 1H), 7.67 (m, 1H), 9.46 (s br, 1H).

(S)-2-Hydroxy-N-{2-hydroxy-3-[4-(N-hydroxycarbamimidoyl)-2,6-dimethyl-phenoxy]-propyl}-acetamide The title compound is prepared in analogy to N—((S)-3-[2-ethyl-4-(N-hydroxycarbamimidoyl)-6-methyl-phenoxy]-2-hydroxy-propyl)-2-hydroxy-acetamide; LC-MS: $t_R$=0.23 min, $[M+1]^+$=312.25.

N—((S)-3-[2-Ethyl-4-(N-hydroxycarbamimidoyl)-6-methyl-phenoxy]-2-hydroxy-propyl)-2-hydroxy-acetamide a) To a solution of 3-ethyl-4-hydroxy-5-methyl-benzonitrile (5.06 g, 31.4 mmol) in THF (80 mL), $PPh_3$ (9.06 g, 34.5 mmol) and (R)-glycidol (2.29 mL, 34.5 mmol) are added. The mixture is cooled to 0° C. before DEAD in toluene (15.8 mL, 34.5 mmol) is added. The mixture is stirred for 18 h while warming up to rt. The solvent is evaporated and the crude product is purified by CC on silica gel eluting with heptane:EA 7:3 to give 3-ethyl-5-methyl-4-oxiranylmethoxy-benzonitrile (5.85 g) as a yellow oil; LC-MS: $t_R$=0.96 min; $[M+42]^+$=259.08.

b) The above epoxide is dissolved in 7 N $NH_3$ in methanol (250 mL) and the solution is stirred at 65° C. for 18 h. The solvent is evaporated to give crude (S)-4-(3-amino-2-hydroxypropoxy)-3-ethyl-5-methylbenzonitrile (6.23 g) as a yellow oil; LC-MS: $t_R$=0.66 min; $[M+1]^+$=235.11.

c) To a solution of (S)-4-(3-amino-2-hydroxypropoxy)-3-ethyl-5-methylbenzonitrile (6.23 g, 26.59 mmol) in THF (150 mL), glycolic acid (2.43 g, 31.9 mmol), HOBt (4.31 g, 31.9 mmol), and EDC hydrochloride (6.12 g, 31.9 mmol) are added. The mixture is stirred at rt for 18 h before it is diluted with sat. aq. $NaHCO_3$ and extracted twice with EA. The combined org. extracts are dried over $MgSO_4$, filtered and concentrated. The crude product is purified by CC with DCM containing 8% of methanol to give (S)—N-[3-(4-cyano-2-ethyl-6-methyl-phenoxy)-2-hydroxy-propyl]-2-hydroxy-acetamide (7.03 g) as a yellow oil; LC-MS: $t_R$=0.74 min; $[M+1]^+$=293.10; $^1$H NMR ($CDCl_3$): δ 1.25 (t, J=7.5 Hz, 3H), 2.32 (s, 3H), 2.69 (q, J=7.5 Hz, 2H), 3.48-3.56 (m, 3H), 3.70-3.90 (m, 3H), 4.19 (s, br, 3H), 7.06 (m, 1H), 7.36 (s, 1H), 7.38 (s, 1H).

d) The above nitrile is converted to the title compound according to literature procedures (e.g. E. Meyer, A. C. Joussef, H. Gallardo, *Synthesis* 2003, 899-905); LC-MS: $t_R$=0.51 min; $[M+1]^+$=326.13; $^1$H NMR ($D_6$-DMSO): δ 1.17 (t, J 7.4 Hz, 3H), 2.24 (s, 3H), 2.62 (q, J 7.4 Hz, 2H), 3.23 (m, 1H), 3.43 (m, 1H), 3.67 (m, 2H), 3.83 (s, 2H), 3.93 (m, 1H), 5.27 (s br, 1H), 5.58 (s br, 1H), 5.70 (s, 2H), 7.34 (s, 1H), 7.36 (s, 1H), 7.67 (m, 1H), 9.46 (s br, 1H).

(S)—N-(3-[2-Chloro-4-(N-hydroxycarbamimidoyl)-6-methyl-phenoxy]-2-hydroxy-propyl)-2-hydroxy-acetamide The title compound is obtained as a beige wax (1.1 g) in analogy to N—((S)-3-[2-ethyl-4-(N-hydroxycarbamimidoyl)-6-methyl-phenoxy]-2-hydroxy-propyl)-2-hydroxy-acetamide starting from 3-chloro-4-hydroxy-5-methyl-benzonitrile; LC-MS: $t_R$=0.48 min, $[M+H]^+$=331.94.

(S)-2-Hydroxy-N-(2-hydroxy-3-[4-(N-hydroxycarbamimidoyl)-2-methoxy-6-methyl-phenoxy]-propyl)-acetamide The title compound is obtained as a reddish oil (1.3 g) in analogy to N—((S)-3-[2-ethyl-4-(N-hydroxycarbamimidoyl)-6-methyl-phenoxy]-2-hydroxy-propyl)-2-hydroxy-acetamide starting from 4-hydroxy-3-methoxy-5-methyl-benzonitrile; LC-MS: $t_R$=0.49 min, $[M+H]^+$=327.98.

4-(2,2-Dimethyl-[1,3]dioxan-5-ylmethoxy)-3-ethyl-N-hydroxy-5-methyl-benzamidine To a solution of 3-ethyl-4-hydroxy-5-methyl-benzonitrile (480 mg, 2.98 mmol) in THF (10 mL), triphenylphosphine (1.17 g, 4.47 mmol) and (2,2-dimethyl-[1,3]dioxan-5-yl)-methanol (478 mg, 3.28 mmol) is added. The mixture is cooled to 4° C. before DEAD (1.94 g, 4.47 mmol, 2.05 mL of a 40% solution in toluene) is added. Stirring is continued at 4° C. for 15 min, then at rt for 1 h. The solvent is removed in vacuo and the crude product is purified by CC on silica gel eluting with heptane:EA 9:1 to give 4-(2,2-dimethyl-[1,3]dioxan-5-ylmethoxy)-3-ethyl-5-methyl-benzonitrile (240 mg) as a yellow oil; LC-MS: $t_R$=1.04 min; $[M+1+CH_3CN]^+$=330.97. To a solution of this material (240 mg, 829 μmol) in methanol (5 mL), hydroxylamine hydrochloride (86 mg, 1.24 mmol) and $NaHCO_3$ (104 mg, 1.24 mmol) is added. The mixture is stirred at 60° C. for 5 h before it is diluted with EA and washed with water. The org. extract is dried over $MgSO_4$,

3-Ethyl-4-[(S)-2-hydroxy-3-(2-hydroxy-acetylamino)-propoxy]-5-methyl-benzoic acid a) To an ice-cold solution of $H_2SO_4$ (150 mL) in water (250 mL), 2-ethyl-6-methylaniline (15.0 g, 111 mmol) is added. The solution is treated with ice (150 g) before a solution of $NaNO_2$ (10.7 g, 155 mmol) in water (150 mL) and ice (50 g) is added dropwise. The mixture is stirred at 0° C. for 1 h. 50% aq. $H_2SO_4$ (200 mL) is added and stirring is continued at rt for 18 h. The mixture is extracted with DCM, and the org. extracts are dried over $MgSO_4$ and evaporated. The crude product is purified by CC on silica gel eluting with heptane:EA 9:1 to give 2-ethyl-6-methyl-phenol (8.6 g) as a crimson oil; LC-MS: $t_R$=0.89 min; $^1$H NMR (CDCl$_3$): δ7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condensor and the mixture is refluxed for 3 h. The mixture is cooled to rt, diluted with water (100 mL) and extracted with EA. The org. extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

c) To a solution of 3-ethyl-4-hydroxy-5-methyl-benzaldehyde (25.0 g, 152 mmol) in acetonitrile (250 mL), K$_2$CO$_3$ (42.1 g, 305 mmol) followed by benzyl bromide (26.0 g, 152 mmol) is added. The suspension is stirred at 60° C. for 18 h. The mixture is diluted with water (150 mL) and EA (150 mL). The org. extract is separated and the aq. phase is extracted once more with EA (100 mL). The combined org. extracts are washed with water (150 mL) and concentrated. The crude product is purified by CC on silica gel eluting with heptane:EA 9:1 to give 4-benzyloxy-3-ethyl-5-methyl-benzaldehyde (27.2 g) as a yellow oil; LC-MS: $t_R$=1.09 min; $^1$H NMR (D$_6$-DMSO): δ1.19 (t, J=7.5 Hz, 3H), 2.35 (s, 3H), 2.70 (q, J=7.5 Hz, 2H), 4.90 (s, 2H), 7.37-7.41 (m, 1H), 7.42-7.46 (m, 2H), 7.49-7.52 (m, 2H), 7.65-7.69 (m, 2H), 9.92 (s, 1H).

d) To a solution of 4-benzyloxy-3-ethyl-5-methyl-benzaldehyde (25.0 g, 98.3 mmol) in acetone (500 mL), KMnO$_4$ (20.2 g, 127.8 mmol) is added. The mixture becomes warm (45° C.). The mixture is stirred at rt for 16 h before it is filtered over glass filters. The clear, colourless filtrate is concentrated, diluted with water and acidified with 2 N aq. HCl, then extracted twice with EA. The combined org. extracts are dried over MgSO$_4$, filtered concentrated and dried to give 4-benzyloxy-3-ethyl-5-methyl-benzoic acid (19.2 g) as a pale yellow solid; LC-MS: $t_R$=1.00 min; $^1$H NMR (D$_6$-DMSO): δ1.13-1.22 (m, 3H), 2.32 (s, 3H), 2.64-2.72 (m, 2H), 4.87 (s, 2H), 7.34-7.56 (m, 5H), 7.69 (m, 2H), 12.66 (s br, 1H).

e) To a suspension of 4-benzyloxy-3-ethyl-5-methyl-benzoic acid (10.0 g, 37.0 mmol) in toluene (150 mL), N,N-dimethylformamide di-tert.butyl acetal (22.6 g, 111 mmol) is added. The mixture is refluxed for 24 h before another portion of N,N-dimethylformamide di-tert.butyl acetal (22.6 g, 111 mmol) is added. Refluxing is continued for another 24 h, then another portion of N,N-dimethylformamide di-tert.butyl acetal (22.6 g, 111 mmol) is added. The mixture is again refluxed for 24 h before it is cooled to rt, diluted with EA and washed with sat. aq. Na$_2$CO$_3$ solution. The org. extract is dried over MgSO$_4$, filtered and concentrated. The crude product is purified by CC on silica gel eluting with heptane:EA 9:1 to give 4-benzyloxy-3-ethyl-5-methyl-benzoic acid tert.butyl ester (9.02 g) as a pale yellow oil; LC-MS: $t_R$=1.17 min.

f) To a solution of 4-benzyloxy-3-ethyl-5-methyl-benzoic acid tert.butyl ester (9.02 g, 27.6 mmol) in THF (50 mL) and ethanol (50 mL), Pd/C (400 mg, 10% Pd) is added. The slurry is stirred at rt for 24 h under 1 bar of H$_2$. The catalyst is removed by filtration, the filtrate is concentrated, dissolved again in THF (50 mL) and ethanol (50 mL), and again treated with Pd/C (400 mg, 10% Pd). The slurry is stirred at rt for 24 h under 1 bar of H$_2$. The catalyst is again removed by filtration and the filtrate is concentrated and dried to give 3-ethyl-4-hydroxy-5-methyl-benzoic acid tert.butyl ester (7.13 g) as a pale yellow oil; LC-MS: $t_R$=1.01 min; $^1$H NMR (CDCl$_3$): δ1.28 (t, J=7.8 Hz, 3H), 1.61 (s, 9H), 2.30 (s, 3H), 2.67 (q, J=7.5 Hz, 2H), 5.13 (s br, 1H), 7.67 (s, 1H), 7.69 (s, 1H).

g) 3-Ethyl-4-[(S)-2-hydroxy-3-(2-hydroxy-acetylamino)-propoxy]-5-methyl-benzoic acid tert-butyl ester (5.94 g) is prepared starting from the above 3-ethyl-4-hydroxy-5-methyl-benzoic acid tert.butyl ester (6.53 g, 27.6 mmol) following the procedures given for N—((S)-3-[2-ethyl-4-(N-hydroxycarbamimidoyl)-6-methyl-phenoxy]-2-hydroxy-propyl)-2-hydroxy-acetamide; LC-MS: $t_R$=0.87 min; [M+H]$^+$=368.11; $^1$H NMR (CDCl$_3$): δ1.17 (t, J=7.5 Hz, 3H), 1.53 (s, 9H), 2.28 (s, 3H), 2.66 (q, J=7.5 Hz, 2H), 3.17-3.26 (m, 1H), 3.38-3.46 (m, 1H), 3.65-3.75 (m, 2H), 3.83 (d, J=5.5 Hz, 2H), 3.91-3.97 (m, 1H), 5.28 (d, J=5.3 Hz, 1H), 5.54 (t, J=5.5 Hz, 1H), 7.59 (s, 1H), 7.60 (s, 1H), 7.68 (t, J=5.5 Hz, 1H).

h) To a cooled (0° C.) solution of 3-ethyl-4-[(S)-2-hydroxy-3-(2-hydroxy-acetylamino)-propoxy]-5-methyl-benzoic acid tert.butyl ester (5.94 g, 16.2 mmol) in DCM (100 mL), TFA (5 mL) is added. The mixture is warmed to rt and stirred for 2 h. The mixture is concentrated, dissolved in acetonitrile/water (6 mL) and separated by prep. HPLC to give the title compound (2.20 g) as a white powder; LC-MS: $t_R$=0.41 min; [M+H]$^+$=312.18.

4-Benzyloxy-3,5-dimethyl-benzoic acid hydrazide

The title compound is prepared in analogy to 4-benzyloxy-3-ethyl-5-methyl-benzoic acid hydrazide as described below; LC-MS: $t_R$=0.78 min; [M+1]$^+$=271.19; $^1$H NMR (CDCl$_3$): δ 2.30 (s, 6H), 3.86 (s br, 2H), 4.82 (s, 2H), 7.30-7.50 (m, 7H), 7.58 (s br, 1H).

4-Benzyloxy-3-ethyl-5-methyl-benzoic acid hydrazide a) To a solution of 3-ethyl-4-hydroxy-5-methyl-benzaldehyde (34.9 g, 0.213 mol, prepared from 2-ethyl-6-methyl-phenol according to the literature cited for 3-ethyl-4,N-dihydroxy-5-methyl-benzamidine) in MeCN (350 mL), K$_2$CO$_3$ (58.7 g, 0.425 mol) and benzylbromide (36.4 g, 0.213 mol) are added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of $NaH_2PO_4$ dihydrate (249 g, 2.08 mol) in water (1500 mL) is added. To this mixture, $NaClO_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aq. phase is acidified with 25% aq. HCl (500 mL) and extracted twice with TBME (1000 mL). These org. extracts are combined and evaporated to dryness to give 4-benzyloxy-3-ethyl-5-methyl-benzoic acid; $^1$H NMR ($D_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

c) 4-Benzyloxy-3-ethyl-5-methyl-benzoic acid is converted to 4-benzyloxy-3-ethyl-5-methyl-benzoic acid hydrazide following step c) of the preparation of 4-allyloxy-3,5-dimethyl-benzoic acid hydrazide; LC-MS: $t_R$=0.82 min, $[M+1]^+$=285.44.

3-[4-(N-Hydroxycarbamimidoyl)-2,6-dimethyl-phenyl]-propionic acid tert-butyl ester a) To an ice-cooled solution of 4-hydroxy-3,5-dimethyl-benzoic acid methyl ester (7.52 g, 41.7 mmol) in DCM (250 mL) and pyridine (10 mL), trifluoromethanesulfonic acid anhydride (13.0 g, 45.9 mmol) is added over a period of 20 min. Upon complete addition, the ice bath is removed and the reaction is stirred for further 1 h at rt. The mixture is diluted with DCM (150 mL), washed with 10% aq. citric acid solution followed by brine, dried over $MgSO_4$, filtered and evaporated. The residue is purified by FC on silica gel eluting with heptane:EA 9:1 to give 3,5-dimethyl-4-trifluoromethanesulfonyloxy-benzoic acid methyl ester (11.8 g) as colourless fine needles; LC-MS: $t_R$=1.08 min.

b) To a stirred solution of the above triflate (11.8 g, 37.8 mmol) in dry DMF (155 mL) is sequentially added triethylamine (7.6 g, 75.6 mmol), tert.-butyl acrylate (48.4 g, 378 mmol), DPPP (779 mg, 1.89 mmol) and Pd(OAc)$_2$ (424 mg, 1.89 mmol) under nitrogen. The mixture is stirred at 115° C. for 18 h before another portion of DPPP (160 mg, 0.39 mmol) and Pd(OAc)$_2$ (80 mg, 0.36 mmol) is added. Stirring is continued for 4 h at 115° C. before the mixture is cooled to rt, diluted with diethyl ether (350 mL) and washed with 1 N aq. HCl, followed by sat. aq. NaHCO$_3$ solution. The org. extract is dried over MgSO$_4$, filtered and evaporated. The residue is purified by FC on silica gel eluting with heptane:EA 4:1 to give 4-(2-tert-butoxycarbonyl-vinyl)-3,5-dimethyl-benzoic acid methyl ester (11.21 g) as a colourless solid; LC-MS: $t_R$=1.09 min.

c) To a solution of 4-(2-tert-butoxycarbonyl-vinyl)-3,5-dimethyl-benzoic acid methyl ester (11.2 g, 38.6 mmol) in ethanol (50 mL) and THF (50 mL), Pd/C (1.0 g, 10% Pd) is added. The mixture is stirred for 16 h at rt under 2.5 bar of H$_2$. The catalyst is filtered off and the filtrate is concentrated and dried under HV to give 4-(2-tert-butoxycarbonyl-ethyl)-3,5-dimethyl-benzoic acid methyl ester (10.8 g) as a colourless oil; LC-MS: $t_R$=1.08 min.

d) To a solution of 4-(2-tert-butoxycarbonyl-ethyl)-3,5-dimethyl-benzoic acid methyl ester (10.8 g, 37.0 mmol) in ethanol (100 mL) a 2 M aq. solution of LiOH (50 mL) is added at 0° C. The turbid mixture is stirred at 0° C. for 30 min, then at rt for 4 h. The mixture is diluted with 10% aq. citric acid solution and extracted three times with diethyl ether. The combined org. extracts are dried over MgSO$_4$, filtered and concentrated. The solid residue is suspended in diethyl ether/heptane, stirred at rt, and filtered. The slurry procedure in diethyl ether/heptane is repeated. The solid material is collected and dried under HV to give 4-(2-tert-butoxycarbonyl-ethyl)-3,5-dimethyl-benzoic acid (5.09 g) as a white crystalline powder; LC-MS: $t_R$=0.95 min, $[M+1]^+$=279.14; $^1$H NMR (CDCl$_3$): δ1.47 (s, 9H), 2.30-2.40 (m, 2H), 2.39 (s, 6H), 2.94-3.03 (m, 2H), 7.75 (s, 2H).

e) To a suspension of 4-(2-tert-butoxycarbonyl-ethyl)-3,5-dimethyl-benzoic acid (8.00 g, 28.7 mmol) in isopropanol (100 mL), HOBt (4.27 g, 31.6 mmol) followed by EDC hydrochloride (6.34 g, 33.1 mmol) is added. After stirring at rt for 1 h, 25% aq. ammonia (16.1 mL) is added. Stirring is continued for 30 min before the isopropanol is evaporated under reduced pressure. The remaining solution is diluted with isopropyl acetate (200 mL), washed three times with approximately 0.5 N aq. NaHCO$_3$ solution (100 mL) followed by water (50 mL), dried over MgSO$_4$, filtered, concentrated and dried to give 3-(4-carbamoyl-2,6-dimethyl-phenyl)-propionic acid tert-butyl ester (7.5 g) as an off-white solid.

f) To an ice-cooled solution of 3-(4-carbamoyl-2,6-dimethyl-phenyl)-propionic acid tert-butyl ester (7.00 g, 25.2 mmol) and triethylamine (7.66 g, 75.7 mmol) in DCM (100 mL), trifluoroacetic anhydride (6.06 g, 28.8 mmol) is added slowly so that the reaction temperature stays below 15° C. The clear yellow solution is stirred at rt for 1 h before it is washed twice with water (100 mL) and concentrated. The crude product is purified by recrystallisation from methanol to give 3-(4-cyano-2,6-dimethyl-phenyl)-propionic acid tert-butyl ester (4.2 g) as a white solid, $^1$H NMR (CDCl$_3$): δ 1.48 (s, 9H), 2.33-2.37 (m, 2H), 2.38 (s, 6H), 2.94-3.01 (m, 2H), 7.31 (s, 2H).

g) A solution of 3-(4-cyano-2,6-dimethyl-phenyl)-propionic acid tert-butyl ester (4.1 g, 15.8 mmol), hydroxylamine hydrochloride (1.65 g, 23.7 mmol) and triethylamine (3.20 g, 31.6 mmol) in methanol (40 mL) is refluxed for 2 h before the solvent is removed in vacuo. The residue is taken up in isopropyl acetate (50 mL) and washed twice with water (50 mL). The org. extract is dried over MgSO$_4$, filtered, evaporated and dried to give 3-[4-(N-hydroxycarbamimidoyl)-2,6-dimethyl-phenyl]-propionic acid tert-butyl ester (4.4 g) as a white solid.

3-[2-Ethyl-4-(N-hydroxycarbamimidoyl)-6-methyl-phenyl]-propionic acid tert-butyl ester The title compound is prepared in analogy to 3-[4-(N-hydroxycarbamimidoyl)-2,6-dimethyl-phenyl]-propionic acid tert-butyl ester; $^1$H NMR (CDCl$_3$): δ 1.26 (t, J=7.5 Hz, 3H), 2.34-2.41 (m, 5H), 2.70 (q, J=7.8 Hz, 2H), 2.94-3.01 (m, 2H), 4.85 (s br, 1H), 7.28 (s, 1H), 7.32 (s, 1H).

3-{2-Ethyl-4-[5-(5-isobutyl-4-methyl-pyridin-2-yl)-[1,2,4]oxadiazol-3-yl]-6-methyl-phenyl}-propionic acid a) To a solution of 5-isobutyl-4-methyl-pyridine-2-carboxylic acid (246 mg, 1.07 mmol) and DIPEA (415 mg, 3.21 mmol) in DMF (4 mL), PyBOP (589 mg, 1.13 mmol) is added at 0° C. The mixture is stirred for 15 min at 0° C. before 3-[2-ethyl-4-(N-hydroxycarbamimidoyl)-6-methyl-phenyl]-propionic acid tert-butyl ester (328 mg, 1.07 mmol) is added and stirring is continued for 1 h at 0° C. The reaction is quenched by adding water, the mixture is diluted with sat. aq. NaHCO$_3$-solution and extracted twice with EA. The combined org. extracts are dried over MgSO$_4$, filtered and concentrated to give the crude hydroxy-amidine ester intermediate; LC-MS: t$_R$=1.10 min, [M+H]$^+$=482.27. This material is dissolved in dioxane (10 mL) and the mixture is stirred at 80° C. for 15 h. The solvent is evaporated and the crude product is purified by CC on silica gel eluting with heptane:EA 7:3 to give 3-{2-ethyl-4-[5-(5-isobutyl-4-methyl-pyridin-2-yl)-[1,2,4]oxadiazol-3-yl]-6-methyl-phenyl}-propionic acid tert-butyl ester (420 mg) as a colourless oil; LC-MS: t$_R$=1.26 min, [M+H]$^+$=464.34.

b) The above tert.butyl ester (437 mg, 0.943 mmol) is dissolved in 6 N aq. HCl and the mixture is stirred at 65° C. for 18 h. The solvent is removed in vacuo and the remaining residue is washed with EA and dried under HV to give the title compound (371 mg) as a white solid; LC-MS: t$_R$=1.10 min, [M+H]$^+$=408.21; $^1$H NMR (D$_6$-DMSO): δ 0.93 (d, J=6.5 Hz, 6H), 1.23 (t, J=7.5 Hz, 3H), 1.91 (hept, J=6.8 Hz), 2.37-2.43 (m, 5H), 2.44 (s, 3H), 2.62 (d, J=7.0 Hz, 2H), 2.74 (q, J=7.5 Hz, 2H), 2.91-2.98 (m, 2H), 7.75 (s, 1H), 7.76 (s, 1H), 8.16 (s, 1H), 8.53 (s, 1H), 10.26 (s br, 1H).

Example 1

N—((S)-3-{2-Ethyl-4-[5-(6-isobutyl-4-methyl-pyridin-2-yl)-[1,2,4]oxadiazol-3-yl]-6-methyl-phenoxy}-2-hydroxy-propyl)-2-hydroxy-acetamide To a solution of 6-isobutyl-4-methyl-pyridine-2-carboxylic acid (100 mg, 0.435 mmol) and DIPEA (169 mg, 1.31 mmol) in DMF (5 mL), TBTU (210 mg, 0.653 mmol) is added at 0° C. The mixture is stirred for 15 min at 0° C. before N—((S)-3-[2-ethyl-4-(N-hydroxycarbamimidoyl)-6-methyl-phenoxy]-2-hydroxy-propyl)-2-hydroxy-acet-amide (170 mg, 0.522 mmol) is added. Stirring is continued at 0° C. for 1 h. The reaction is quenched by adding water. The mixture is diluted with sat. aq. NaHCO$_3$-solution and extracted with EA and two times with DCM. The combined org. extracts are dried over MgSO$_4$, filtered and concentrated to give the crude hydroxy-amidine ester intermediate. This material is dissolved in dioxane (5 mL) and the mixture is stirred at 80° C. for 24 h. The solvent is evaporated and the crude product is purified on prep. TLC plates with DCM containing 10% of 7 N NH$_3$ in methanol followed by prep. HPLC to give the title compound (21 mg) as a pale yellow oil; LC-MS: t$_R$=1.00 min, [M+H]$^+$=483.26; $^1$H NMR (CDCl$_3$): δ 0.99 (d, J=6.8 Hz, 6H), 1.29 (t, J=7.5 Hz, 3H), 2.21 (hept, J=6.8 Hz, 1H), 2.36 (s, 3H), 2.48 (s, 3H), 2.72 (q, J=7.5 Hz, 2H), 2.79 (d, J=7.3 Hz, 2H), 3.47-3.55 (m, 1H), 3.74-3.92 (m, 3H), 4.16-4.24 (m, 3H), 7.18 (s, 1H), 7.23 (t br, J=5.8 Hz, 1H), 7.88 (s, 1H), 7.90 (s, 1H), 7.99 (s, 1H).

Example 2

2-Ethyl-4-[5-(4-isobutyl-6-methyl-pyridin-2-yl)-[1,2,4]oxadiazol-3-yl]-6-methyl-phenol To a solution of 4-isobutyl-6-methyl-pyridine-2-carboxylic acid (480 mg, 2.09 mmol) and DIPEA (810 mg, 6.27 mmol) in DMF (20 mL), PyBOP (1150 mg, 2.21 mmol) is added at 0° C. The mixture is stirred for 15 min at 0° C. before 3-ethyl-4,N-dihydroxy-5-methyl-benzamidine (429 mg, 2.21 mmol) is added and stirring is continued for 1 h at 0° C. The reaction is quenched by adding water, the mixture is diluted with sat. aq. NaHCO$_3$-solution and extracted twice with EA. The combined org. extracts are dried over MgSO$_4$, filtered and concentrated to give the crude hydroxy-amidine ester intermediate; LC-MS: t$_R$=0.90 min, [M+H]$^+$=370.16. This material is dissolved in dioxane (10 mL) and the mixture is stirred at 80° C. for 15 h. The solvent is evaporated and the crude product is purified by CC on silica gel eluting with heptane:EA 7:3 to give the title compound (112 mg) as a pale purple oil; LC-MS: t$_R$=1.12 min, [M+H]$^+$=352.17.

Example 3

(S)-3-{2-Ethyl-4-[5-(4-isobutyl-6-methyl-pyridin-2-yl)-[1,2,4]oxadiazol-3-yl]-6-methyl-phenoxy}-propane-1,2-diol To a solution of 2-ethyl-4-[5-(4-isobutyl-6-methyl-pyridin-2-yl)-[1,2,4]oxadiazol-3-yl]-6-methyl-phenol (41 mg, 0.116 mmol) in isopropanol (3 mL) and 3 N aq. NaOH (0.4 mL), (S)-3-chloro-1,2-propanediol (66 mg, 0.577 mmol) is added. The mixture is stirred at 65° C. for 16 h before another portion of (S)-3-chloro-1,2-propanediol (66 mg, 0.577 mmol) and 3 N aq. NaOH (0.4 mL) is added. Stirring is continued at 65° C. for 24 h. The mixture is cooled to rt, diluted with water, and repeatedly extracted with diethyl ether. The combined org. extracts are dried over MgSO$_4$, filtered and concentrated. The crude product is purified on prep. TLC using DCM:methanol 9:1 to give the title compound (16 mg) as a colourless oil; LC-MS: t$_R$=1.02 min, [M+H]$^+$=426.17.

Example 4

(S)-1-Amino-3-{2-ethyl-4-[5-(4-isobutyl-6-methyl-pyridin-2-yl)-[1,2,4]oxadiazol-3-yl]-6-methyl-phenoxy}-propan-2-ol a) To a solution of 2-ethyl-4-[5-(4-isobutyl-6-methyl-pyridin-2-yl)-[1,2,4]oxadiazol-3-yl]-6-methyl-phenol (79 mg, 0.224 mmol) in THF (6 mL), (R)-(+)-glycidol (25 mg, 0.335 mmol) and triphenyl phosphine (88 mg, 0.335 mmol) are added. The mixture is stirred and cooled to 0° C. before DEAD (58 mg, 0.335 mmol, as a 40% solution in toluene) is added. The mixture is warmed to rt and stirring is continued for 4 h. Another portion of (R)-(+)-glycidol (8 mg, 0.112 mmol), triphenyl phosphine (30 mg, 0.112 mmol) and DEAD (19 mg, 0.112 mmol) is added. Stirring is continued for 4 h before the solvent is evaporated. The crude product is purified on prep. TLC using heptane:EA 7:3 to give 2-[3-((S)-3-ethyl-5-methyl-4-oxiranylmethoxy-phenyl)-[1,2,4]oxadiazol-5-yl]-4-isobutyl-6-methyl-pyridine (46 mg) as a yellow oil; LC-MS: $t_R$=1.17 min, $[M+H]^+$=408.19.

b) The above epoxide (46 mg, 0.114 mmol) is dissolved in 7 N $NH_3$ in methanol (10 mL) and the mixture is stirred at 45° C. for 16 h in a sealed vessel. The solvent is evaporated and the crude product is purified by prep. TLC using DCM containing 6% of 7 N $NH_3$ in methanol to give the title compound (38 mg) as white solid; LC-MS: $t_R$=0.88 min, $[M+H]^+$=425.24.

Example 5

N—((S)-3-{2-Ethyl-4-[5-(4-isobutyl-6-methyl-pyridin-2-yl)-[1,2,4]oxadiazol-3-yl]-6-methyl-phenoxy}-2-hydroxy-propyl)-2-hydroxy-acetamide To a solution of (S)-1-amino-3-{2-ethyl-4-[5-(4-isobutyl-6-methyl-pyridin-2-yl)-[1,2,4]oxadiazol-3-yl]-6-methyl-phenoxy}-propan-2-ol (36 mg, 86 µmol), HOBt (14 mg, 103 µmol) and glycolic acid (8 mg, 103 µmol) in THF (3 mL), EDC HCl (20 mg, 103 µmol) is added. The mixture is stirred at rt for 18 h before it is diluted with sat. aq. $NaHCO_3$-solution and extracted twice with EA. The combined org. extracts are dried over $MgSO_4$, filtered and concentrated. The crude product is purified by prep. TLC using DCM containing 11% of methanol to give the title compound (36 mg) as a pale yellow oil; LC-MS: $t_R$=0.98 min, $[M+H]^+$=483.21; $^1$H NMR ($CDCl_3$): δ 0.98 (d, J=6.3 Hz, 6H), 1.31 (t, J=7.5 Hz, 3H), 1.97-2.08 (m, 1H), 2.38 (s, 3H), 2.59 (d, J=6.8 Hz, 2H), 2.69-2.78 (m, 5H), 2.81 (s br, 1H), 3.42 (s br, 1H). 3.48-3.57 (m, 2H), 3.74-3.93 (m, 2H), 4.17-4.25 (m, 3H), 7.05 (s br, 1H), 7.19 (s, 1H), 7.93 (s, 1H), 7.94 (s, 2H).

Example 6

4-[5-(6-Isobutyl-4-methoxy-pyridin-2-yl)-[1,2,4]oxadiazol-3-yl]-2,6-dimethyl-phenol The title compound is prepared in analogy to Example 2 starting from 6-isobutyl-4-methoxy-pyridine-2-carboxylic acid and 4,N-dihydroxy-3,5-dimethyl-benzamidine; LC-MS: $t_R$=1.01 min, $[M+H]^+$=354.28; $^1$H NMR ($CDCl_3$): δ 0.99 (d, J=6.8 Hz, 6H), 2.19-2.28 (m, 1H), 2.35 (s, 6H), 2.78 (d, J=7.5 Hz, 2H), 3.98 (s, 3H), 4.96 (s, 1H), 6.85 (d, J=2.3 Hz, 1H), 7.70 (d, J=2.3 Hz, 1H), 7.88 (s, 2H).

Examples 7 to 10

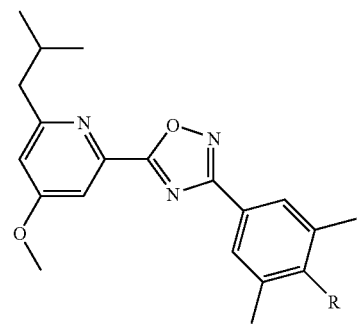

The following Examples are prepared in analogy to previous Examples starting from 4-[5-(6-isobutyl-4-methoxy-pyridin-2-yl)-[1,2,4]oxadiazol-3-yl]-2,6-dimethyl-phenol.

| Example | prepared in analogy to Example | R | LC-MS $t_R$ [min] | $[M + H]^+$ |
|---|---|---|---|---|
| 7 | 4 | ![O~NH2 OH] | 0.98* | 427.04 |
| 8 | 4 | ![O~NH2 OH] | 0.98* | 427.02 |
| 9 | 5 | ![O~N(H)C(O)CH2OH OH] | 0.86* | 485.26 |
| 10 | 5 | ![O~N(H)C(O)CH2OH OH] | 0.85* | 485.21 |

Example 10

$^1$H NMR (CDCl$_3$): δ 0.99 (d, J=6.5 Hz, 6H), 2.16-2.27 (m, 1H), 2.36 (s, 6H), 2.78 (d, J=7.3 Hz, 2H), 3.47-3.71 (m, 2H), 3.72-3.92 (m, 4H), 3.98 (s, 3H), 4.14-4.23 (m, 3H), 6.86 (d, J=2.3 Hz, 1H), 7.15 (t, J=5.3 Hz), 7.69 (d, J=2.0 Hz, 1H), 7.88 (s, 2H).

Example 11

2-Ethyl-4-[5-(6-isobutyl-4-methoxy-pyridin-2-yl)-[1,2,4]oxadiazol-3-yl]-6-methyl-phenol

The title compound is prepared in analogy to Example 2 starting from 6-isobutyl-4-methoxy-pyridine-2-carboxylic acid and 3-ethyl-4,N-dihydroxy-5-methyl-benzamidine; LC-MS: t$_R$=1.11 min, [M+H]$^+$=368.12; $^1$H NMR (CDCl$_3$): δ 0.99 (d, J=6.8 Hz, 6H), 1.32 (t, J=7.8 Hz, 3H), 2.24 (hept, J=6.8 Hz), 2.35 (s, 3H), 2.73 (q, J=7.8 Hz, 2H), 2.78 (d, J=7.3 Hz, 2H), 3.98 (s, 3H), 5.02 (s, 1H), 6.85 (d, J=1.3 Hz, 1H), 7.70 (d, J=1.3 Hz, 1H), 7.89 (s, 2H).

Examples 12 to 17

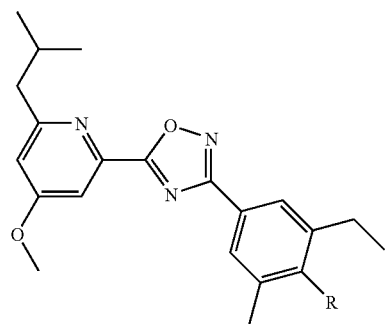

The following Examples are prepared in analogy to previous Examples starting from 2-ethyl-4-[5-(6-isobutyl-4-methoxy-pyridin-2-yl)-[1,2,4]oxadiazol-3-yl]-6-methyl-phenol.

| Example | prepared in analogy to Example | R | LC-MS t$_R$ [min] | [M + H]$^+$ |
|---|---|---|---|---|
| 12 | 3 | ![structure with OH groups, (R)-glycerol ether] | 1.01 | 442.12 |
| 13 | 3 | ![structure with OH groups, (S)-glycerol ether] | 1.01 | 442.11 |
| 14 | 4 | ![structure with OH and NH$_2$, (R)] | 1.02* | 441.26 |
| 15 | 4 | ![structure with OH and NH$_2$, (S)] | 0.86 | 441.27 |
| 16 | 5 | ![structure with glycolamide, (R)] | 0.96 | 499.11 |
| 17 | 5 | ![structure with glycolamide, (S)] | 0.97 | 499.19 |

Example 17

¹H NMR (CDCl₃): δ 0.99 (d, J=6.5 Hz, 6H), 1.31 (t, J=7.3 Hz, 3H), 2.18-2.28 (m, 1H), 2.37 (s, 3H), 2.73 (q, J=7.5 Hz, 2H), 2.78 (d, J=7.3 Hz, 2H), 3.01 (s br, 1H), 3.46-3.56 (m, 2H), 3.74-3.93 (m, 3H), 3.98 (s, 3H), 4.16-4.24 (m, 3H), 6.86 (s, 1H), 7.08 (s br, 1H), 7.70 (s, 1H), 7.90 (s, 1H), 7.91 (s, 1H).

Example 18

4-[5-(6-Isobutyl-4-methoxy-pyridin-2-yl)-[1,3,4]oxadiazol-2-yl]-2,6-dimethyl-phenol a) To a solution of 6-isobutyl-4-methoxy-pyridine-2-carboxylic acid (270 mg, 1.10 mmol), 4-benzyloxy-3,5-dimethyl-benzoic acid hydrazide (327 mg, 1.21 mmol) and DIPEA (455 mg, 3.52 mmol) in DCM (15 mL), PyBOP (858 mg, 1.65 mmol) is added at 0° C. The mixture is stirred for 30 min at rt, the reaction is diluted with diethyl ether and washed with 1 N aq. NaOH solution followed by 1 M aq. NaH₂PO₄ solution. The org. extract is dried over Na₂SO₄, filtered and concentrated to give the crude hydrazide intermediate; LC-MS: $t_R$=1.00 min, [M+H]⁺=462.23. This material (1.13 g) is dissolved in DCM (15 mL) and pyridine (1 mL) and the mixture is cooled to 0° C. before trifluoromethanesulfonic anhydride (1.38 g, 4.89 mmol) is added dropwise. The mixture is warmed to rt and stirring is continued for 16 h. The reaction is quenched by adding 3-dimethylamino-1-propylamine (50 mg, 0.49 mmol). The mixture is washed twice with 1 N aq. NaH₂PO₄ solution followed by water, dried over Na₂SO₄, filtered and concentrated. The crude product is purified by CC on silica gel eluting with heptane:EA 4:1 to give 2-[5-(4-benzyloxy-3,5-dimethyl-phenyl)-[1,3,4]oxadiazol-2-yl]-6-isobutyl-4-methoxy-pyridine (414 mg) as a yellow oil; LC-MS: $t_R$=1.15 min, [M+H]⁺=444.21.

b) The above benzyl ether (414 mg, 0.934 mmol) is dissolved in THF (5 mL) and methanol (5 mL) before Pd/C (200 mg, 10% Pd) is added. The slurry is hydrogenated at rt under 1 bar of H₂ for 72 h. The catalyst is removed by filtration and the filtrate is concentrated and dried to give the title compound (308 mg) as a white solid; LC-MS: $t_R$=0.77* min, [M+H]⁺=354.30; ¹H NMR (CDCl₃): δ 1.01 (d, J=6.5 Hz, 6H), 2.19-2.30 (m, 1H), 2.36 (s, 6H), 2.76 (d, J=7.3 Hz, 2H), 3.97 (s, 3H), 5.07 (s, 1H), 6.80 (d, J=2.3 Hz, 1H), 7.66 (d, J=2.3 Hz, 1H), 7.88 (s, 2H).

Examples 19 to 24

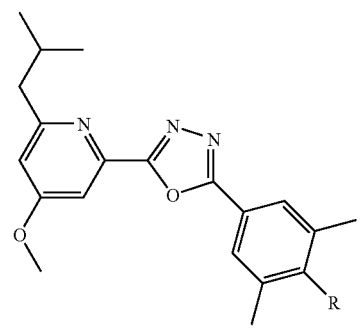

The following Examples are prepared starting from Example 18 in analogy to previous Examples.

| Example | prepared in analogy to Example | R | LC-MS $t_R$ [min] | [M + H]⁺ |
|---|---|---|---|---|
| 19 | 3 | O~~~OH / OH | 0.91* | 428.18 |
| 20 | 3 | O~~~OH / OH | 0.98 | 428.16 |
| 21 | 4 | O~~~NH₂ / OH | 0.84* | 427.07 |
| 22 | 4 | O~~~NH₂ / OH | 0.84* | 427.04 |
| 23 | 5 | O~~~N(H)C(O)CH₂OH / OH | 0.78* | 489.25 |
| 24 | 5 | O~~~N(H)C(O)CH₂OH / OH | 0.78 | 489.24 |

Example 20

¹H NMR (CDCl₃): δ 0.99 (d, J=6.8 Hz, 6H), 2.15 (s br, 1H), 2.19-2.27 (m, 1H), 2.39 (s, 6H), 2.78 (d, J=7.3 Hz, 2H), 3.82-3.97 (m, 5H), 3.98 (s, 3H), 4.13-4.20 (m, 1H), 6.86 (d, J=2.3 Hz, 1H), 7.70 (d, J=2.0 Hz, 1H), 7.91 (s, 2H).

Example 25

2-Ethyl-4-[5-(6-isobutyl-4-methoxy-pyridin-2-yl)-[1,3,4]oxadiazol-2-yl]-6-methyl-phenol The title compound is prepared in analogy to Example 18 starting from 6-isobutyl-4-methoxy-pyridine-2-carboxylic acid and 4-benzyloxy-3-ethyl-5-methyl-benzoic acid hydrazide; LC-MS: $t_R$=1.04 min, [M+H]⁺=368.33.

Examples 26 to 31

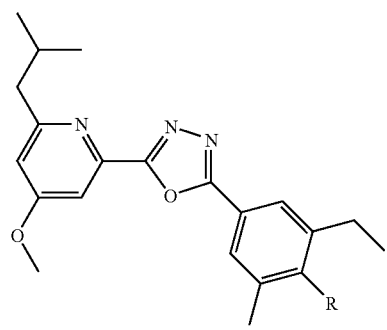

The following Examples are prepared starting from Example 25 in analogy to previous Examples.

| Example | prepared in analogy to Example | R | LC-MS $t_R$ [min] | [M + H]⁺ |
|---|---|---|---|---|
| 26 | 3 | O-CH₂-CH(OH)-CH₂-OH (S) | 0.94* | 442.24 |
| 27 | 3 | O-CH₂-CH(OH)-CH₂-OH (R) | 1.00 | 442.11 |
| 28 | 4 | O-CH₂-CH(OH)-CH₂-NH₂ (S) | 0.88* | 441.26 |
| 29 | 4 | O-CH₂-CH(OH)-CH₂-NH₂ (R) | 0.87* | 441.25 |
| 30 | 5 | O-CH₂-CH(OH)-CH₂-NH-C(O)-CH₂-OH (S) | 0.80* | 499.26 |
| 31 | 5 | O-CH₂-CH(OH)-CH₂-NH-C(O)-CH₂-OH (R) | 0.80* | 499.26 |

Example 31

$^1$H NMR (CDCl$_3$): δ 1.01 (d, J=6.5 Hz, 6H), 1.31 (t, J=7.5 Hz, 3H), 2.19-2.28 (m, 1H), 2.39 (s, 3H), 2.70-2.79 (m, 4H), 3.49-3.58 (m, 1H), 3.76-3.93 (m, 4H), 3.97 (s, 3H), 4.18-4.25 (m, 3H), 6.82 (d, J=2.0 Hz, 1H), 7.07 (s br, 1H), 7.66 (d, J=2.0 Hz, 1H), 7.90 (s, 1H), 7.91 (s, 1H).

Example 32

2-Ethyl-4-[5-(5-isobutyl-4-methyl-pyridin-2-yl)-[1,2,4]oxadiazol-3-yl]-6-methyl-phenol The title compound is prepared in analogy to Example 2 starting from 5-isobutyl-4-methyl-pyridine-2-carboxylic acid and 3-ethyl-4,N-dihydroxy-5-methyl-benzamidine; LC-MS: $t_R$=1.12 min, [M+H]$^+$=352.12.

Examples 33 to 36

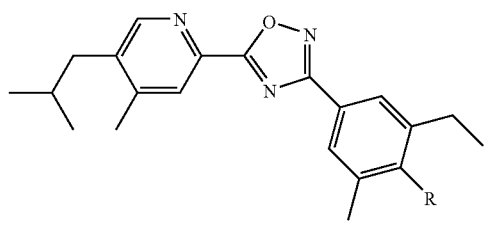

The following Examples are prepared starting from Example 32 in analogy to previous Examples.

| Example | prepared in analogy to Example | R | LC-MS $t_R$ [min] | [M + H]$^+$ |
|---|---|---|---|---|
| 33 | 3 | O~~~OH, OH | 1.02 | 426.12 |
| 34 | 3 | O~~~OH, OH | 1.01 | 426.45 |
| 35 | 3 | O~~~NH$_2$, OH | 0.86 | 425.46 |
| 36 | 5 | O~~~N(H)-C(O)-CH$_2$OH, OH | 0.98 | 483.16 |

Example 33

$^1$H NMR (CDCl$_3$): δ 1.00 (d, J=6.8 Hz, 6H), 1.32 (t, J=7.5 Hz, 3H), 1.89-2.01 (m, 1H), 2.10 (t br, J=5.8 Hz, 1H), 2.40 (s, 3H), 2.47 (s, 3H), 2.63 (d, J=7.3 Hz, 2H), 2.72-2.80 (m, 3H), 3.81-3.98 (m, 4H), 4.13-4.20 (m, 1H), 7.95 (s, 1H), 7.96 (s, 1H), 8.09 (s, 1H), 8.55 (s, 1H).

Example 36

$^1$H NMR (CDCl$_3$): δ 0.99 (d, J=6.8 Hz, 6H), 1.29 (t, J=7.5 Hz, 3H), 1.94 (hept, J=6.8 Hz), 2.36 (s, 3H), 2.46 (s, 3H), 2.62 (d, J=7.0 Hz, 2H), 2.72 (q, J=7.5 Hz, 2H), 3.37 (s br, 1H), 3.47-3.55 (m, 1H), 3.64 (s br, 2H), 3.74-3.92 (m, 3H), 4.16-4.24 (m, 3H), 7.16 (t, J=5.3 Hz, 1H), 7.91 (s, 1H), 7.93 (s, 1H), 8.09 (s, 1H), 8.53 (s, 1H).

Example 37

3-{2-Ethyl-4-[5-(5-isobutyl-4-methyl-pyridin-2-yl)-[1,2,4]oxadiazol-3-yl]-6-methyl-phenyl}-N-methyl-propionamide To a solution of 3-{2-ethyl-4-[5-(5-isobutyl-4-methyl-pyridin-2-yl)-[1,2,4]oxadiazol-3-yl]-6-methyl-phenyl}-propionic acid (40 mg 89 µmol) in DMF (5 mL), DIPEA (35 mg, 268 µmol) is added. The mixture is cooled to 0° C. before PyBOP (51 mg, 98 µmol) is added. The mixture is stirred at 0° C. for 15 min before methylamine (58 µL of a 2 M solution in THF) is added. The mixture is stirred at rt for 16 h, diluted with sat. aq. NaHCO$_3$ solution, and extracted twice with EA. The combined org. extracts are dried over MgSO$_4$, filtered and concentrated. The crude product is purified on prep. TLC plates using heptane:EA 1:4 to give the title compound (35 mg) as a white solid; LC-MS: $t_R$=1.10 min, [M+H]$^+$=421.25; $^1$H NMR (CDCl$_3$): δ 1.00 (d, J=6.5 Hz, 6H), 1.31 (t, J=7.3 Hz, 3H), 1.89-2.00 (m, 1H), 2.34-2.41 (m, 2H), 2.44 (s, 3H), 2.47 (s, 3H), 2.63 (d, J=7.0 Hz, 2H), 2.76 (q, J=7.8 Hz, 2H), 2.85 (d, J=4.5 Hz, 3H), 3.06-3.13 (m, 2H), 5.38 (s br, 1H), 7.91 (s, 1H), 7.93 (s, 1H), 8.10 (s, 1H), 8.55 (s, 1H).

Example 38

3-{2-Ethyl-4-[5-(5-isobutyl-4-methyl-pyridin-2-yl)-[1,2,4]oxadiazol-3-yl]-6-methyl-phenyl}-N-(2-hydroxy-ethyl)-propionamide The title compound is prepared in analogy to Example 37 using ethanolamine; LC-MS: $t_R$=1.02 min, [M+H]$^+$=451.23;

¹H NMR (CDCl₃): δ 1.00 (d, J=6.3 Hz, 6H), 1.31 (t, J=7.3 Hz, 3H), 1.89-2.01 (m, 1H), 2.37-2.45 (m, 6H), 2.47 (s, 3H), 2.63 (d, J=7.0 Hz, 2H), 2.73-2.81 (m, 2H), 3.07-3.14 (m, 2H), 3.44-3.50 (m, 2H), 3.73-3.79 (m, 2H), 5.84 (s br, 1H), 7.91 (s, 1H), 7.93 (s, 1H), 8.10 (s, 1H), 8.55 (s, 1H).

Example 39

N-(2-Amino-ethyl)-3-{2-ethyl-4-[5-(5-isobutyl-4-methyl-pyridin-2-yl)-[1,2,4]oxadiazol-3-yl]-6-methyl-phenyl}-propionamide a) [2-(3-{2-Ethyl-4-[5-(5-isobutyl-4-methyl-pyridin-2-yl)-[1,2,4]oxadiazol-3-yl]-6-methyl-phenyl}-propionylamino)-ethyl]-carbamic acid tert-butyl ester is prepared in analogy to Example 37 by coupling (2-amino-ethyl)-carbamic acid tert-butyl ester with 3-{2-ethyl-4-[5-(5-isobutyl-4-methyl-pyridin-2-yl)-[1,2,4]oxadiazol-3-yl]-6-methyl-phenyl}-propionic acid; LC-MS: $t_R$=1.14 min, [M+H]⁺=550.33.

b) A solution of the above tert.butyloxycarbonyl protected amine (44 mg, 80 μmol) in 4 M HCl in dioxane (5 mL) is stirred at rt for 18 h. The solvent is removed in vacuo and the crude product is purified on prep. TLC plates using DCM containing 4% of 7 N NH₃ in methanol to give the title compound as a white solid; LC-MS: $t_R$=0.89 min, [M+H]⁺=450.21.

Example 40

3-(3-{2-Ethyl-4-[5-(5-isobutyl-4-methyl-pyridin-2-yl)-[1,2,4]oxadiazol-3-yl]-6-methyl-phenyl}-propionylamino)-propionic acid a) 3-(3-{2-Ethyl-4-[5-(5-isobutyl-4-methyl-pyridin-2-yl)-[1,2,4]oxadiazol-3-yl]-6-methyl-phenyl}-propionylamino)-propionic acid tert-butyl ester is prepared in analogy to Example 37 by coupling 3-amino-propionic acid tert-butyl ester hydrochloride with 3-{2-ethyl-4-[5-(5-isobutyl-4-methyl-pyridin-2-yl)-[1,2,4]oxadiazol-3-yl]-6-methyl-phenyl}-propionic acid; LC-MS: $t_R$=1.18 min, [M+H]⁺=535.33.

b) A solution of the above tert.butyl ester (40 mg, 75 μmol) in 4 M HCl in dioxane (5 mL) is stirred at rt for 18 h before the solvent is evaporated. The crude product is purified on prep. TLC plates using DCM:methanol 9:1 to give the title compound (23 mg) as a white solid; LC-MS: $t_R$=1.03 min, [M+H]⁺=479.30; ¹H NMR (CDCl₃): δ 0.99 (d, J=6.3 Hz, 6H), 1.26 (t, J=7.8 Hz, 3H), 1.87-1.98 (m, 1H), 2.34-2.41 (m, 5H), 2.43-2.51 (m, 5H), 2.61 (d, J=6.8 Hz, 2H), 2.68-2.77 (m, 2H), 3.01-3.09 (m, 2H), 3.39-3.61 (m, 2H), 6.34 (s br, 1H), 7.82 (s, 1H), 7.84 (s, 1H), 8.06 (s, 1H), 8.52 (s, 1H).

Example 41

2-Ethyl-4-[5-(5-isobutyl-4-methyl-pyridin-2-yl)-[1,3,4]oxadiazol-2-yl]-6-methyl-phenol The title compound is prepared in analogy to Example 18 starting from 5-isobutyl-4-methyl-pyridine-2-carboxylic acid and 4-benzyloxy-3-ethyl-5-methyl-benzoic acid hydrazide; LC-MS: $t_R$=1.07 min, [M+H]⁺=357.18.

Examples 42 to 44

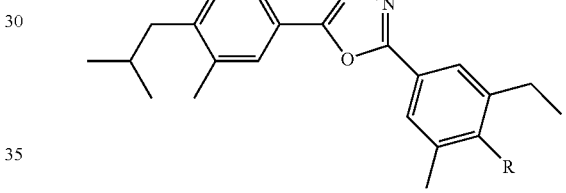

The following Examples are prepared starting from Example 41 in analogy to previous Examples.

| Example | prepared in analogy to Example | R | LC-MS $t_R$ [min] | [M + H]⁺ |
|---|---|---|---|---|
| 42 | 3 | ![structure] O-CH₂-CH(OH)-CH₂-OH | 0.96 | 426.15 |
| 43 | 4 | ![structure] O-CH₂-CH(OH)-CH₂-NH₂ | 0.83 | 425.27 |
| 44 | 5 | ![structure] O-CH₂-CH(OH)-CH₂-NH-C(O)-CH₂-OH | 0.92 | 483.23 |

Example 42

¹H NMR (CDCl₃): δ 1.00 (d, J=6.5 Hz, 6H), 1.31 (t, J=7.3 Hz, 3H), 1.94 (hept, J=6.5 Hz, 1H), 2.40 (s, 3H), 2.45 (s, 3H), 2.61 (d, J=7.0 Hz, 2H), 2.76 (q, J=7.5 Hz, 2H), 3.81-3.98 (m, 4H), 4.15-4.21 (m, 1H), 7.93 (s, 1H), 7.94 (s, 1H), 8.12 (s, 1H), 8.50 (s, 1H).

Example 45

2-Ethyl-4-[5-(6-isobutyl-4-methyl-pyridin-2-yl)-[1,2,4]oxadiazol-3-yl]-6-methyl-phenol The title compound (30 mg) is obtained as a pale yellow oil in analogy to Example 2 starting from 6-isobutyl-4-methyl-pyridine-2-carboxylic acid (100 mg, 435 μmol) and 3-ethyl-4,N-dihydroxy-5-methyl-benzamidine (85 mg, 435 μmol): LC-MS: $t_R$=1.13 min, [M+H]$^+$=352.28.

Example 46

(S)-3-{2-Ethyl-4-[5-(6-isobutyl-4-methyl-pyridin-2-yl)-[1,2,4]oxadiazol-3-yl]-6-methyl-phenoxy}-propane-1,2-diol The title compound (32 mg) is obtained as a colourless oil in analogy to Example 3 starting from Example 45 (30 mg, 85 μmol); LC-MS: $t_R$=1.07 min, [M+H]$^+$=426.49; $^1$H NMR (CDCl$_3$): δ0.98 (d, J=6.8 Hz, 6H), 1.31 (t, J=7.5 Hz, 3H), 2.22 (hept, J=7.0 Hz, 1H), 2.38 (s, 3H), 2.45 (s br, 1H), 2.47 (s, 3H), 2.75 (q, J=7.5 Hz, 2H), 2.79 (d, J=7.3 Hz, 2H), 3.00 (s br, 1H), 3.80-3.96 (m, 4H), 4.13-4.20 (m, 1H), 7.17 (s, 1H), 7.91 (s, 1H), 7.93 (s, 1H), 7.99 (s, 1H).

Example 47

2-{2-Ethyl-4-[5-(5-isobutyl-4-methyl-pyridin-2-yl)-[1,2,4]oxadiazol-3-yl]-6-methyl-phenoxy}-ethanol To a solution of the compound of Example 32 (1.00 g, 2.85 mmol) in isopropanol (10 mL) and 3 M aq. NaOH (3 mL), 2-bromo-ethanol (1.42 g, 11.4 mmol) is added. The mixture is stirred at 60° C. for 24 h before another portion of 2-bromo-ethanol (176 mg, 1.41 mmol) is added. Stirring is continued at 60° C. for 6 h. The mixture is diluted with EA and washed with water. The org. extract is dried over MgSO$_4$, filtered and concentrated. The crude product is purified by CC on silica gel eluting with heptane:EA 4:1 to 3:1 to give the title compound (900 mg) as a colourless oil; LC-MS: $t_R$=1.10 min, [M+H]$^+$=396.09.

Example 48

2-{2-Ethyl-4-[5-(5-isobutyl-4-methyl-pyridin-2-yl)-[1,2,4]oxadiazol-3-yl]-6-methyl-phenoxy}-ethylamine a) A solution of the compound of Example 47 (900 mg, 2.28 mmol) and triethylamine (322 mg, 3.18 mmol) in DCM (20 mL) is cooled to 0° C. before methanesulfonyl chloride (313 mg, 2.73 mmol) is added. The mixture is stirred at rt for 90 min. The mixture is diluted with DCM and washed with water. The org. extract is dried over MgSO$_4$, filtered and concentrated. The crude product is purified by CC on silica gel eluting with heptane:EA 1:1 to give methanesulfonic acid 2-{2-ethyl-4-[5-(5-isobutyl-4-methyl-pyridin-2-yl)-[1,2,4]oxadiazol-3-yl]-6-methyl-phenoxy}-ethyl ester (1.10 g) as a white solid; LC-MS: $t_R$=1.16 min, [M+H]$^+$=474.02.

b) A solution of the above methane sulfonic acid ester (318 mg, 671 μmol) in 7 N NH$_3$ in methanol (10 mL) is stirred in a sealed vial at 60° C. for 27 h. The solvent is evaporated and the crude product is purified on prep. TLC plates with DCM:methanol 9:1 to give the title compound (220 mg) as a colourless oil; LC-MS: $t_R$=0.86 min, [M+H]$^+$=395.08.

Example 49

1-(2-{2-Ethyl-4-[5-(5-isobutyl-4-methyl-pyridin-2-yl)-[1,2,4]oxadiazol-3-yl]-6-methyl-phenoxy}-ethyl)-azetidine-3-carboxylic acid A solution of methanesulfonic acid 2-{2-ethyl-4-[5-(5-isobutyl-4-methyl-pyridin-2-yl)-[1,2,4]oxadiazol-3-yl]-6-methyl-phenoxy}-ethyl ester (300 mg, 633 μmol), azetidine-3-carboxylic acid methyl ester (218 mg, 1.84 μmol) and triethylamine (129 mg, 1.26 mmol) in ethanol (10 mL) is stirred in a sealed vial at 80° C. for 96 h. The mixture is cooled to rt, diluted with 3 M aq. NaOH and again stirred at rt for 1 h. The mixture is acidified by adding aq. HCl and is then extracted with EA (2×25 mL). The org. extracts are combined, dried over MgSO$_4$, filtered and concentrated. The crude product is purified by prep. HPLC to give the title compound (170 mg) as a colourless oil; LC-MS: $t_R$=0.90 min, [M+H]$^+$=479.10; $^1$H NMR (CDCl$_3$): δ0.98 (d, J=6.5 Hz, 6H), 1.282 (t, J=7.0 Hz, 3H), 1.93 (hept, J=7.0 Hz, 1H), 2.38 (s, 3H), 2.45 (s, 3H), 2.61 (d, J=7.3 Hz, 2H), 2.73 (q, J=7.3 Hz, 2H), 3.71-3.82 (m, 2H), 3.97-4.08 (m, 1H), 4.19-4.27 (m, 2H), 4.37-4.62 (m, 2H), 4.73-4.97 (m, 2H), 7.87 (s, 1H), 7.89 (s, 1H), 8.07 (s, 1H), 8.53 (s, 1H).

Example 50

3-(2-{2-Ethyl-4-[5-(5-isobutyl-4-methyl-pyridin-2-yl)-[1,2,4]oxadiazol-3-yl]-6-methyl-phenoxy}-ethylamino)-propionic acid A solution of β-alanine ethyl ester hydrochloride (88 mg, 570 μmol) in ethanol (2 mL) is filtered over PL-HCO$_3$ MP SPE ion exchange. The methanesulfonic acid ester intermediate of Example 48 (90 mg, 190 μmol) and triethylamine (77 mg, 760 μmol) is added to the filtrate and the mixture is stirred in a sealed vial at 80° C. for 18 h. The mixture is cooled to rt and the solvent is evaporated. The crude 3-(2-{2-ethyl-4-[5-(5-isobutyl-4-methyl-pyridin-2-yl)-[1,2,4]oxadiazol-3-yl]-6-methyl-phenoxy}-ethylamino)-propionic acid ethyl ester is dissolved in ethanol (2 mL) and 1 N aq. NaOH (2 mL) and the mixture is stirred at rt for 3 h. The mixture is neutralised by adding 1 N aq. HCl, the solvent is removed in vacuo and the residue is separated by prep. HPLC to give the title compound (24 mg) as a white solid; LC-MS: $t_R$=0.90 min, [M+H]$^+$=466.79; $^1$H NMR (CDCl$_3$): δ1.00 (d, J=6.5 Hz, 6H), 1.30 (t, J=7.3 Hz, 3H), 1.90-1.99 (m, 1H), 2.38 (s, 3H), 2.46 (s, 3H), 2.60-2.68 (m, 4H), 2.73 (q, J=7.5 Hz, 2H), 3.20-3.27 (m, 2H), 3.27-3.33 (m, 2H), 4.07-4.15 (m, 2H), 7.92 (s, 1H), 7.94 (s, 1H), 8.08 (s, 1H), 8.54 (s, 1H).

Example 51

N-(2-{2-Ethyl-4-[5-(5-isobutyl-4-methyl-pyridin-2-yl)-[1,2,4]oxadiazol-3-yl]-6-methyl-phenoxy}-ethyl)-2-hydroxy-acetamide To a solution of the compound of Example 48 (50 mg, 127 μmol) in THF (2 mL) and DMF (2 mL), EDC hydrochloride (27 mg, 139 μmol), HOBt (19 mg, 139 μmol), DIPEA (25 mg, 190 μmol) and glycolic acid (11 mg, 139 μmol) is added. The mixture is stirred at rt for 1 h before it is concentrated and separated by prep. HPLC to give the title compound (32 mg) as a colourless oil; LC-MS: $t_R$=1.05 min, [M+H]$^+$=453.08; $^1$H NMR (CDCl): δ1.00 (d, J=6.5 Hz, 6H), 1.31 (t, J=7.3 Hz, 3H), 1.89-2.00 (m, 1H), 2.37 (s, 3H), 2.47 (s, 3H), 2.63 (d, J=7.0 Hz, 2H), 2.73 (q, J=7.5 Hz, 2H), 3.75-3.83 (m, 2H), 3.93-3.99 (m, 2H), 4.23 (s, 2H), 7.03-7.15 (m, 1H), 7.94 (s, 2H), 8.09 (s, 1H), 8.55 (s, 1H).

Example 52

N-(2-{2-Ethyl-4-[5-(5-isobutyl-4-methyl-pyridin-2-yl)-[1,2,4]oxadiazol-3-yl]-6-methyl-phenoxy}-ethyl)-2-methylamino-acetamide To a solution of the compound of Example 48 (50 mg, 127 μmol) in THF (2 mL) and DMF (2 mL), EDC hydrochloride (27 mg, 139 μmol), HOBt (19 mg, 139 μmol), DIPEA (25 mg, 190 μmol) and BOC-sarcosine (26 mg, 139 μmol) is added. The mixture is stirred at rt for 1 h before it is concentrated. The residue is dissolved in 4 M HCl in dioxane (2 mL) and the mixture is stirred at rt for 30 min, concentrated and separated by prep. HPLC to give the title compound (23 mg) as a reddish oil; LC-MS: $t_R$=0.89 min, [M+H]$^+$=466.05.

Example 53

Ethanesulfonic acid (2-{2-ethyl-4-[5-(5-isobutyl-4-methyl-pyridin-2-yl)-[1,2,4]oxadiazol-3-yl]-6-methyl-phenoxy}-ethyl)-amide A solution of the methanesulfonic acid ester intermediate of Example 48 (25 mg, 53 μmol) and ethanesulfonamide potassium salt (16 mg, 106 μmol) in DMF (2 mL) is stirred at 60° C. for 18 h. The mixture is concentrated and separated by prep. HPLC to give the title compound (5 mg) as a colourless oil; LC-MS: $t_R$=1.14 min, [M+H]$^+$=487.14.

Example 54

N-(2-{2-ethyl-4-[5-(5-isobutyl-4-methyl-pyridin-2-yl)-[1,2,4]oxadiazol-3-yl]-6-methyl-phenoxy}-ethyl)-1-N',N'-dimethyl-sulfamic acid amide To a solution of the compound of Example 48 (100 mg, 253 μmol) and DIPEA (39 mg, 304 μmol) in acetonitrile (2 mL), N,N-dimethylsulfamoyl chloride (40 mg, 279 μmol) is added. The mixture is stirred at 60° C. for 18 h. The solvent is removed in vacuo and the crude product is purified by prep. HPLC to give the title compound (47 mg) as a white solid; LC-MS: $t_R$=1.16 min, [M+H]$^+$=502.17; $^1$H NMR (CDCl$_3$): δ1.00 (d, J=6.5 Hz, 6H), 1.32 (t, J=7.5 Hz, 3H), 1.89-2.01 (m, 1H), 2.39 (s, 3H), 2.47 (s, 3H), 2.63 (d, J=7.3 Hz, 2H), 2.75 (q, J=7.5 Hz, 2H), 2.89 (s, 6H), 3.51 (q, J=5.3 Hz, 2H), 3.98 (t, J=5.0 Hz, 2H), 4.75 (t, J=6.0 Hz, 1H), 7.95 (s, 1H), 7.96 (s, 1H), 8.09 (s, 1H), 8.55 (s, 1H).

Example 55

2-{2-Ethyl-4-[5-(5-isobutyl-4-methyl-pyridin-2-yl)-[1,2,4]oxadiazol-3-yl]-6-methyl-phenoxy}-propane-1,3-diol To a solution of the compound of Example 32 (100 mg, 285 μmol) in acetonitrile (2 mL), K$_2$CO$_3$ (56 mg, 427 μmol) followed by dimethyl chloromalonate (57 mg, 341 μmol) is added. The mixture is stirred at 65° C. for 18 h. The mixture is diluted with EA and washed with water. The org. extract is concentrated and the crude product is purified on prep. TLC plates using heptane:EA 4:1 to give 2-{2-ethyl-4-[5-(5-isobutyl-4-methyl-pyridin-2-yl)oxadiazol-3-yl]-6-methyl-phenoxy}-malonic acid dimethyl ester (95 mg) as a colourless oil; LC-MS: $t_R$=1.17 min, [M+H]$^+$=482.01. This material (95 mg, 197 μmol) is dissolved in ethanol (10 mL) and treated with NaBH$_4$ (60 mg, 1.58 mmol). The mixture is stirred at 60° C. for 1 h before the reaction is quenched with water. The mixture is extracted twice with EA and the combined extracts are concentrated. The crude product is purified on prep. TLC plates using heptane:EA 1:1 to give the title compound (44 mg) as a colourless oil; LC-MS: $t_R$=1.02 min, [M+H]$^+$=426.01; $^1$H NMR (CDCl$_3$): δ1.00 (d, J=6.5 Hz, 6H), 1.31 (t, J=7.3 Hz, 3H), 1.95 (hept, J=6.3 Hz, 1H), 2.08 (t br, J=5.5 Hz, 2H), 2.42 (s, 3H), 2.47 (s, 3H), 2.63 (d, J=7.0 Hz, 2H), 2.80 (q, J=7.5 Hz, 2H), 3.91-4.05 (m, 4H), 4.19 (quint, J=4.5 Hz, 1H), 7.95 (s, 1H), 7.98 (s, 1H), 8.10 (s, 1H), 8.55 (s, 1H).

Example 56

2-{2-Ethyl-4-[5-(5-isobutyl-4-methyl-pyridin-2-yl)-[1,2,4]oxadiazol-3-yl]-6-methyl-phenoxymethyl}-propane-1,3-diol 2-{3-[4-(2,2-Dimethyl-[1,3]dioxan-5-ylmethoxy)-3-ethyl-5-methyl-phenyl]-[1,2,4]oxadiazol-5-yl}-5-isobutyl-4-methyl-pyridine (200 mg) is obtained as a colourless oil in analogy to Example 1 staring from 4-(2,2-dimethyl-[1,3]dioxan-5-ylmethoxy)-3-ethyl-N-hydroxy-5-methyl-benzamidine (281 mg, 871 μmol) and 5-isobutyl-4-methyl-pyridine-2-carboxylic acid (200 mg, 871 μmol); LC-MS: $t_R$=1.24 min, [M+H]$^+$=480.20. This material (200 mg, 417 μmol) is dissolved in 4 M HCl in dioxane (5 mL) and the mixture is stirred at rt for 18 h. The solvent is evaporated and the crude product is purified on prep. TLC using heptane:EA 1:1 to give the title compound as a colourless oil; LC-MS: $t_R$=1.06 min, [M+H]$^+$=440.05; $^1$H NMR (CDCl$_3$): δ1.00 (d, J=6.5 Hz, 6H), 1.31 (t, J=7.5 Hz, 3H), 1.90-2.00 (m, 1H), 2.27-2.35 (m, 1H), 2.39 (s, 3H), 2.47 (s, 3H), 2.63 (d, J=7.3 Hz, 2H), 2.75 (q, J=7.8 Hz, 2H), 3.94-4.04 (m, 4H), 4.05 (d, J=5.5 Hz, 4H), 7.94 (s, 1H), 7.95 (s, 1H), 8.09 (s, 1H), 8.55 (s, 1H).

Example 57

(S)-1-{2-Ethyl-4-[5-(5-isobutyl-4-methyl-pyridin-2-yl)-[1,2,4]oxadiazol-3-yl]-6-methyl-phenoxy}-3-methylamino-propan-2-ol a) To a solution of the compound of Example 32 (315 mg, 896 μmol) in isopropanol (10 mL) and 3 N aq. NaOH (2 mL), (R)-epichlorohydrin (249 mg, 2.69 mmol) is added. The mixture is stirred at rt for 18 h before another portion of (R)-epichlorohydrin (249 mg, 2.69 mmol) is added. Stirring is continued at rt for 24 h. The mixture is diluted with EA and washed with water. The org. extract is concentrated and the crude product is purified on prep. TLC plates using heptane:EA 7:3 to give 2-[3-((S)-3-ethyl-5-methyl-4-oxiranylmethoxy-phenyl)-[1,2,4]oxadiazol-5-yl]-5-isobutyl-4-methyl-pyridine (233 mg) as a colourless oil; LC-MS: $t_R$=1.18 min, [M+H]$^+$=408.09.

b) A solution of the above epoxide intermediate (20 mg, 49 μmol) in 41% methylamine in water (2 mL) and DMF (0.5 mL) is stirred at 80° C. for 18 h. The solvent is removed in vacuo and the crude product is separated by prep. HPLC to give the title compound (6 mg) as a reddish oil; LC-MS: $t_R$=0.89 min, [M+H]$^+$=439.07.

Example 58

1-{2-Ethyl-4-[5-(5-isobutyl-4-methyl-pyridin-2-yl)-[1,2,4]oxadiazol-3-yl]-6-methyl-phenoxy}-3-((2S)-2-hydroxy-ethylamino)-propan-2-ol A solution of the epoxide intermediate of Example 57 (step a, 25 mg, 61 μmol) and ethanolamine (19 mg, 18 μmol) in ethanol (5 mL) is stirred at 60° C. for 18 h. The solvent is removed in vacuo and the crude product is purified by prep. HPLC to give the title compound (9 mg) as a white solid; LC-MS: $t_R$=0.87 min, [M+H]$^+$=469.12.

Example 59

Ethanesulfonic acid ((2S)-3-{2-ethyl-4-[5-(5-isobutyl-4-methyl-pyridin-2-yl)-[1,2,4]oxadiazol-3-yl]-6-methyl-phenoxy}-2-hydroxy-propyl)-amide A solution of the epoxide intermediate of Example 57 (step a, 25 mg, 61 µmol) and ethanesulfonamide potassium salt (27 mg, 184 µmol) in DMF (2 mL) is stirred at 60° C. for 18 h. The solvent is removed in vacuo and the crude product is purified by prep. HPLC to give the title compound (8 mg) as a colourless oil; LC-MS: $t_R$=1.07 min, [M+H]$^+$=517.12.

Example 60

3-((2S)-3-{2-Ethyl-4-[5-(5-isobutyl-4-methyl-pyridin-2-yl)-[1,2,4]oxadiazol-3-yl]-6-methyl-phenoxy}-2-hydroxy-propylamino)-propionic acid methyl ester A solution of the epoxide intermediate of Example 57 (step a, 150 mg, 368 µmol), β-alanine methyl ester hydrochloride (113 mg, 736 µmol) and triethylamine (93 mg, 920 µmol) in methanol (5 mL) is stirred at 60° C. for 20 h. The solvent is removed in vacuo and the crude product is purified on prep. TLC plates using DCM:methanol 10:1 to give the title compound (53 mg) as a colourless oil; LC-MS: $t_R$=0.92 min, [M+H]$^+$=511.18.

Example 61

3-((2S)-3-{2-Ethyl-4-[5-(5-isobutyl-4-methyl-pyridin-2-yl)-[1,2,4]oxadiazol-3-yl]-6-methyl-phenoxy}-2-hydroxy-propylamino)-propionic acid A solution of the compound of Example 60 (53 mg, 101 µmol) in ethanol (1 mL) and 1 M aq. NaOH (1 mL) is stirred at rt for 18 h. The ethanol is evaporated, the remaining solution is neutralized by adding 1 N aq. HCl, and the mixture is separated by prep. HPLC to give the title compound (23 mg) as a white solid; LC-MS: $t_R$=0.88 min, [M+H]$^+$=497.08; $^1$H NMR (CDCl$_3$): δ0.98 (d, J=6.5 Hz, 6H), 1.27 (t, J=7.3 Hz, 3H), 1.93 (hept, J=7.0 Hz, 1H), 2.34 (s, 3H), 2.44 (s, 3H), 2.60 (d, J=7.3 Hz, 2H), 2.65-2.83 (m, 4H), 3.18-3.40 (m, 3H), 3.82-3.96 (m, 2H), 4.52-4.61 (m, 1H), 7.88 (s, 1H), 7.92 (s, 1H), 8.06 (s, 1H), 8.51 (s, 1H).

Example 62

(S)-3-(2-Ethyl-4-{5-[6-(1-ethyl-propyl)-4-methyl-pyridin-2-yl]-[1,2,4]oxadiazol-3-yl}-6-methyl-phenoxy)-propane-1,2-diol 2-{(R)-3-[4-(2,2-Dimethyl-[1,3]dioxolan-4-ylmethoxy)-3-ethyl-5-methyl-phenyl]-[1,2,4]oxadiazol-5-yl}-6-(1-ethyl-propyl)-4-methyl-pyridine (42 mg) is prepared by coupling and cyclizing 6-(1-ethyl-propyl)-4-methyl-pyridine-2-carboxylic acid (67 mg, 323 µmol) with (R)-4-(2,2-dimethyl-[1,3]dioxolan-4-ylmethoxy)-3-ethyl-N-hydroxy-5-methyl-benzamidine (130 mg, 420 µmol) as described in Example 1. This material is dissolved in dioxane (5 mL) and 2 M aq. HCl (1 mL) and the mixture is stirred at rt for 16 h. The mixture is concentrated and the crude product is purified on prep. TLC using DCM containing 10% of 7 N NH$_3$ in methanol to give the title compound (25 mg) as a pale yellow glass; LC-MS**: $t_R$=0.80 min, [M+H]$^+$=440.27; $^1$H NMR (CDCl$_3$): δ0.85 (t, J=7.3 Hz, 6H), 1.32 (t, J=7.3 Hz, 3H), 1.79 (quint, J=7.3 Hz, 4H), 2.40 (s, 3H), 2.49 (s, 3H), 2.72-2.83 (m, 4H), 3.82-4.00 (m, 5H), 4.13-4.21 (m, 1H), 7.16 (s, 1H), 7.91 (s, 1H), 7.92 (s, 1H), 8.00 (s, 1H).

Example 63

N—[(S)-3-(2-Ethyl-4-{5-[6-(1-ethyl-propyl)-4-methyl-pyridin-2-yl]-[1,2,4]oxadiazol-3-yl}-6-methyl-phenoxy)-2-hydroxy-propyl]-2-hydroxy-acetamide The title compound (35 mg) is prepared by coupling and cyclizing 6-(1-ethyl-propyl)-4-methyl-pyridine-2-carboxylic acid (67 mg, 323 µmol) and N—((S)-3-[2-ethyl-4-(N-hydroxycarbamimidoyl)-6-methyl-phenoxy]-2-hydroxy-propyl)-2-hydroxy-acetamide (137 mg, 420 µmol) as described in Example 1; LC-MS*: $t_R$=1.01 min, [M+H]$^+$=497.23; $^1$H NMR (CDCl$_3$): δ0.85 (t, J=7.5 Hz, 6H), 1.31 (t, J=7.3 Hz, 3H), 1.79 (quint, J=7.0 Hz, 4H), 2.38 (s, 3H), 2.49 (s, 3H), 2.70-2.80 (m, 3H), 3.48-3.56 (m, 2H), 3.75-3.93 (m, 3H), 4.18-4.24 (m, 3H), 7.11 (t, J=5.5 Hz, 1H), 7.16 (s, 1H), 7.90 (s, 1H), 7.91 (s, 1H), 8.00 (s, 1H).

Examples 64 to 68

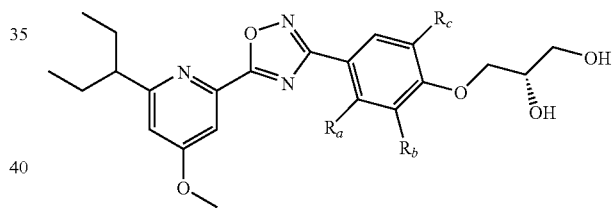

The following Examples are prepared in analogy to Example 62 starting from 6-(1-ethyl-propyl)-4-methoxy-pyridine-2-carboxylic acid and the appropriate 4-(2,2-dimethyl-[1,3]dioxolan-4-ylmethoxy)-N-hydroxy-benzamidine

| | | | | LC-MS** | |
| Example | $R_a$ | $R_b$ | $R_c$ | $t_R$ [min] | [M + H]$^+$ |
|---|---|---|---|---|---|
| 64 | H | CH$_3$ | CH$_2$CH$_3$ | 0.78 | 456.32 |
| 65 | H | CH$_3$ | Cl | 0.78 | 462.17 |
| 66 | H | CH$_3$ | OCH$_3$ | 0.75 | 458.29 |
| 67 | H | OCH$_3$ | Cl | 0.77 | 478.18 |
| 68 | OCH$_3$ | H | H | 0.68 | 444.21 |

Example 64

$^1$H NMR (CDCl$_3$): δ0.87 (t, J=7.3 Hz, 6H), 1.33 (t, J=7.5 Hz, 3H), 1.79 (quint, J=7.3 Hz, 4H), 2.09 (t br, J=5.3 Hz, 1H), 2.41 (s, 3H), 2.72-2.81 (m, 4H), 3.82-3.94 (m, 2H), 3.94-3.97

(m, 2H), 3.99 (s, 3H), 4.14-4.20 (m, 1H), 6.85 (d, J=2.3 Hz, 1H), 7.71 (d, J=2.3 Hz, 1H), 7.92 (s, 1H), 7.92 (s, 1H).

Examples 69 to 72

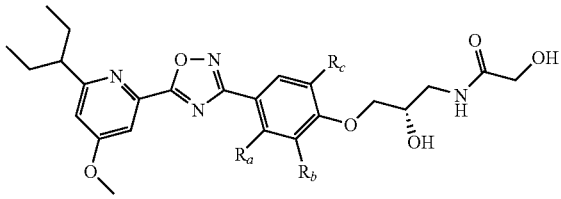

The following Examples are prepared in analogy to Example 62 starting from 6-(1-ethyl-propyl)-4-methoxy-pyridine-2-carboxylic acid and the appropriate 2-hydroxy-N-{2-hydroxy-3-[4-(N-hydroxycarbamimidoyl)-phenoxy]-propyl}-acetamide.

| Example | $R_a$ | $R_b$ | $R_c$ | LC-MS** $t_R$ [min] | $[M + H]^+$ |
|---|---|---|---|---|---|
| 69 | H | $CH_3$ | $CH_2CH_3$ | 0.75 | 513.80 |
| 70 | H | $CH_3$ | $CH_3$ | 0.73 | 499.22 |
| 71 | H | $CH_3$ | Cl | 0.75 | 519.25 |
| 72 | H | $CH_3$ | $OCH_3$ | 0.72 | 515.20 |

Example 69

$^1$H NMR (CDCl$_3$): δ0.86 (t, J=7.5 Hz, 6H), 1.31 (t, J=7.5 Hz, 3H), 1.78 (quint, J=7.3 Hz, 4H), 2.38 (s, 3H), 2.71-2.79 (m, 3H), 2.92 (s br, 1H), 3.45-3.56 (m, 2H), 3.76-3.81 (m, 1H), 3.84 (dd, J=9.5, 6.3 Hz, 1H), 3.90 (dd, J=9.5, 4.8 Hz, 1H), 3.99 (s, 3H), 4.19-4.24 (m, 3H), 6.85 (d, J=2.3 Hz, 1H), 7.07 (t, J=5.3 Hz), 7.71 (d, J=2.3 Hz, 1H), 7.90 (s, 1H), 7.91 (s, 1H).

Example 73

4-{5-[6-(1-Ethyl-propyl)-4-methoxy-pyridin-2-yl]-[1,2,4]oxadiazol-3-yl}-2-methyl-6-propyl-phenol The title compound (3 mg) is prepared by coupling and cyclizing 6-(1-ethyl-propyl)-4-methoxy-pyridine-2-carboxylic acid hydrochloride (64 mg, 246 μmol) and 4,N-dihydroxy-3-methyl-5-propyl-benzamidine (54 mg, 259 μmol) as described in Example 1; LC-MS**: $t_R$=0.88 min, $[M+H]^+$= 396.29.

Example 74

N-((2S)-3-{2-Ethyl-4-[3-(5-isobutyl-4-methyl-pyridin-2-yl)-[1,2,4]oxadiazol-5-yl]-6-methyl-phenoxy}-2-hydroxy-propyl)-2-hydroxy-acetamide The title compound (32 mg) is prepared by coupling and cyclizing N-hydroxy-5-isobutyl-4-methyl-pyridine-2-carboxamidine (40 mg, 193 μmol) with 3-ethyl-4-[(S)-2-hydroxy-3-(2-hydroxy-acetylamino)-propoxy]-5-methyl-benzoic acid (60 mg, 193 μmol) as described in Example 1; LC-MS: $t_R$=0.95 min, $[M+H]^+$=482.86.

Example 75

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order #6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay. The EC$_{50}$ values of the compounds of Examples 2, 6, 7, 8, 11, 14, 15, 21, 22, 28, 29, 45 and 60 have not been measured. Agonistic activities (EC$_{50}$ values) of all other exemplified compounds have been measured. The measured EC$_{50}$ value of the compound of Example 43 was greater than 10 μM. EC$_{50}$ values of all other exemplified compounds are in the range of 0.2 to 7600 nM with an average of 345 nM. Agonistic activities of some compounds of Formula (I) are displayed in Table 1.

TABLE 1

| Compound of Example | EC$_{50}$ [nM] |
|---|---|
| 1 | 1.2 |
| 10 | 2.7 |
| 17 | 2.3 |
| 33 | 7.2 |
| 34 | 9.1 |
| 40 | 3.3 |
| 50 | 5.1 |
| 51 | 8.8 |
| 55 | 4.7 |
| 58 | 11.2 |
| 59 | 11.9 |
| 61 | 2.3 |
| 62 | 2.2 |
| 65 | 9.4 |
| 69 | 3.1 |
| 70 | 2.8 |
| 71 | 0.8 |
| 72 | 8.8 |
| 74 | 9.0 |

Example 76

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of some compounds of Formula (I) to normotensive male Wistar rats as compared to a group of animals treated with vehicle only. Lymphocyte counts 6 h after oral administration have been measured for 7 of the exemplified compounds (Table 2) and are in the range of −35% to −74% with an average of −64%.

TABLE 2

| Compound of Example | Lymphocyte counts |
| --- | --- |
| 1 | −74% |
| 5 | −67% |
| 17 | −66% |
| 34 | −70% |
| 36 | −74% |
| 40 | −35% |
| 55 | −65%* |

*3 h after administration.

The invention claimed is:
1. A compound of the Formula (I),

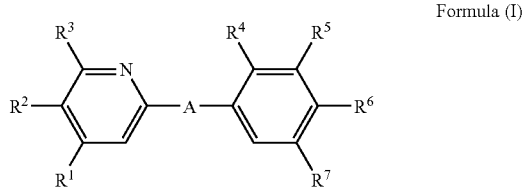

Formula (I)

wherein
A represents

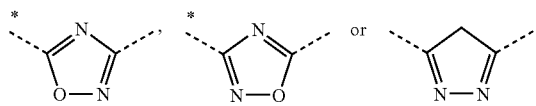

wherein the asterisks indicate the bond that is linked to the pyridine group of Formula (I);
$R^1$ represents methyl, ethyl or methoxy; $R^2$ represents hydrogen; and $R^3$ represents $C_{2-5}$-alkyl or $C_{1-4}$-alkoxy; or
$R^1$ represents $C_{2-5}$-alkyl or $C_{1-4}$-alkoxy; $R^2$ represents hydrogen; and $R^3$ represents methyl or ethyl; or
$R^1$ represents methyl, ethyl, or methoxy; $R^2$ represents $C_{3-5}$-alkyl; and $R^3$ represents hydrogen;
$R^4$ represents hydrogen or methoxy;
$R^5$ represents hydrogen, $C_{1-3}$-alkyl, or methoxy;
$R^6$ represents —$CH_2$—$(CH_2)_n$—$CONR^{61}R^{62}$, hydroxy, hydroxy-$C_{2-4}$-alkoxy, di-(hydroxy-$C_{1-2}$-alkyl)-$C_{1-2}$-alkoxy, 2,3-dihydroxy-propoxy, —$OCH_2$—$(CH_2)_n$—$NR^{61}R^{62}$, —$OCH_2$—$CH(OH)$—$CH_2$—$NR^6R^6$, —$OCH_2$—$(CH_2)_n$—$NHSO_2R^{63}$, —$OCH_2$—$CH(OH)$—$CH_2$—$NHSO_2R^{63}$, —$OCH_2$—$(CH_2)_n$—$NHCOR^{64}$, or —$OCH_2$—$CH(OH)$—$CH_2$—$NHCOR^{64}$;
$R^{61}$ represents hydrogen, methyl, ethyl, 2-hydroxyethyl, carboxymethyl, 1-($C_{1-5}$-alkylcarboxy)methyl, 2-carboxyethyl, 2-($C_{1-5}$-alkylcarboxy)ethyl, 2-aminoethyl, or 2-methylamino-ethyl;
$R^{62}$ represents hydrogen, or methyl;
$R^{63}$ represents $C_{1-3}$-alkyl, methylamino, ethylamino, or dimethylamino;
$R^{64}$ represents hydroxymethyl, 2-hydroxyethyl, aminomethyl, methylaminomethyl, 2-aminoethyl, or 2-methylamino-ethyl;
n represents the integer 1, or 2; and
$R^7$ represents hydrogen, methyl or chloro;
or a salt thereof.

2. The compound according to claim 1, wherein A represents

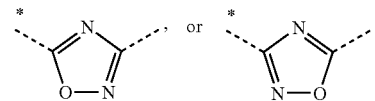

wherein the asterisks indicate the bond that is linked to the pyridine group of Formula (I);
or a salt thereof.

3. The compound according to claim 1, wherein A represents

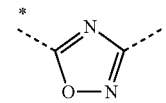

wherein the asterisk indicates the bond that is linked to the pyridine group of Formula (I);
or a salt thereof.

4. The compound according to claim 1, wherein $R^1$ represents methyl or methoxy, $R^2$ represents hydrogen, and $R^3$ represents $C_{2-4}$-alkyl or $C_{1-3}$-alkoxy; or a salt thereof.

5. The compound according to claim 1, wherein $R^1$ represents $C_{2-4}$-alkyl or $C_{1-3}$-alkoxy, $R^2$ represents hydrogen, and $R^3$ represents methyl; or a salt thereof.

6. The compound according to claim 1, wherein $R^1$ represents methyl, $R^2$ represents $C_4$-alkyl, and $R^3$ represents hydrogen; or a salt thereof.

7. The compound according to claim 1, wherein at least one of $R^4$, $R^5$ and $R^7$ represents a group other than hydrogen; or a salt thereof.

8. The compound according to claim 1, wherein $R^4$ represents methoxy, and $R^5$ and $R^7$ represent hydrogen; or a salt thereof.

9. The compound according to claim 1, wherein $R^4$ represents hydrogen, $R^5$ represents $C_{1-3}$-alkyl or methoxy, and $R^7$ represents methyl or chloro; or a salt thereof.

10. The compound according to claim 1, wherein $R^6$ represents —$CH_2$—$(CH_2)_n$—$CONR^{61}R^{62}$, di-(hydroxy-$C_{1-2}$-alkyl)-$C_{1-2}$-alkoxy, 2,3-dihydroxy-propoxy, —$OCH_2$—$(CH_2)_n$—$NR^{61}R^{62}$, —$OCH_2$—$CH(OH)$—$CH_2$—$NR^{61}R^{62}$, or —$OCH_2$—$CH(OH)$—$CH_2$—$NHCOR^{64}$;
or a salt thereof.

11. The compound according to claim 1, wherein $R^6$ represents 2,3-dihydroxy-propoxy, or —OCH$_2$—CH(OH)—CH$_2$—NHCOR$^{64}$; or a salt thereof.

12. The compound according to claim 1 selected from the group consisting of:
- N—((S)-3-{2-ethyl-4-[5-(6-isobutyl-4-methyl-pyridin-2-yl)-[1,2,4]oxadiazol-3-yl]-6-methyl-phenoxy}-2-hydroxy-propyl)-2-hydroxy-acetamide;
- N—((S)-3-{2-ethyl-4-[5-(4-isobutyl-6-methyl-pyridin-2-yl)-[1,2,4]oxadiazol-3-yl]-6-methyl-phenoxy}-2-hydroxy-propyl)-2-hydroxy-acetamide;
- 2-hydroxy-N—((R)-2-hydroxy-3-{4-[5-(6-isobutyl-4-methoxy-pyridin-2-yl)-[1,2,4]oxadiazol-3-yl]-2,6-dimethyl-phenoxy}-propyl)-acetamide;
- 2-hydroxy-N—((S)-2-hydroxy-3-{4-[5-(6-isobutyl-4-methoxy-pyridin-2-yl)-[1,2,4]oxadiazol-3-yl]-2,6-dimethyl-phenoxy}-propyl)-acetamide;
- N—((S)-3-{2-ethyl-4-[5-(6-isobutyl-4-methoxy-pyridin-2-yl)-[1,2,4]oxadiazol-3-yl]-6-methyl-phenoxy}-2-hydroxy-propyl)-2-hydroxy-acetamide;
- (S)-3-{4-[5-(6-isobutyl-4-methoxy-pyridin-2-yl)-[1,3,4]oxadiazol-2-yl]-2,6-dimethyl-phenoxy}-propane-1,2-diol;
- (R)-3-{2-ethyl-4-[5-(5-isobutyl-4-methyl-pyridin-2-yl)-[1,2,4]oxadiazol-3-yl]-6-methyl-phenoxy}-propane-1,2-diol;
- (S)-3-{2-ethyl-4-[5-(5-isobutyl-4-methyl-pyridin-2-yl)-[1,2,4]oxadiazol-3-yl]-6-methyl-phenoxy}-propane-1,2-diol;
- N—((S)-3-{2-ethyl-4-[5-(5-isobutyl-4-methyl-pyridin-2-yl)-[1,2,4]oxadiazol-3-yl]-6-methyl-phenoxy}-2-hydroxy-propyl)-2-hydroxy-acetamide;
- 3-{2-ethyl-4-[5-(5-isobutyl-4-methyl-pyridin-2-yl)-[1,2,4]oxadiazol-3-yl]-6-methyl-phenyl}-N-(2-hydroxy-ethyl)-propionamide; and
- 3-(3-{2-ethyl-4-[5-(5-isobutyl-4-methyl-pyridin-2-yl)-[1,2,4]oxadiazol-3-yl]-6-methyl-phenyl}-propionylamino)-propionic acid;

or a salt of such a compound.

13. The compound according to claim 1 selected from the group consisting of:
- 2-{2-ethyl-4-[5-(5-isobutyl-4-methyl-pyridin-2-yl)-[1,2,4]oxadiazol-3-yl]-6-methyl-phenoxy}-ethylamine;
- 3-(2-{2-ethyl-4-[5-(5-isobutyl-4-methyl-pyridin-2-yl)-[1,2,4]oxadiazol-3-yl]-6-methyl-phenoxy}-ethylamino)-propionic acid;
- N-(2-{2-ethyl-4-[5-(5-isobutyl-4-methyl-pyridin-2-yl)-[1,2,4]oxadiazol-3-yl]-6-methyl-phenoxy}-ethyl)-2-hydroxy-acetamide;
- 2-{2-ethyl-4-[5-(5-isobutyl-4-methyl-pyridin-2-yl)-[1,2,4]oxadiazol-3-yl]-6-methyl-phenoxy}-propane-1,3-diol;
- (S)-1-{2-ethyl-4-[5-(5-isobutyl-4-methyl-pyridin-2-yl)-[1,2,4]oxadiazol-3-yl]-6-methyl-phenoxy}-3-(2-hydroxy-ethylamino)-propan-2-ol;
- ethanesulfonic acid ((S)-3-{2-ethyl-4-[5-(5-isobutyl-4-methyl-pyridin-2-yl)-[1,2,4]oxadiazol-3-yl]-6-methyl-phenoxy}-2-hydroxy-propyl)-amide;
- 3-((S)-3-{2-ethyl-4-[5-(5-isobutyl-4-methyl-pyridin-2-yl)-[1,2,4]oxadiazol-3-yl]-6-methyl-phenoxy}-2-hydroxy-propylamino)-propionic acid;
- (S)-3-(2-ethyl-4-{5-[6-(1-ethyl-propyl)-4-methyl-pyridin-2-yl]-[1,2,4]oxadiazol-3-yl}-6-methyl-phenoxy)-propane-1,2-diol;
- N—[(S)-3-(2-ethyl-4-{5-[6-(1-ethyl-propyl)-4-methyl-pyridin-2-yl]-[1,2,4]oxadiazol-3-yl}-6-methyl-phenoxy)-2-hydroxy-propyl]-2-hydroxy-acetamide;
- (S)-3-(2-Ethyl-4-{5-[6-(1-ethyl-propyl)-4-methoxy-pyridin-2-yl]-[1,2,4]oxadiazol-3-yl}-6-methyl-phenoxy)-propane-1,2-diol;
- (S)-3-(2-chloro-4-{5-[6-(1-ethyl-propyl)-4-methoxy-pyridin-2-yl]-[1,2,4]oxadiazol-3-yl}-6-methyl-phenoxy)-propane-1,2-diol;
- N—[(S)-3-(2-ethyl-4-{5-[6-(1-ethyl-propyl)-4-methoxy-pyridin-2-yl]-[1,2,4]oxadiazol-3-yl}-6-methyl-phenoxy)-2-hydroxy-propyl]-2-hydroxy-acetamide;
- N—[(S)-3-(4-{5-[6-(1-ethyl-propyl)-4-methoxy-pyridin-2-yl]-[1,2,4]oxadiazol-3-yl}-2,6-dimethyl-phenoxy)-2-hydroxy-propyl]-2-hydroxy-acetamide;
- N—[(S)-3-(2-chloro-4-{5-[6-(1-ethyl-propyl)-4-methoxy-pyridin-2-yl]-[1,2,4]oxadiazol-3-yl}-6-methyl-phenoxy)-2-hydroxy-propyl]-2-hydroxy-acetamide;
- N—[(S)-3-(4-{5-[6-(1-ethyl-propyl)-4-methoxy-pyridin-2-yl]-[1,2,4]oxadiazol-3-yl}-2-methoxy-6-methyl-phenoxy)-2-hydroxy-propyl]-2-hydroxy-acetamide; and
- N-((2S)-3-{2-ethyl-4-[3-(5-isobutyl-4-methyl-pyridin-2-yl)-[1,2,4]oxadiazol-5-yl]-6-methyl-phenoxy}-2-hydroxy-propyl)-2-hydroxy-acetamide;

or a salt of such a compound.

14. A pharmaceutical composition comprising a compound according to claim 1, or a pharmaceutically acceptable salt thereof, and a pharmaceutically acceptable carrier.

\* \* \* \* \*

UNITED STATES PATENT AND TRADEMARK OFFICE
CERTIFICATE OF CORRECTION

PATENT NO. : 8,575,200 B2  
APPLICATION NO. : 12/920656  
DATED : November 5, 2013  
INVENTOR(S) : Bolli et al.

Page 1 of 1

It is certified that error appears in the above—identified patent and that said Letters Patent is hereby corrected as shown below:

In the Claims

Please replace:

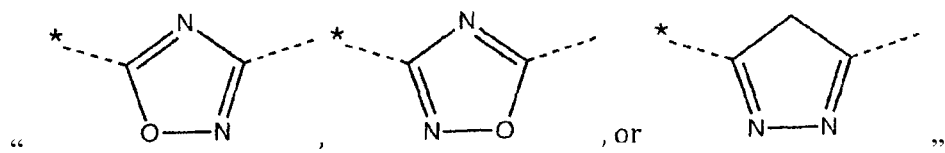

in Column 57, line 50, claim 1 with

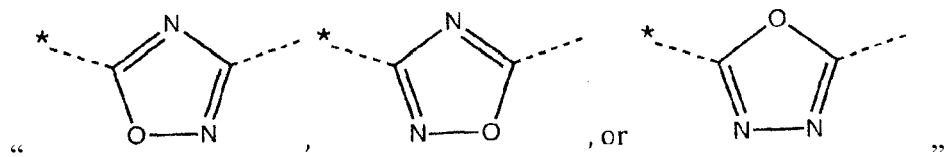

and

"—O—CH$_2$—CH(OH)—CH$_2$—NR$^6$R$^6$" in Column 58, line 2 with
"—O—CH$_2$—CH(OH)—CH$_2$—NR$^{61}$R$^{62}$"

Signed and Sealed this  
Thirteenth Day of May, 2014

Michelle K. Lee  
*Deputy Director of the United States Patent and Trademark Office*

UNITED STATES PATENT AND TRADEMARK OFFICE
CERTIFICATE OF CORRECTION

PATENT NO.       : 8,575,200 B2                                    Page 1 of 1
APPLICATION NO.  : 12/920656
DATED            : November 5, 2013
INVENTOR(S)      : Bolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 244 days.

Signed and Sealed this
Twenty-second Day of September, 2015

Michelle K. Lee
*Director of the United States Patent and Trademark Office*